United States Patent
Undheim et al.

(10) Patent No.: US 8,076,301 B2
(45) Date of Patent: *Dec. 13, 2011

(54) 10-SUBSTITUTED MACROLIDE ANTIBIOTICS

(75) Inventors: Kjell Undheim, Sandvika (NO); Solvi Gunnes, Olso (NO)

(73) Assignee: C10 Pharma AS (NO)

( * ) Notice: Subject to any disclaimer, the term of this patent is extended or adjusted under 35 U.S.C. 154(b) by 0 days.

This patent is subject to a terminal disclaimer.

(21) Appl. No.: 12/569,926

(22) Filed: Sep. 30, 2009

(65) Prior Publication Data

US 2010/0137234 A1    Jun. 3, 2010

Related U.S. Application Data

(62) Division of application No. 10/539,759, filed as application No. PCT/GB03/05659 on Dec. 22, 2003, now Pat. No. 7,608,596.

(30) Foreign Application Priority Data

Dec. 20, 2002  (DK) ................................ 2002 01957

(51) Int. Cl.
*A61K 31/70*  (2006.01)
*C07H 17/08*  (2006.01)

(52) U.S. Cl. ............................. 514/29; 536/7.2; 536/7.4

(58) Field of Classification Search ........................ None
See application file for complete search history.

(56) References Cited

U.S. PATENT DOCUMENTS

2004/0029818 A1    2/2004  Gu et al.

FOREIGN PATENT DOCUMENTS

| FR | 2 692 579 | 6/1992 |
|---|---|---|
| WO | WO 98/01571 | 1/1998 |
| WO | WO 98/25942 | 6/1998 |
| WO | WO 98/51695 | 11/1998 |
| WO | WO 02/060912 | 8/2002 |
| WO | WO 03093289 A1 | 11/2003 |

OTHER PUBLICATIONS

Chu, D. TW "Recent developments is 14-and 15-membered macrolides" Exp. Opin. Invest. Drugs, vol. 4, No. 2, 1995, pp. 65-94.
International Search Report and Written Opinion, International Application No. PCT/GB03/05659; International Filing Date Dec. 22, 2003; Applicant's File Reference 444.83013000; Date of Mailing Dec. 20, 2002; 14 pages.

*Primary Examiner* — Elli Peselev
(74) *Attorney, Agent, or Firm* — Cantor Colburn LLP

(57) ABSTRACT

Disclosed herein are 10-desmethyl, 10 substituted-macrolides, their preparation, pharmaceutical compositions containing them, their use and methods of treatment using them. The 10-desmethyl macrolides are particularly useful as antibiotics.

3 Claims, No Drawings

10-SUBSTITUTED MACROLIDE ANTIBIOTICS

CROSS-REFERENCE TO RELATED APPLICATIONS

This application is a divisional of U.S. patent application Ser. No. 10/539,759, filed Mar. 10, 2006, now U.S. Pat. No. 7,608,569, which is a National Phase filing under 35 U.S.C. §371 of International Application No. PCT/GB0-3/05659 filed on Dec. 22, 2003, which claims priority to Danish Application No. PA 2002 01957, filed Dec. 20, 2002, all of which are incorporated by reference herein in their entirety.

FIELD OF INVENTION

This invention relates to a novel class of antibiotic agents, more specifically 10-desmethyl, 10-substituted-macrolides, their preparation, pharmaceutical compositions containing them, their use and methods of treatment using them.

BACKGROUND

The macrolide antibiotics are a large class of compounds, many derived from *Streptomyces* spp, which comprise a saturated $C_{13}ON_x$ (where x is 0 or 1) macrocyclic lactone ring substituted by one or more sugars, generally at the 5-carbon and optionally also at the 3-carbon. One early example is erythromycin A which has a $C_{13}O$ ring substituted by sugars at the 3 and 5 ring carbons (the ester carbonyl is at the 1 position and the ester ring oxygen at the 14 position).

Later generation macrolide antibiotics include clarithromycin (which is methoxy substituted at the 6-carbon), azithromycin (which has a ring nitrogen between the 9- and 10-carbons, i.e. at the 9a position), telithromycin (which is oxo-substituted at the 3-carbon, methoxy-substituted at the 6-carbon, and has the 11- and 12-carbons substituted by a bridging N-(4-(pyridin-3-yl)-imidazol-1-yl-butyl)cyclic carbamate group), roxithromycin (which is substituted at the 9 position an O-alkylated oxime group), dirithromycin (which is substituted at the 9 and 11 positions by a substituted oxazine group), flurithromycin (which is 8-substituted by fluorine), CP 544372 (which is substituted on the 4' position of the 3-attached sugar by a 2-methoxyphenyleth-1-yl-N-ethyl-aminoethyl-aminocarbonyloxy group and at the 9 position by an amino group), and cethromycin (which is substituted at the 3 position by an oxo group, at the 6 position by a quinolin-3-yl allyloxy group and at the 11 and 12 positions by a cyclic urethane group). Further known antibiotic macrolides include A20316, A69334, A66321, A60565, A216599, A217213, A229339, A241550, CP642959, CP654743, CP642957, CP647762, CP647763, FMA122, FMA174, FMA187, FMA199, FMA367, FMA481, HMR3004, HMR3562, HMR3787, L701677, RWJ415663, RWJ415667, TE604, TE802, TE810, TEA777 and TEA824. Other examples may be found in Asaka et al. Current Topics in Medicinal Chemistry 3: 961-989 (2003) and Wu et al Current Medicinal Chemistry 8: 1727-1758 (2001) and the references therein the contents of all of which are hereby incorporated herein by reference.

The 3-oxo-substituted macrolides are also referred to as ketolides.

A further general feature of the known macrolides is that the 5-sugar is 3'-substituted by a secondary nitrogen (e.g. by a $—N(CH_3)_2$ group), that the 6-carbon carries a hydroxy or substituted hydroxy group, and that they are methyl-substituted at the 2, 4, 6, 8, 10 and 12-carbons.

As with antibiotics in general, there is an ongoing need for novel macrolide antibiotics as drug resistance to the existing compounds appear. There is also a need to increase the activity profile, i.e. the antibacterial toxicity and the range of bacteria against which the macrolide antibiotics are toxic.

While modifying the ring substitution of the macrolides at many ring positions, in particular at the 3, 5, 6, 8, 9, 11 and 12 carbons and between the 9- and 11-carbons and between the 11- and 12-carbons, has been widely suggested, in the over 50 years since the development of erythromycin it has not to our knowledge been suggested that useful new macrolide antibiotics can be produced by modifying the substitution of the 10-carbon. Methyl substitution at the 10-carbon appears to have been uniformly considered to be essential. This is nicely illustrated by Chiron's recent PCT application WO 03/004509 which shows optional substitutional modification at the 2, 4, 6, 9, 11, 12 and 13 carbons (and remember the known macrolide flurithromycin has substitutional modification at the 8-carbon) but still mandates retention of the methyl groups at the 2, 4, 6, 8 and 10 carbons.

SUMMARY

We have now surprisingly found that 10-desmethyl macrolides, i.e. macrolides carry a substituent (but one other than methyl) at the 10-carbon, have desirable antibiotic properties.

Thus viewed from one aspect this invention provides 10-substituted-10-desmethyl macrolides.

Viewed from a further aspect the invention provides a pharmaceutical composition comprising an antibiotic 10-substituted-10-desmethyl macrolide together with at least one pharmaceutical excipient.

Viewed from a still further aspect the invention provides the use of an antibiotic 10-substituted-10-desmethyl macrolide for the manufacture of a medicament for use in the treatment or prevention of infection in animals, preferably mammals.

Viewed from a yet still further aspect the invention provides a method of treatment of a human or animal (preferably mammalian) subject to combat bacterial infection thereof, which method comprises administering to said subject an antibacterially effective amount of an antibiotic 10-substituted-10-desmethyl macrolide.

DETAILED DESCRIPTION

Where referred to herein, a 10-desmethyl macrolide is a macrolide having a non $CH_3$ substituent at the 10-carbon of a $C^{13}ON_8$ lactone ring, preferably one having a carbon-attached substituent at the 10-carbon.

In the 10-desmethyl macrolides of the invention, substitution at all other ring positions may be as described in the literature for 10-methyl macrolides. Particularly preferably the substitution pattern, other than at the 10-carbon, for each position is selected from the set of substituents present in the known macrolides mentioned above. Thus the 2 carbon is preferably methyl or methyl and fluorine substituted, the 3 carbon preferably is oxo, or optionally substituted hydroxy (e.g. sugar (e.g. cladinosyl) or acyloxy-substituted), the 4 carbon is preferably methyl substituted, the 5 carbon is preferably sugar substituted (especially substituted by an oxygen-attached desosamine), the 6-carbon is preferably methyl and hydroxy or substituted hydroxy (e.g. methoxy or arylalkyloxy) substituted, the 7 carbon is preferably unsubstituted, the 8 carbon is preferably methyl or methyl and fluorine substituted, the 9 carbon is preferably unsubstituted (where the ring is $C_{13}ON$) or oxo, amino or imino substituted (which groups themselves may be substituted or form part of a bridging structure), especially oxo substituted, the 11 carbon is preferably hydroxyl, amino or substituted hydroxyl or amino substituted, the 12 carbon is preferably methyl and hydroxy or amino or substituted hydroxy or amino substituted, or more preferably the 11 and 12 carbons and optionally also the 10 carbon are substituted by groups forming a fused ring, and the 13 carbon is preferably ethyl substituted. The substituting groups, especially at the 6, 11 and/or 12 carbons or a 9a nitrogen may optionally together form a fused cyclic group, e.g. at the 11 and 12 carbons, and may desirably carry pendant aromatic groups, especially aromatic rings containing 5 to 10 ring atoms.

Such substituents at the positions conventionally substituted in the known macrolides may be introduced by synthetic techniques conventional in macrolide synthesis or by using a correspondingly substituted conventional macrolide as a starting material.

The group at the 10 carbon is preferably methylene ($=CH_2$), CHO or an optionally substituted carboxy group or a substituted methyl group, e.g. a methyl group substituted by one or more groups selected from $N_3$, halo, cyano, carboxy, substituted carboxy, amino, substituted amino (e.g. alkylamino, aralkylamino, etc.), $C_{1-6}$ alkyl, alkenyl or alkylaryl, aryl, aralkyl, arylkenyl, aralkynyl, hydroxy, substituted hydroxy (e.g. acyloxy) or a group forming a bridge to a substituent on the 11 carbon or, less preferably, the 9 carbon. The 10-substituent however is desirably either polar (e.g. nitrogen containing) or small, e.g. having a total of no more than 6 non-hydrogen atoms.

Unless otherwise specified herein, alkyl, alkenyl, alkynyl moieties preferably contain up to 6 carbons; aryl moieties preferably contain 5 to 10 ring atoms selected from C, N, O and S, especially C and N, especially preferably 0, 1 or 2 being heteroatoms, especially N atoms; and acyl groups are preferably alkylcarbonyl or aralkylcarbonyl groups, optionally ones in which the alkylene group is interrupted by aza groups.

In a particularly preferred embodiment the substitution pattern on a $C_{13}O$ macrolide according to the invention (where the 7-carbon is unsubstituted) is substituted: in the 2-position by methyl and hydrogen or fluorine; in the 3-position by oxo or optionally substituted hydroxy; in the 4-position by methyl; in the 5-position by an oxygen-attached desosamine; in the 6-position by methyl and an optionally substituted hydroxyl; in the 8-position by methyl and hydrogen or fluorine; in the 9-position by oxo; in the 10-position by methylene, CHO, substituted methyl, or carboxy or substituted carboxy; in the 11- and 12-positions by a group forming a fused ring at the 11, 12 and optionally 10-positions; at the 12-position additionally by a methyl group; and at the 13-position by an ethyl group.

The 10-desmethyl macrolides of the invention may, depending on their substitution pattern, be in the form of salts with physiologically tolerable counterions.

Such counterions, e.g. sodium, chloride, ammonium, meglumine, etc, are well known in the pharmacological field.

Further examples of substituents at the 10 carbon include
(1) methyl substituted with one or more substituents selected from the group consisting of
(i) CN,
(ii) F,
(iii) $CO_2R^3$ wherein $R^3$ is selected from hydrogen, $C_1$-$C_3$-alkyl or aryl substituted $C_1$-$C_3$-alkyl, or heteroaryl substituted $C_1$-$C_3$-alkyl,
(iv) $OR^4$ wherein $R^4$ is selected from hydrogen, $C_1$-$C_4$-alkyl or aryl substituted $C_1$-$C_4$-alkyl, or heteroaryl substituted $C_1$-$C_4$-alkyl, heterocycloalkyl and optionally substituted cycloalkyl, $C_1$-$C_3$-alkoxy-$C_1$-$C_3$-alkoxy, $C_1$-$C_4$-alkenyl or aryl substituted $C_1$-$C_4$-alkenyl, or heteroaryl substituted $C_1$-$C_4$-alkenyl, heterocycloalkyl and optionally substituted cycloalkyl, aryl or optionally substituted aryl, heteroaryl or optionally substituted heteroaryl,
(v) $S(O)_nR^3$ wherein n=0, 1 or 2 and $R^3$ is as previously defined
(vi) $NR^4C(O)R^3$ wherein $R^3$ and $R^4$ are as previously defined
(vii) $NR^4C(O)NR^5R^6$ wherein $R^4$ is defined as defined previously, and $R^5$ and $R^6$ are independently selected from hydrogen, $C_1$-$C_3$-alkyl, $C_1$-$C_3$ alkyl substituted with aryl, substituted aryl, heteroaryl, substituted heteroaryl
(viii) $NR^7R^8$ wherein $R^7$ and $R^8$ are independently selected from the group consisting of
(a) hydrogen
(b) $C_1$-$C_{12}$-alkyl, and optionally substituted $C_1$-$C_{12}$-alkyl
(c) $C_2$-$C_{12}$-alkenyl, and optionally substituted $C_2$-$C_{12}$-alkenyl (d) $C_2$-$C_{12}$-alkynyl, and optionally substituted $C_2$-$C_{12}$-alkynyl
(e) aryl, and optionally substituted aryl
(f) heteroaryl, and optionally substituted heteroaryl
(g) heterocycloalkyl, and optionally substituted heterocycloalkyl
(h) $C_1$-$C_{12}$ alkyl substituted with aryl, and optionally substituted with substituted aryl
(i) $C_1$-$C_{12}$ alkyl substituted with heteroaryl, and optionally substituted with substituted heteroaryl
(j) $C_1$-$C_{12}$ alkyl substituted with heterocycloalkyl, and with optionally substituted heterocycloalkyl, and
(k) $R^7$ and $R^8$ taken together with the atom to which they are attached from a 3-10-membered heterocycloalkyl ring which may contain one or more additional heteroatoms and may be substituted with one or more substituents independently selected from the group consisting of
(aa) halogen, hydroxy, $C_1$-$C_3$-alkoxy, alkoxy-$C_1$-$C_3$-alkoxy, oxo, $C_1$-$C_3$-alkyl, aryl and optionally substituted aryl, heteroaryl and optional substituted heteroaryl
(bb) $CO_2R^3$ wherein $R^3$ is as previously defined, and
(cc) $C(O)NR^5R^6$ wherein $R^5$ and $R^6$ are as previously defined,
(ix) aryl, and optionally substituted aryl, and
(x) heteroaryl, and optionally substituted heteroaryl,
(2) $C_2$-$C_{10}$-alkyl,
(3) $C_2$-$C_{10}$-alkyl substituted with one or more substituents selected from the group consisting of
(i) halogen,
(ii) $OR^4$ wherein $R^4$ is as defined previously
(iii) —CHO,
(iv) oxo,
(v) $NR^7R^8$ wherein $R^7$ and $R^8$ are defined as previously
(vi) $=N$—O—$R^4$ is wherein $R^3$ is as previously defined
(vii) —CN
(viii) —$S(O)_nR^3$ wherein n=0, 1 or 2 and $R^3$ is as previously defined
(ix) aryl, and optionally substituted aryl
(x) heteroaryl, and optionally substituted heteroaryl
(xi) $C_3$-$C_8$-cycloalkyl, and optionally substituted $C_3$-$C_8$-cycloalkyl
(xii) heterocycloalkyl, and optionally substituted heterocycloalkyl
(xiii) $NR^4C(O)R^3$ where $R^3$ and $R^4$ are as previously defined
(xiv) $NR^4C(O)NR^5R^6$ wherein $R^4$, $R^5$ and $R^6$ are as previously defined
(xv) $=N$—$NR^7R^8$ wherein $R^7$ and $R^8$ are as previously defined
(xvi) $=N$—$R^4$ wherein $R^4$ is as previously defined
(xvii) $=N$—$NR^4C(O)R^3$ wherein $R^3$ and $R^4$ are as previously defined, and
(xviii) $=N$—$NR^4C(O)NR^5R^6$ wherein $R^4$, $R^5$ and $R^6$ are as previously defined, (4) $C_2$-$C_{10}$-alkenyl,
(5) $C_2$-$C_{10}$-alkenyl substituted with one or more substituents selected from the group consisting of
  (i) halogen,
  (ii) $OR^4$ wherein $R^4$ is as previously defined
  (iii) $O-S(O)_nR^3$ where n and $R^3$ are as previously defined
  (iv) —CHO,
  (v) oxo,
  (vi) —$CO_2R^3$ where $R^3$ is as previously defined
  (vii) —C(O)—$R^4$ where $R^4$ is as previously defined
  (viii) —CN
  (ix) aryl, and optionally substituted aryl
  (x) heteroaryl, and optionally substituted heteroaryl
  (xi) $C_3$-$C_7$-cycloalkyl
  (xii) $C_1$-$C_{12}$-alkyl substituted with heteroaryl
  (xiii) $NR^7R^8$ wherein $R^7$ and $R^8$ are as previously defined
  (xiv) $NR^4C(O)R^3$ where $R^3$ and $R^4$ are as previously defined
  (xv) $NR^4C(O)NR^5R^6$ where $R^4$, $R^5$ and $R^6$ are as previously defined
  (xvi) =N—O—$R^4$ where $R^4$ is as previously defined
  (xvii) =N—$NR^7R^8$ wherein $R^7$ and $R^8$ are as previously defined
  (xviii) =N—$NR^4$ wherein $R^4$ is as previously defined
  (xix) =N—$NR^4C(O)R^3$ wherein $R^3$ and $R^4$ are as previously defined, and
  (xx) =N—$NR^4C(O)NR^5R^6$ wherein $R^4$, $R^5$ and $R^6$ are as previously defined,
(6) $C_2$-$C_{10}$-alkynyl
(7) $C_2$-$C_{10}$-alkynyl substituted with one or more substituents selected from the group consisting of
  (i) trialkylsilyl
  (ii) halogen,
  (iii) —CN
  (iv) $OR^4$ where $R^4$ is defined as previously
  (v) —CHO,
  (vi) oxo,
  (vii) —$CO_2R^3$ where $R^3$ is as previously defined
  (viii) —$C(O)NR^5R^6$ wherein $R^5$ and $R^6$ are as previously defined
  (ix) $NR^7R^8$ wherein $R^7$ and $R^8$ are as previously defined
  (x) $O-S(O)_nR^3$ where n and $R^3$ are as previously defined
  (xi) $C_3$-$C_7$-cycloalkyl
  (xii) $C_1$-$C_{12}$-alkyl substituted with heteroaryl
  (xiii) aryl, and optionally substituted aryl
  (xiv) heteroaryl, and optionally substituted heteroaryl
  (xv) $NR^4C(O)R^3$ where $R^3$ and $R^4$ are as previously defined
  (xvi) $NR^4C(O)NR^5R^6$ where $R^4$, $R^5$ and $R^6$ are as previously defined
  (xvii) =N—O—$R^4$ where $R^4$ is as previously defined
  (xviii) =N—$NR^7R^8$ wherein $R^7$ and $R^8$ are as previously defined
  (xix) =N—$NR^4C(O)R^3$ wherein $R^3$ and $R^4$ are as previously defined, and
  (xx) =N—$NR^4C(O)NR^5R^6$ wherein $R^4$, $R^5$ and $R^6$ are as previously defined,
(8) cyclic substituents
  (i) aryl, and optionally substituted aryl
  (ii) heteroaryl, and optionally substituted heteroaryl
  (iii) heterocycloalkyl, and optionally substituted heterocycloalkyl, and
  (iv) $C_3$-$C_7$-cycloalkyl, and optionally substituted $C_3$-$C_7$-cycloalkyl, and
(9) $C_1$ substituents with the exception of 10-methyl derivatives which are part of the above definitions under (1)
  (i) —CHO
  (ii) —CN
  (iii) $CO_2R^3$ wherein $R^3$ is as previously defined
  (iv) $C(O)NR^5R^6$ wherein $R^5$ and $R^6$ are as previously defined
  (v) $C(S)NR^5R^5$ wherein $R^5$ and $R^6$ are as previously defined
  (vi) $C(NR^4)NR^5R^6$ wherein $R^4$, $N^5$ and $R^6$ are as previously defined
  (vii) CH=N—O—$R^4$ wherein $R^4$ is as previously defined
  (viii) CH=N—$R^4$ is wherein $R^4$ is as previously defined
  (ix) CH=N—$NR^7R^8$ wherein $R^7$ and $R^8$ are as previously defined
  (x) CH=N—$NR^4C(O)R^3$ wherein $R^3$ and $R^4$ are as previously defined, and
  (xi) CH=N—$NR^4C(O)NR^5R^6$ wherein $R^4$, $R^5$ and $R^6$ are as previously defined.

The identities 1(iv), 1(viii), 2 and 5(ix) are particularly preferred.

Thus for example the macrolides of the invention may typically be of formula I

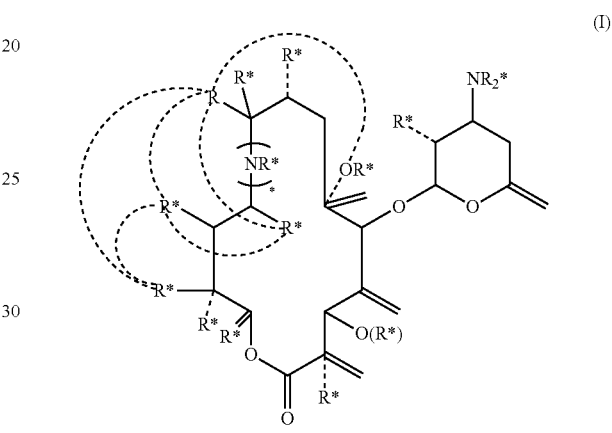

(where the 3 position R* is an oxo, acyloxy or sugar (preferably cladinose) moiety, and the dashed lines indicate possible bridging between substituents at two ring positions). The "R*" groups are not defined in relation to formula I as this formula is used for illustrative purposes. Such groups, except the R at the 10 carbon may be as in the earlier published descriptions of 10-methyl macrolides, e.g. as in WO 03/004509, the documents cited therein and in the Search Report issued in relation thereto, or in Martindale—The Computer Drug Reference, 32$^{nd}$ Edition, 1999, the Antibacterials chapter at page 112 et seq. and in Asaka et al (supra) and Wu et al (supra). All of these are incorporated herein by reference.

Particular embodiments of formula I are given by formulae II, III, IV and V below

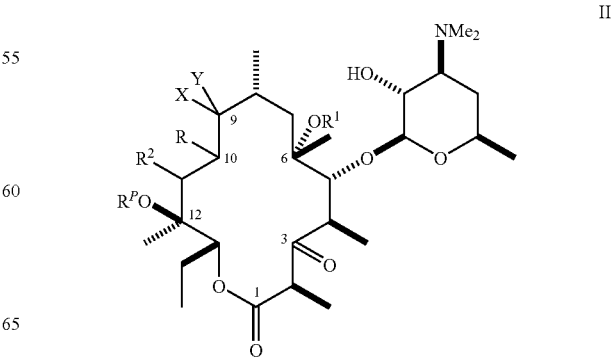

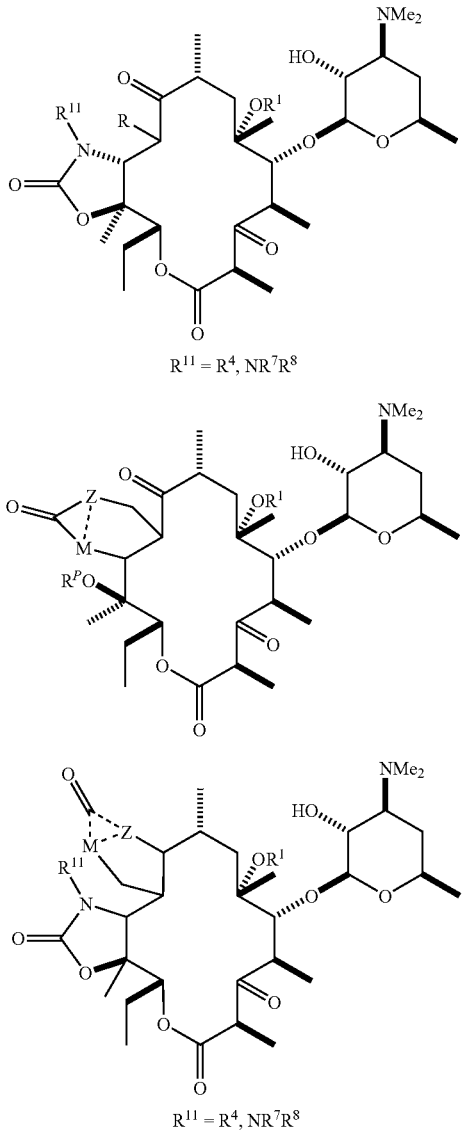

$R^{11} = R^4, NR^7R^8$ (III)

$R^{11} = R^4, NR^7R^8$ (V)

(1) R is methyl substituted with one or more substituents selected from the group consisting of
(i) CN,
(ii) F,
(iii) $CO_2R^3$ wherein $R^3$ is selected from hydrogen, $C_1$-$C_3$-alkyl or aryl substituted $C_1$-$C_3$-alkyl, or heteroaryl substituted $C_1$-$C_3$-alkyl,
(iv) $OR^4$ wherein $R^4$ is selected from hydrogen, $C_1$-$C_4$-alkyl or aryl substituted $C_1$-$C_4$-alkyl, or heteroaryl substituted $C_1$-$C_4$-alkyl, heterocycloalkyl and optionally substituted cycloalkyl, $C_1$-$C_3$-alkoxy-$C_1$-$C_3$-alkoxy, $C_2$-$C_4$-alkenyl or aryl substituted $C_2$-$C_4$-alkenyl, or heteroaryl substituted $C_2$-$C_4$-alkenyl, heterocycloalkyl and optionally substituted cycloalkyl, aryl or optionally substituted aryl, heteroaryl or optionally substituted heteroaryl,
(v) $S(O)_nR^3$ wherein n=0, 1 or 2 and $R^3$ is as previously defined
(vi) $NR^4C(O)R^3$ wherein $R^3$ and $R^4$ are as previously defined
(vii) $NR^4C(O)NR^5R^6$ wherein $R^4$ is defined as defined previously, and $R^5$ and $R^6$ are independently selected from hydrogen, $C_1$-$C_3$-alkyl, $C_1$-$C_3$ alkyl substituted with aryl, substituted aryl, heteroaryl, substituted heteroaryl (viii) $NR^7R^8$ wherein $R^7$ and $R^8$ are independently selected from the group consisting of
(a) hydrogen
(b) $C_1$-$C_{12}$-alkyl, and optionally substituted $C_1$-$C_{12}$-alkyl
(c) $C_2$-$C_{12}$-alkenyl, and optionally substituted $C_2$-$C_{12}$-alkenyl
(d) $C_2$-$C_{12}$-alkynyl, and optionally substituted $C_2$-$C_{12}$-alkynyl
(e) aryl, and optionally substituted aryl
(f) heteroaryl, and optionally substituted heteroaryl
(g) heterocycloalkyl, and optionally substituted heterocycloalkyl
(h) $C_1$-$C_{12}$ alkyl substituted with aryl, and optionally substituted with substituted aryl
(i) $C_1$-$C_{12}$ alkyl substituted with heteroaryl, and optionally substituted with substituted heteroaryl
(j) $C_1$-$C_{12}$ alkyl substituted with heterocycloalkyl, and with optionally substituted heterocycloalkyl, and
(k) $R^7$ and $R^8$ taken together with the atom to which they are attached from a 3-10-membered heterocycloalkyl ring which may contain one or more additional heteroatoms and may be substituted with one or more substituents independently selected from the group consisting of
(aa) halogen, hydroxy, $C_1$-$C_3$-alkoxy, alkoxy-$C_1$-$C_3$-alkoxy, oxo, $C_1$-$C_3$-alkyl, aryl and optionally substituted aryl, heteroaryl and optional substituted heteroaryl
(bb) $CO_2R^3$ wherein $R^3$ is as previously defined, and
(cc) $C(O)NR^5R^6$ wherein $R^5$ and $R^6$ are as previously defined,
(ix) aryl, and optionally substituted aryl, and
(x) heteroaryl, and optionally substituted heteroaryl,
(2) $C_2$-$C_{10}$-alkyl,
(3) $C_2$-$C_{10}$-alkyl substituted with one or more substituents selected from the group consisting of
(i) halogen,
(ii) $OR^4$ wherein $R^4$ is as defined previously
(iii) —CHO,
(iv) oxo,
(v) $NR^7R^8$ wherein $R^7$ and $R^8$ are defined as previously
(vi) =N—O—$R^4$ is wherein $R^3$ is as previously defined
(vii) —CN
(viii) —$S(O)_nR^3$ wherein n=0, 1 or 2 and $R^3$ is as previously defined
(ix) aryl, and optionally substituted aryl
(x) heteroaryl, and optionally substituted heteroaryl
(xi) $C_3$-$C_8$-cycloalkyl, and optionally substituted $C_3$-$C_8$-cycloalkyl
(xii) heterocycloalkyl, and optionally substituted heterocycloalkyl
(xiii) $NR^4C(O)R^3$ where $R^3$ and $R^4$ are as previously defined
(xiv) $NR^4C(O)NR^5R^6$ wherein $R^4$, $R^5$ and $R^6$ are as previously defined
(xv) =N—$NR^7R^8$ wherein $R^7$ and $R^8$ are as previously defined
(xvi) =N—$R^4$ wherein $R^4$ is as previously defined
(xvii) =N—$NR^4C(O)R^3$ wherein $R^3$ and $R^4$ are as previously defined, and
(xviii) =N—$NR^4C(O)NR^5R^6$ wherein $R^4$, $R^5$ and $R^6$ are as previously defined,
(4) $C_2$-$C_{10}$-alkenyl,
(5) $C_2$-$C_{10}$-alkenyl substituted with one or more substituents selected from the group consisting of
(i) halogen,
(ii) $OR^4$ wherein $R^4$ is as previously defined
(iii) O—$S(O)_nR^3$ where n and $R^3$ are as previously defined
(iv) —CHO,
(v) oxo, (vi) —CO$_2$R$^3$ where R$^3$ is as previously defined
(vii) —C(O)—R$^4$ where R$^4$ is as previously defined
(viii) —CN
(ix) aryl, and optionally substituted aryl
(x) heteroaryl, and optionally substituted heteroaryl
(xi) C$_3$-C$_7$-cycloalkyl
(xii) C$_1$-C$_{12}$-alkyl substituted with heteroaryl
(xiii) NR$^7$R$^8$ wherein R$^7$ and R$^8$ are as previously defined
(xiv) NR$^4$C(O)R$^3$ where R$^3$ and R$^4$ are as previously defined
(xv) NR$^4$C(O)NR$^5$R$^6$ where R$^4$, R$^5$ and R$^6$ are as previously defined
(xvi) =N—O—R$^4$ where R$^4$ is as previously defined
(xvii) =N—NR$^7$R$^8$ wherein R$^7$ and R$^8$ are as previously defined
(xviii) =N—NR$^4$ wherein R$^4$ is as previously defined
(xix) =N—NR$^4$C(O)R$^3$ wherein R$^3$ and R$^4$ are as previously defined, and
(xx) =N—NR$^4$C(O)NR$^5$R$^6$ wherein R$^4$, R$^5$ and R$^6$ are as previously defined,
(6) C$_2$-C$_{10}$-alkynyl
(7) C$_2$-C$_{10}$-alkynyl substituted with one or more substituents selected from the group consisting of
(i) trialkylsilyl
(ii) halogen,
(iii) —CN
(iv) OR$^4$ where R$^4$ is defined as previously
(v) —CHO,
(vi) oxo,
(vii) —CO$_2$R$^3$ where R$^3$ is as previously defined
(viii) —C(O)NR$^5$R$^6$ wherein R$^5$ and R$^6$ are as previously defined
(ix) NR$^7$R$^8$ wherein R$^7$ and R$^8$ are as previously defined
(x) O—S(O)$_n$R$^3$ where n and R$^3$ are as previously defined
(xi) C$_3$-C$_7$-cycloalkyl
(xii) C$_1$-C$_{12}$-alkyl substituted with heteroaryl
(xiii) aryl, and optionally substituted aryl
(xiv) heteroaryl, and optionally substituted heteroaryl
(xv) NR$^4$C(O)R$^3$ where R$^3$ and R$^4$ are as previously defined
(xvi) NR$^4$C(O)NR$^5$R$^6$ where R$^4$, R$^5$ and R$^6$ are as previously defined
(xvii) =N—O—R$^4$ where R$^4$ is as previously defined
(xviii) =N—NR$^7$R$^8$ wherein R$^7$ and R$^8$ are as previously defined
(xix) =N—NR$^4$C(O)R$^3$ wherein R$^3$ and R$^4$ are as previously defined, and
(xx) =N—NR$^4$C(O)NR$^5$R$^6$ wherein R$^4$, R$^5$ and R$^6$ are as previously defined,
(8) cyclic substituents
(i) aryl, and optionally substituted aryl
(ii) heteroaryl, and optionally substituted heteroaryl
(iii) heterocycloalkyl, and optionally substituted heterocycloalkyl, and
(iv) C$_3$-C$_7$-cycloalkyl, and optionally substituted C$_3$-C$_7$-cycloalkyl, and
(9) C$_1$ substituents with the exception of 10-methyl derivatives which are part of the above definitions under (1)
(i) —CHO
(ii) —CN
(iii) CO$_2$R$^3$ wherein R$^3$ is as previously defined
(iv) C(O)NR$^5$R$^6$ wherein R$^5$ and R$^6$ are as previously defined
(v) C(S)NR$^5$R$^6$ wherein R$^5$ and R$^6$ are as previously defined
(vi) C(NR$^4$)NR$^5$R$^6$ wherein R$^4$, N$^5$ and R$^6$ are as previously defined
(vii) CH=N—O—R$^4$ wherein R$^4$ is as previously defined
(viii) CH=N—R$^4$ is wherein R$^4$ is as previously defined
(ix) CH=N—NR$^7$R$^8$ wherein R$^7$ and R$^8$ are as previously defined
(x) CH=N—NR$^4$C(O)R$^3$ wherein R$^3$ and R$^4$ are as previously defined, and
(xi) CH=N—NR$^4$C(O)NR$^5$R$^6$ wherein R$^4$, R$^5$ and R$^6$ are as previously defined;
R$^1$ is selected from the group consisting of
(1) H
(2) methyl
(3) methyl substituted with one or more substituents selected from the group consisting of
(i) F
(ii) —CN
(iii) —CO$_2$R$^{11}$ where R$^{11}$ is C$_1$-C$_3$-alkyl or aryl substituted C$_1$-C$_3$-alkyl, or heteroalkyl substituted C$_1$-C$_3$-alkyl
(iv) —C(O)NR$^5$R$^6$ wherein R$^5$ and R$^6$ are defined as previously
(v) aryl, and optionally substituted aryl, and
(vi) heteroaryl, and optionally substituted heteroaryl
(4) C$_2$-C$_{10}$-alkyl
(5) substituted C$_2$-C$_{10}$-alkyl with one or more substituents selected from the group consisting of
(i) halogen,
(ii) OR$^4$ where R$^4$ is defined as previously
(iii) C$_1$-C$_3$-alkoxy-C$_1$-C$_3$-alkoxy
(iv) —CHO
(v) oxo
(vi) NR$^7$R$^8$ wherein R$^7$ and R$^8$ are as previously defined
(vii) =N—O—R$^4$ where R$^4$ is as previously defined
(viii) —CN
(ix) —S(O)R$^3$ where n=0, 1, or 2 and R$^3$ is as previously defined
(x) aryl, and optionally substituted aryl
(xi) heteroaryl, and optionally substituted heteroaryl
(xii) C$_3$-C$_8$-cycloalkyl, and optionally substituted C$_3$-C$_8$-cycloalkyl
(xiii) C$_1$-C$_{12}$-alkyl substituted with heteroaryl, and optionally substituted heteroaryl
(xiv) heterocycloalkyl
(xv) NHC(O)R$^3$ where R$^3$ is as previously defined
(xvi) NHC(O)NR$^5$R$^6$ where R$^5$ and R$^6$ are as previously defined
(xvii) =N—NR$^7$R$^8$ wherein R$^7$ and R$^8$ are as previously defined
(xviii) =N—R$^4$ wherein R$^4$ as previously defined, and
(xix) =N—NHC(O)R$^3$ wherein R$^3$ is as previously defined,
(4) C$_1$-C$_{10}$-alkenyl substituted with one or more substituents selected from the group consisting of
(i) halogen,
(ii) OR$^4$ where R$^4$ is as previously defined
(iii) —CHO
(iv) oxo
(v) —S(O)$_n$R$^3$ where n and R$^3$ are as previously defined
(vi) —CN
(vii) —CO$_2$R$^3$ where R$^3$ is as previously defined
(viii) NR$^7$R$^8$ wherein R$^7$ and R$^8$ are as previously defined
(ix) =N—O—R$^4$ where R$^4$ is as previously defined
(x) —C(O)—R$^4$ where R$^4$ is as previously defined
(xi) —C(O)NR$^5$R$^6$ wherein R$^5$ and R$^6$ are as previously defined
(xii) aryl, and optionally substituted aryl
(xiii) heteroaryl, and optionally substituted heteroaryl
(xiv) C$_3$-C$_7$-cycloalkyl
(xv) C$_1$-C$_{12}$-alkyl substituted with heteroaryl
(xvi) NHC(O)R$^3$ where R$^3$ is as previously defined
(xvii) NHC(O)NR$^5$R$^6$ where R$^5$ and R$^6$ are as previously defined
(xviii) =N—NR$^7$R$^8$ wherein R$^7$ and R$^8$ are as previously defined (xix) =N—$R^4$ wherein $R^4$ is as previously defined,
(xx) =N—NHC(O)$R^3$ wherein $R^3$ is as previously defined, and
(xxi) =N—NHC(O)N$R^5R^6$ wherein $R^5$ and $R^6$ are as previously defined,
(5) $C_2$-$C_{10}$-alkynyl, and
(6) $C_2$-$C_{10}$-alkynyl substituted with one or more substituents selected from the group consisting of
(i) halogen,
(ii) O$R^4$ where $R^4$ is defined as previously
(iii) —CHO
(iv) oxo
(v) —CO$_2R^3$ where $R^3$ is as previously defined
(vi) —C(O)N$R^5R^6$ wherein $R^5$ and $R^6$ are as previously defined
(vii) —CN
(viii) N$R^7R^8$ wherein $R^7$ and $R^8$ are as previously defined
(ix) =N—O—$R^4$ where $R^4$ is as previously defined
(x) —S(O)$_nR^3$ where n and $R^3$ are as previously defined
(xi) aryl, and optionally substituted aryl
(xii) heteroaryl, and optionally substituted heteroaryl
(xiii) $C_3$-$C_7$-cycloalkyl
(xiv) $C_1$-$C_{12}$-alkyl substituted with heteroaryl
(xv) NHC(O)$R^3$ where $R^3$ is as previously defined
(xvi) NHC(O)N$R^5R^6$ where $R^5$ and $R^6$ are as previously defined
(xvii) =N—N$R^7R^8$ wherein $R^7$ and $R^8$ are as previously defined
(xviii) =N—$R^4$ wherein $R^4$ is as previously defined
(xix) =N—NHC(O)$R^3$ wherein $R^3$ is as previously defined, and
(xx) =N—NHC(O)N$R^5R^6$ wherein $R^5$ and $R^6$ are as previously defined;
$R^2$ is selected from the group consisting of
(1) hydrogen
(2) OH
(3) O$R^3$ where $R^3$ is as previously defined
(4) OC(O)$R^3$ where $R^3$ is as previously defined, and
(5) O(CO)O$R^3$ where $R^3$ is as previously defined;
and X and Y taken together are selected from the group consisting of
(1) O
(2) NO$R^4$ wherein $R^4$ is as defined previously
(3) N—OC($R^9$)(C$R^{10}$)—O—$R^4$ where $R^4$ is as previously defined and
  (i) $R^9$ and $R^{10}$ are each independently defined as $R^4$, or
  (ii) $R^9$ and $R^{18}$ are taken together with the atom to which they are attached form a $C_3$-$C_{12}$ cycloalkyl ring,
(4) N$R^4$ wherein $R^4$ is as previously defined, and
(5) N—N$R^7R^8$ wherein $R^7$ and $R^8$ are as previously defined, or one of X and Y is hydrogen and the other is selected from the group consisting of
(1) —O$R^4$ wherein $R^4$ is as previously defined, and
(2) —N$R^7R^8$ wherein $R^7$ and $R^8$ are as previously defined.
$R^P$ is selected from the group consisting of
  (1) hydrogen
  (2) $R^3$ as previously defined
  (3) CO$R^3$ where $R^3$ is as previously defined;
  subject to the proviso that when the structure is IV, Z and M are part of a five- or six-membered ring, said rings optionally being fully or partially unsaturated; for the six-membered ring, the bonding between Z and M is through a carbonyl group; for the five-membered ring, the bonding is directly between Z and M excluding CO; Z and M are independently selected from the group consisting of carbon, oxygen or N; and when M=N a second bridge may exist between this nitrogen and the oxygen of the 12-OH group whereby either an additional annulated oxazole or oxazine ring constitutes part of the molecule; and subject to the proviso that when the structure is V, Z and M are part of a five- or six-membered ring, said rings optionally being fully saturated or fully or partially unsaturated; for the six-membered ring, the bonding between Z and M is through a carbonyl group; for the five-membered ring, the bonding is directly between Z and M excluding CO; Z and M are independently selected from the group consisting of carbon, oxygen or nitrogen; and when M=N a second bridge may exist between this nitrogen and the urethane nitrogen.

In formulae II to V, the substituent at the 10 carbon may also be as described earlier herein. The particularly preferred identities of the substituent at the 10-carbon are those shown for the end products in the reaction schemes set out below.

The macrolides of the invention may, but preferably do not have an oxygen bridge linking the 6 and 9 carbons.

Where the macrolide ring is set out as shown in the formulae drawings herein, the 2-methyl, 4-methyl, 6-methyl, 13-ethyl and 3-optionally substituted hydroxy groups are preferably above the plane, and the 5-sugar, the 6-optionally substituted hydroxy and the 8 and 12 methyl groups are preferably below the plane. The 10-substituent is also preferably below the plane.

Examples of processes for the preparation of the macrolides of the invention are set out below in reaction schemes and Examples. Preferably the processes involve dehydration of a 6-substituted hydroxy, 10-methyl, 11-hydroxyl macrolide and subsequent substitution of the 10 methyl group, e.g. by reaction with NBS (preferably after oxidation of the 3' nitrogen in the 5-sugar), followed if necessary by further reaction, e.g. to modify the 10-substituent, to transform the 10-11 bond to a single bond, to remove protecting groups or to introduce substituents elsewhere on the molecule. Such a process forms a further aspect of the present invention.

The novel macrolides of the invention may be formulated in conventional administration forms, e.g. tablets, coated tablets, powders, granulates, solutions, dispersions, syrups, emulsions, sprays, suppositories, pessaries, etc using conventional excipients, e.g. solvents, diluents, binders, sweeteners, aromas, pH modifiers, viscosity modifiers, antioxidants, etc. Conventional formulation techniques, well known in the art, may be used. The compositions may likewise be administered by conventional administration routes, e.g. orally, by injection, infusion, nasally, rectally, etc. The use of orally administrable compositions, e.g. tablets, coated tablets, syrups, etc is especially preferred.

The macrolides of the invention may be administered in dosage amounts, over dosage periods and at dosage intervals conventional in the use of macrolide antibiotics (e.g. see Martindale, supra and the references for macrolide entries therein). Typical daily dosages for a human or other mammal, given in a single dose or at multiple (e.g. 2, 3 or 4) times per day will generally lie in the range 0.01 to 50 mg/kg bodyweight, especially 0.1 to 25 mg/kg bodyweight.

Many of the intermediates described herein are themselves novel and useful compounds and these form a further aspect of the invention. Thus viewed from a further aspect the invention provides 6-substituted hydroxy-10-acetyloxy-macrolide analogs having a carbon-carbon double bond between the 10 and 11 carbons; macrolide analogs oxidized at the 3' nitrogen of the 5-sugar; 10-desmethyl macrolide analogs having a carbon-carbon double bond between the 10 and 11 carbons and having a substituted hydroxy group at the 12-carbon; and 10-desmethyl macrolides, hydroxy protected at the 2' position of the 5-sugar. Specific examples of such intermediates may be found in the reaction schemes below. Other intermediates which form a further aspect of the invention include those in the reaction schemes below identified by the numbers 3, 4, 5, 5a, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66 and 66a, especially 3, 4, 5, 5a, 6, 7, 8, 9, 10, 11, 12, 13, 14, 15, 16, 17, 18, 29, 30, 31, 32, 33 and 37.

In this context, the term analog is used to mean a compound which, by virtue only of the specified substitution pattern (e.g. the ring unsaturation or 3'N-substituted oxidation) may fall outside the definition herein of a macrolide.

Where the processes of the invention involve use of protecting groups, the invention is not limited to the use of the protecting groups specifically mentioned. A wide range of suitable protecting groups is known in conventional organic synthesis (see for example Greene et al. "Protective Groups in Organic Synthesis", 3rd Edition, Wiley, NY, 1999 and McOmie "Protective Groups in Organic Chemistry", Plenum, 1973 and more recent publications on protecting groups).

Thus for example other protecting groups such as simple esters, ethers removable by hydrogenolysis or mild oxidative conditions, mixed acetals, etc may be used.

The following abbreviations are used herein:
TMS/TMS-triflate: Trimethylsilyl/(Trimethylsilyl)-methyl trifluoromethanesulfonate
TEA: Triethylamine
TES-O: Triethylsilyl trifluoromethanesulfonate
NMP: N-methylpyrrolidone
NBS: N-Bromosuccinimide
TFP: Tri-(2-furyl)phosphine
NaHMDS: Sodium bis(trimethylsilyl) amide
CDI: Carbonyldiimidazole
BSTFA: N,O-Bis(trimethylsilyl)trifluoroacetamide
Pd2(dba)$_3$ CHCl$_3$: tris(dibenzylideneacetone)dipalladium chloroform complex
DMAP: Dimethylaminopyridine
TBAF: Tetrabutyl ammonium fluoride
TMS-O: Trimethylsilyl-ether
Boc$_2$O: benzyloxy carbonyl anhydride
P(o-tol)$_3$: Tri-ortho-toluenephosphine
BnNH$_2$: Benzylamine
TBDMS-triflate/TBDMS: tert-butyl dimethylsilyl trifluoromethanesulfonate
mCPBA: m-chloroperbenzoic acid.
dppe: 1,2 bis(diphenylphosphino)ethane
MeI: Methyliodide Scheme 1

Chemoselective N-oxidation of the spirane 2 was carried out using $H_2O_2$ as the oxidising agent in methanol at room temperature. The product was the desired N-oxide 3 in close to quantitative yield. The N-oxide moiety can be regarded as a protected form of the tertiary amino group for a subsequent chemoselective reaction in the 10-methyl group. The bromination was effected by NBS in acetic acid at room temperature. When bromination was attempted with the amine 2 without the protection by the N-oxide function, several products were formed. The structure of the bromination product 4 has been verified by a single crystal X-ray analysis. Deprotection with removal of the N-oxide function was effected by triphenylphosphine under reflux in THF The product was the 10-bromomethyl derivative 5. Therefore both the latter, and its N-oxide precursor 4, have been substrates (or intermediates) for the subsequent reactions. The 2',3-hydroxy groups in structure 5 are accessible for reactions. Structure 5a shows silyl ether formation.

Scheme 2

In another embodiment of this invention for the preparation of key intermediates as substrates for the target compounds, the 3-ketolide 8 was prepared as shown in Scheme 2. For many reactions it was necessary to protect the reactive 2',3-hydroxy groups in structures 2. Therefore a number of silyl ethers 2a-2c have been prepared as intermediate reactants.

The substrate was erythralosamine 2. Selective protection of the 2'-OH group, as an acetyl derivative 6, was achieved using acetic anhydride with triethylamine. Corey-Kim oxidation of the 3-OH group provided the 3-ketolide 7. Deprotection of the 2'-OH group was by methanol at room temperature. The ketolide 8 (R=Me) can be oxidised to its N-oxide 9 using hydrogen peroxide (vide supra) and brominated to furnish the bromomethyl derivative 10. Phosphine deoxygenation of the N-oxide provides the amine 11. The bromomethyl ketolide 10 is also available by oxidation of the alcohol 5, e.g. under Corey-Kim or related conditions.

Scheme 3

Carbylations by cross-coupling reactions are shown in Scheme 3. The N-oxide 4 was the substrate for the coupling under Stille conditions with tributyl(2-furyl)stannane, tris(2-furyl)phosphine (TFP), Pd$_2$ dba$_3$.CHCl$_3$ in NMP at 80° C. to furnish a furyl derivative which was isolated in 51% yield. Under these conditions concurrent phosphine deoxygenation of the N-oxide function occurred. The product was the amine 13. The substrate for the phenylation reaction was the amine 5. Satisfactory cross-coupling under the same conditions with tributylphenylstannane gave the 10-benzyl derivative 12 in 60% yield. By these reactions we have shown that either the amine 5 or the N-oxide 4 can be the substrate for cross-coupling reactions.

Optionally, a triple bond derivative may be produced. In the simplest case phenylacetylene has been coupled under Stille conditions to provide the alkyne 14. Sonogashira methodology would provide the same product.

A target in this work has been the preparation of the 10-ethyl derivative, e.g. as the silyl protected derivative 15. The reaction has been successfully achieved using trimethylaluminium under palladium-mediated catalysis with the silyl protected substrate 5a as shown in Scheme 3. The methylated product 15 was obtained in high yield, 84%. Simple silyl deprotection provides the parent dihydroxy compound.

Scheme 4

A functionalized alkene 16 has been introduced under Stille conditions as shown in Scheme 4.

The tin reagent was tributyl (1-ethoxyethenyl)stannane. The desired coupling product 16 was isolated in 54% yield. Acid catalysed cleavage of the vinyl ether provides the corresponding methyl ketone 17.

Scheme 5

Either bromo compound 4 or 5 under hydrolytic conditions will furnish the corresponding hydroxymethyl derivative indicated in Scheme 5. The hydrolysis product 18 from the amine 5 is shown. As an allylic alcohol 18 is selectively oxidised, first to the aldehyde 19 that can be further oxidised to the carboxylic acid 20 and subsequently converted into new derivatives via the carboxy function. Alternatively, the aldehyde 19 is converted into a ketone 22 via adduct 21 formation with an organometallic reagent and a subsequent oxidation.

In this manner the 10-methyl group has been functionalised to aldehyde, ketone and carboxylic acid carbonyl groups for further manipulations towards desired derivatives.

Scheme 6

In Scheme 6 are outlined transformations of 10-carbonyl substituents into five- and six-membered heterocycles at C-10. Aryl derivatives are similarly prepared by ring forming reactions. In this case the products are drawn as heteroaryl derivatives 24 and 25. The reactions will in most cases run via a dihydro or even tetrahydro heterocycle that can be further oxidised and aromatised by standard methodology.

Scheme 7

An aldehyde or ketone in the 10-position as in structure 26 (Scheme 7) are suitable substrates for the introduction of alkenes by the family of Wittig reactions, or related reactions. Alternatively, the polarization in this reaction can be reversed in which case the bromomethyl substrate must be converted into an ylide for reactions with appropriate aldehydes and ketones to form the same alkenes 27. It will be recalled, however, that complete chemoselectivity was achieved for N-deoxygenation of the bromomethyl derivative 4 using tris (2-furyl)phosphine or triphenylphosphine (Scheme 1). Therefore ylide formation requires stronger reaction conditions or more reactive phosphines or phosphites.

Scheme 8

In another embodiment of the invention, heterosubstituents are substituted into the 10-methyl group shown in the case of the bromide 5 in Scheme 8. Structure 28 represents ether and sulfide derivatives that may be formed in reactions with the bromide 5 and metal olates or thiolates. Both alkyl and aryl derivatives become available in this manner. When the bromide 5 in a first step has been converted into an alcohol 18 in Scheme 5 or the corresponding thiol, the same products 28 are available by alkylation reactions.

The methyl ethers 29 would be important synthetic intermediates to provide compounds with a minimum of structural changes from the bioactive macrolides.

A convenient method for the preparation of 10-methylamino derivatives, is to react the bromide 4 or 5 with an amine. The amination can be run either with the free amine 5 or its N-oxide 4. In the reaction with benzylamine, the amine 5 was the substrate used to provide the benzylaminomethyl derivative 30. With p-chloroaniline in one experiment, the substrate was the N-oxide 4 which furnished the anilino derivative 31.

In order to provide 9-oxo derivatives, the 9-acetal function is to be opened under acidic conditions using catalysis. Due to high resistance towards the acidic conditions tried, indirect methods for acetal cleavage are also to be used.

Scheme 9

Scheme 9 outlines some reactions on saturation of the carbon-carbon double bond. After saturation, modified reactivity will be realized in chemical transformations at C-9. Besides catalytic hydrogenation, diboron addition can be used to provide the adduct 33. Substituted boron hydride reagents failed because of serious steric shielding. When the diboron adduct 33 was treated with a carboxylic acid, in this case acetic acid, C-protonation gave the product 34. Oxidation of the 3-hydroxy derivative 35 to its ketolide 36 can be effected by several reagents. A suitable process involves selective O-acetyl protection of the 2'-OH group. The macrolide aglycone hydroxy groups are less reactive for steric reasons. Oxidation of the sugar protected macrolide takes place selectively in the 3-position to furnish the corresponding 3-ketone. The acetyl protecting group is removed by methanol treatment with formation of the product 36.

Scheme 10

Erythromycin carries a hydroxy group at C-11. In the present case a hydroxy group at C-11 can be reintroduced by treatment of the diborane adduct 33 with hydrogen peroxide under alkaline conditions (Scheme 10). For steric reasons adduct formation is expected to occur from the less shielded alpha-face thereby providing a compound 37 with stereochemistry of the hydroxy group as in erythromycin. A large excess of the oxidising agent is used in generating the alcohol. Concurrent oxidation of the amino group therefore occurs. The resultant N-oxide, however, is readily and cleanly deoxygenated on treatment of the product with triphenylphosphine, the product being structure 37.

In the subsequent reaction, the acetal function at C-9 has to be cleaved and the 3-OH group oxidised to its ketone 39 as outlined in Scheme 10.

Scheme 11

In an alternative oxygen insertion reaction, epoxide formation was successfully achieved using m-chloroperbenzoic acid as shown in Scheme 11. The product is the N-oxidised structure 40. N-Deoxygenation occurred readily by heating the latter with triphenylphosphine at reflux temperature in THF. The product was the amine epoxide 41. In the subsequent reaction step, the epoxide 40 can be rearranged to the 11-ketone 42 by Lewis acid catalysis or under the influence of palladium catalysis and reflux conditions in toluene. Various catalytic hydrogenation procedures or metal hydrides can be used to reduce the 11-keto function to a hydroxy group. The choice of reducing conditions will determine the prevalent hydroxy epimer being formed. Cleavage of the 9-acetal and oxidation of the 3-hydroxy group are the next steps to be carried out as above.

Alternatively, hydrolytic cleavage of the 9-acetal function can be carried out at the level of the 11-ketone 42 before reductions.

Scheme 12

Macrolides based on an oxime function in the 9-position have been commercialised. A classical synthesis of analogues based on the intermediate substrate 45 is outlined in Scheme 12. Oxime formation by treatment with hydroxylamine provides the oxime 46. The oxime oxygen is alkylated under strongly basic conditions to provide the O-alkyl oxime 47. A subsequent oxidation as carried out above, provides the desired 3-ketolide 48.

Scheme 13

Scheme 13 gives an outline of the preparation of 9-oxo-6-OMe-3-ketolides 52. The 9-oxime is protected by reactions as above leading to the O-protected oxime 49. The 6-OH group can be O-methylated under strongly basic conditions to furnish the 6-methoxy derivative 50. Subsequently, the oxime function is removed (vide infra) to furnish the 9-oxo derivative 51. A subsequent oxidation provides the 3-ketolide 52 as a target compound.

Scheme 14

A more detailed synthesis of a 6-O alkyl derivative 59 is outlined in Scheme 14. Oximation under standard conditions provides the substrate 53 which is protected as an oxime mixed acetal 54 under experimental conditions related to published methodology. This substrate is allylated under strongly alkaline conditions as shown in Scheme 14. The product is the 6-allyloxy derivative 55. Subsequently, the oxime protecting function is removed. In the first step, cleavage of the acetal function is effected by acetic acid to furnish the oxime 56. The N—O bond is cleaved by bisulfite-formic acid and the resultant imine hydrolysed by aqueous ethanol at elevated temperature to furnish the 9-ketone 57. Before the oxidation of the 3-hydroxy function, the sugar 2'-hydroxy group has to be protected, in this case by selective acetylation. The oxidation can be effected by several methods including the Corey-Kim oxidation, the Dess-Martin oxidation, Jones oxidation and the Pfitzner-Moffat oxidation to furnish the 3-ketolide 58. The Corey-Kim oxidation is shown in Scheme 13. Among other methods, substitution in the allylic moiety can be effected under Heck conditions to furnish target compounds 59.

Scheme 15

The same oxime protection has also been used in reported 6-O methylation work. In clarithromycin work strongly basic solution of aqueous KOH was used. In Scheme 15 this is shown for a transformation of structure 54 to its 6-methoxy derivative 60. Subsequently, the oxime protection is removed as discussed in Scheme 14.

Scheme 16

Scheme 16 shows oxime protection by analogy to literature for the preparation of clarithromycin. The oxime oxygen in substrate 46 is alkylated by 2-chlorobenzyl chloride to furnish structure 62. TMS-protection is used for the 2'-hydroxyl group in the sugar and in the 3-position, structure 63. 6-O-Methylation is effected by methyl iodide in DMSO-THF with sodium hydroxide as base. The product will be the 6-methoxy derivative 64. Removal of the benzyl function by hydrogenolysis over palladium on charcoal provides the oxime 61® Reductive hydrolysis as above yields the 9-ketone 65. Protection of 3-OH is by an acetyl function as in structure 66. Oxidation of 3-OH and acetyl removal by methanol is effected with the same procedure as above. The product is the ketolide 66a.

Scheme 17

2-Substituted ketolides are potentially useful analogues, in particular 2-halogen derivatives with emphasis on 2-fluoro derivatives. Fluorine can be introduced by an electrophilic substitution on an enolate of the ketolide. The reaction is exemplified by the series shown in Scheme 17, but the fluorination can also be carried out at later steps in a reaction sequence.

Scheme 18

Several ketolide drug candidates are 11,12-cyclic carbamates. The present invention also includes cyclic carbamate structures. One such preparation starts with structure 70 in Scheme 18. Reaction with carbonyldiimidazole leads to the carbonyl activated urethane 71. The latter, when reacted with an amine or ammonia forms an 11,12 cyclic carbamate 72. When the Nsubstituent is hydrogen, N-alkylation reactions under basic conditions will provide derivatives of the type alkyl-heteroaryl. Alternatively, the side-chain is anchored to the amino nitrogen before it is involved in cyclic carbamate formation to furnish structures 72.

In another series, the amino nitrogen is part of a hydrazine structure or hydrazine itself as shown in the formation of the hydrazide 73 in Scheme 18. A subsequent cyclisation provides the 11,12-cyclic carbazate 74, probably as a mixture of epimers at C-10. Epimerisation to the natural configuration can take place under the basic conditions caused by excess of hydrazine. The hydrazone 75 is probably an intermediate in a subsequent reductive alkylation with sodium cyanoborohydride and an aldehyde corresponding to the desired side-chain product 76.

Scheme 19

In Scheme 19 substrate 77 is available by a Stille coupling or a Sonogashira coupling between one of the 10-bromomethyl substrates and a terminal alkyne. In a reaction with palladium diacetate together with triphenylphosphine, initial adduct formation over the triple bond leads to intermediate 78. A Pd-effected cyclisation reaction subsequently occurs. The hydridopalladium elimination from the cyclisation adduct requires a cis-arrangement of the outgoing substituents which means that double bond isomer 79 is expected. In this manner phamacophoric groups, as in the new ketolides, may be anchored through the new ring structure to the macrolide. The annulation may also affect the conformational preferences of the macrolide ring in a manner that facilitates hydrolytic cleavage of the acetal. In an atmosphere of carbon monoxide, CO insertion leads to annulated six-membered ring derivatives indicated by structure 80, or in its more stable phenolic form 81.

A bromomethyl substrate can also be made to react with a geminal diheterofunctional-$C_1$ reagent. Such reagents could be thiourea or its equivalents, urea or its equivalents, guanidins or its equivalents as indicated in Scheme 20. Of special interest are reagents derived from amidine that will provide annulated pyrimidine derivatives 88 carrying a pyrimidine 2-substituent for additional manipulations.

With thiourea substitution at the bromomethyl carbon by the sulfur is to be expected. The initially formed onium salt 84 can then react further by attack at the acetal carbon with structure 85 as an intermediate. The opening could also take another course resulting in liberation of the 6-hydroxy group (not drawn). In structure 87 both hydroxy groups have been set free. When an amidine was used instead, the annulated dihydropyrimidine 88 would be provided.

If the initial cyclisation instead takes place over the double bond, structure 84 would be the initial product—

Scheme 21

When the reagent is a hydroxylamine or hydrazine, five-membered heterocycles can be formed. Scheme 21 shows some reactions using reagents derived from hydroxylamine. Oxygen has been introduced at the allylic carbon in structure 89. The nitrogen must be protected for the oxygen to be the nucleophile. An appropriate reagent in this case is an aldoxime. Mild acid hydrolysis will furnish the aminoxy derivative 90. Cyclisation under acid catalysis takes place towards the acetal carbon with formation of the cyclic oxime 91 that is an annulated dihydroisoxazole derivative. If desirable, the latter is readily cleaved by hydrogenolysis to provide the hydroxymethyl derivative 92.

Scheme 22

When the cyclisation takes place over the carbon-carbon double bond, a tetrahydroisoxazole 93 is obtained as in Scheme 22. The isoxazole can be cleaved by hydrogenolysis, or as shown, be N-alkylated as in structure 94. Further manipulations are indicated from structures 95.

Scheme 23

Similar reactions with hydrazines are shown in Scheme 23. Allylic N-alkylation provides structure 96. Acid catalysed cyclic hydrazone formation at the acetal carbon is expected to furnish the dihydropyrrazole derivative 97. The latter can be further manipulated starting by an N-alkylation reaction to provide structure 98. Hydrogenolysis can be used to cleave the nitrogen-nitrogen bond as in structure 99.

Scheme 24

In Scheme 24 cyclisation over the carbon-carbon double bond is shown to lead to the tetrahydropyrrazole 101 that can be further manipulated as indicated in structures 102 and 103.

Scheme 25

Starting with a macrolide 104 in which the 6-hydroxy group is protected and which has 10-methyl and 11-hydroxy substitution, water is eliminated creating a 10-11 double bond by reaction with ethyl carbonate. The product is then transformed into the corresponding 3 hydroxy macrolide 105 by acidic hydrolysis. Chemoselective N-oxidation of the 10,11-anhydro substrate 105 was carried out using $H_2O_2$ as the oxidising agent in methanol at room temperature. The product was the desired N-oxide 106 in high yield. The N-oxide moiety can be regarded as a protected form of the tertiary amino group for a subsequent chemoselective reaction in the 10-methyl group. The bromination was effected by NBS in acetic acid at room temperature. When bromination was attempted with the amine 105 without the protection by the N-oxide function, several products were formed. In the 6-O-methyl derivative 106 the product was the corresponding 10-acyloxymethyl derivative 107. The product formation may be rationalised as an initial bromination followed by fast solvolysis, in this case with acetic acid, to furnish the allylic acetate 107. Deprotection with removal of the N-oxide function was effected by triphenylphosphine under reflux in THF. The product was the 10-acetoxymethyl amine 108. For some of the subsequent reactions the reactive hydroxyl in the sugar moiety was protected. Acetyl protection was effected with acetic anhydride in the presence of triethylamine to provide the 2'-O-acetyl derivative 109. Oxidation of the 3-OH group to furnish the ketolide 110 was effected with periodinane under Dess-Martin conditions. Removal of the O-acetyl function in the 2'-position readily takes place in methanol with formation of the 10-acetoxymethyl derivative 111.

Scheme 26

The allylic acetate 111 was deacetylated with sodium methoxide in methanol. The methanolysis could be effected without heating at room temperature. Under these conditions the reaction was slow but gave a satisfactory high yield of the allylic alcohol 112.

Scheme 27

Scheme 3 shows methodology for the preparation of 11,12-annulated cyclic urethanes. In this case the original methyl group has been modified into a methylene group, structure 115. The appropriately protected substrate 111 was metallated using NaHMDS at −40° C. and treated with carbonyldiimidazole (CDI). The product was the imidazolocarbonyl derivative 113. With aqueous ammonia the latter reacts to form the oxazolidinone product 114. This is a novel, unique reaction in that it also involves a concurrent elimination of acetic acid and formation of the 10-methylene function in structure 114. Methanolysis was used to remove the acetyl group in the sugar protected derivative 114 with formation of target ketolide compound 115.

Scheme 28

In Scheme 27 ammonia was used to effect the concurrent annulation reaction and methylene generation. When a primary amine is used as the amine substrate, an N-substituted annulated ring results. The reaction is illustrated with benzylamine when the N-benzyl derivative 116a is obtained. Other alkylamines react similarly. Of special interest is the 4-phenylbutane derivative 116b. Removal of the acetyl protecting group in the sugar moiety is readily effected by methanolysis as demonstrated for the preparation of the sugar hydroxy compound 117.

Scheme 29

The methylene group in the novel structure 115 is part of an a,b-unsaturated carbonyl system. Such a substrate can be used both for Michael additions and for Heck coupling reactions. In Scheme 29, Michael additions with benzylamine and with 3-phenylpropane-1-amine are shown. The products 118a and 118b are 10-methylamino derivatives. Other substitutions on the amino nitrogen may also be used to introduce pharmacophoric functions similar to those attached to the 11'N-position in known macrolides.

Scheme 30

In Scheme 30 a bifunctional amine reagent, ethane-1,2-diamine, is used. The reaction is rationalised as an initial aminolysis of the imidazolo carbonyl group followed by addition and cyclic carbamate formation. Acetate elimination occurs concurrent with the cyclisation generating the methylene function. The second amino group becomes attached in a Michael fashion to the methylene carbon. Thereby cyclisation occurs with formation of the product 119.

Scheme 31

Scheme 31 shows an example of substitution at the allylic carbon in the acetoxy derivative 109. Chemoselective attack with sodium azide occurred at the allylic carbon, the product being the azidomethyl derivative 120. Protection of the 2'-OH group was effected with acetic anhydride as reagent to form the acetoxy derivative 121. A subsequent Dess-Martin periodinane oxidation provided the 3-ketolide 122 which is metallated and acylated by CDI to form the imidazolocarbonyl derivative 123. As an intermediate as such or after prior conversion to amino functions for further reactions towards target compounds.

Scheme 32

Carbylations in the allylic acetate moiety can be effected with transition metal catalysis. The methodology is exemplified with a methylation reaction shown in Scheme 32. The methodology requires a fully protected substrate. In the present case persilylation has been used. BSTFA is a mild reagent for introduction of trimethylsilyl groups and provided the persilylated structure 124. The carbylation was effected with trimethylaluminium and palladium catalysis resulting in formation of the 10-ethyl derivative 125. In this manner the methyl group in the original substrate can be converted into larger carbon substituents. In the present series, the silyl protecting groups are removed with fluoride ions in form of the TBAF reagent to yield the deprotected ethyl derivative 126. For further applications the latter can be protected in the sugar moiety as a 2'O-benzoyl derivative 127 using benzoic anhydride and is subsequently converted into the 3-ketolide 128 by Dess-Martin periodinane oxidation.

Scheme 33

Another example of carbylation is provided by the reaction of the substrate 109 with the tributyltin derivative of phenylacetylene under Pd-catalysis. The product was the 10-propyne derivative 129. The product, even without any protection of the substrate 109, was isolated in 33% yield.

Scheme 34

Scheme 34 shows a conversion of the 10-ethyl derivative 126 into its oxazolidinone derivative 134. With acetic anhydride the reactive hydroxyl group in the sugar moiety is protected, structure 130. Dess-Martin oxidation provides the 3-ketolide 131 which is subsequently metallated and acylated using CDI with formation of the imidazolocarbonyl derivative 132. Aqueous ammonia leads to oxazolidinone formation and derivative 133 from which deacetylation to compound 134 is effected by methanolysis.

Scheme 35

Carbazate analogues, or N11-amino derivatives, are available by the reaction of hydrazine or a substituted hydrazine with intermediate 12'O-imidazolocarbonyl derivatives. Scheme 35 shows a reaction between the imidazolocarbonyl derivative 135 and excess hydrazine hydrate which provides the 3-aminoxazolidinone derivative 136. Reductive alkylation between the amino group and a heterocyclic aldehyde with sodium cyanoborate provides an alkylated product such as structure 137. The benzoyl protection in the sugar moiety is removed by methanolysis to provide target compound 138.

Scheme 36

A scheme for the preparation of some compounds of the final target families is shown in Scheme 36. For the preparation of the 4-[4-(3-pyridinyl)imidazolyl]butyl derivative 140 the substrate is the sugar protected ethyl 3-ketolide 128. Metallation and a subsequent reaction with CDI provides the imidazolocarbonyl derivative 135 which is reacted with a butylamine substituted at the terminal carbon by a heterocycle, in this case by 4-(3-pyridinyl)imidazole, in aqueous acetonitrile at elevated temperature. The product is the N-substituted oxazolidinone 139. The target compound 140 is available by removal of the benzoyl protection in the sugar moiety by methanolysis. In an alternative approach compounds of this family can be prepared by an alkylation reaction on a preformed oxazolidinone derivative such as structure 133 in Scheme 34.

Scheme 37

In Scheme 37 is indicated a route for the preparation of the cethromycin family analogs which carry new substituents in the 10 position. A route to a key allylic acetate intermediate 146 is shown. The starting material is the 06-allyl derivative 141 which has been described in patents and other publications. To avoid any interference from the double bond in the allylic moiety in the oxidation step, and in the bromination reaction, the double bond is initially protected as a dibromide. Thereafter a series of reactions follow the standard methodology set out herein until the allyl group can be regenerated. Several methods exist for the vicinal debromination, e.g. by zinc or by the iodide ion. In the latter case triphenylphosphine is used for deoxygenation of the N-oxide. In the former case the metal reaction is assumed to include deoxygenation. Intermediate 146 is subsequently modified on the allylic carbon for the desired target compound and reacted further by analogy to literature.

Transformations at C-10

From 10-AcOCH$_2$—: A number of transformations have been given above, e.g. hydrolysis, carbylations, amination.

10-CH$_2$═: In Scheme 29 is demonstrated amination of the double bond in the α,β-unsaturated carbonyl structure 115 by a Michael addition. The Michael addition proceeds readily with thiol reactants to form thioethers. Alcohols will also be Michael reactants providing corresponding ethers. For carbylation reactions, Heck coupling conditions are used, e.g. in introduction of aryl or heteroaryl substituents at the methylene carbon. The Heck products can be taken further to target molecules with or without saturation of the double C—C bond.

CH$_2$N$_3$: An azide function is a common intermediate function in the synthesis of amines. Reductive procedures are used. Examples shown include hydrogenolysis over Pd/C, or use of certain types of Raney-Ni. Convenient is also the use of low-valent metals, several examples exist. A good reagent is SnCl$_2$ which will provide a primary amine.

The 10-HOCH$_2$— group can be transformed by gentle oxidation to a 10-CHO group which in turn can be oxidized to the 10-carboxylic acid which can, if desired be transformed to an amide or ester, optionally one having a pendant aryl-(or heteroaryl)-alkyl group.

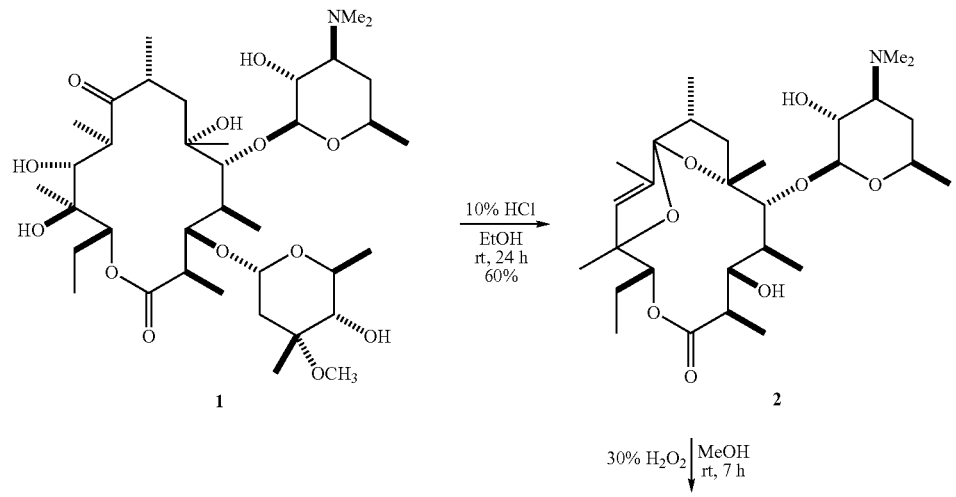

-continued
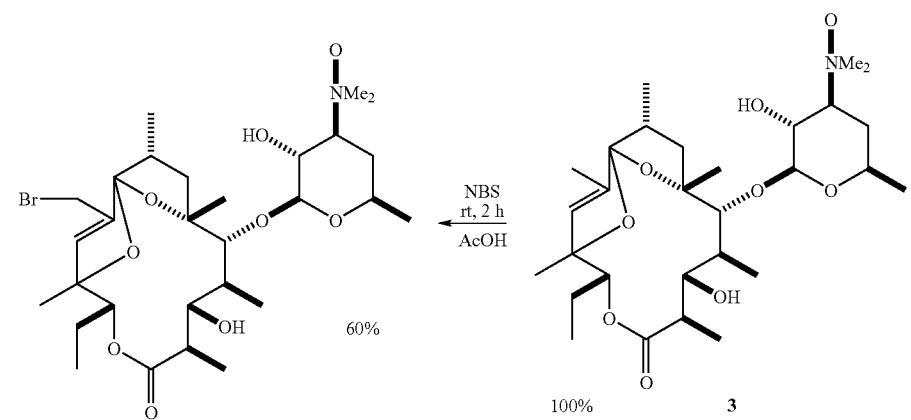
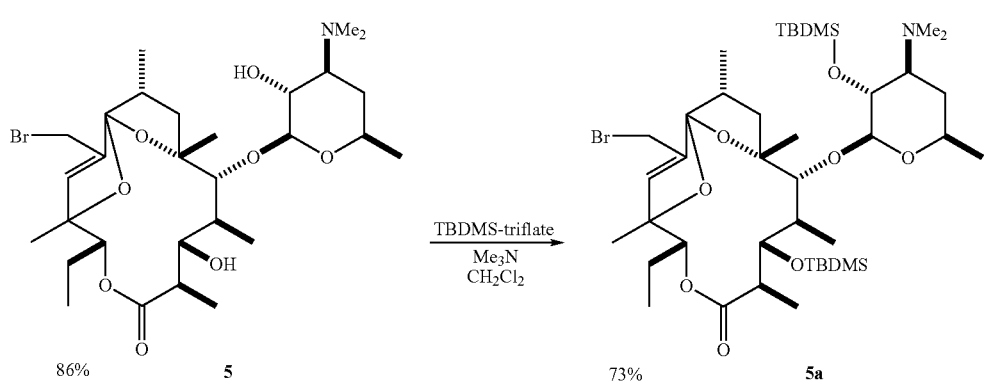
Scheme 2
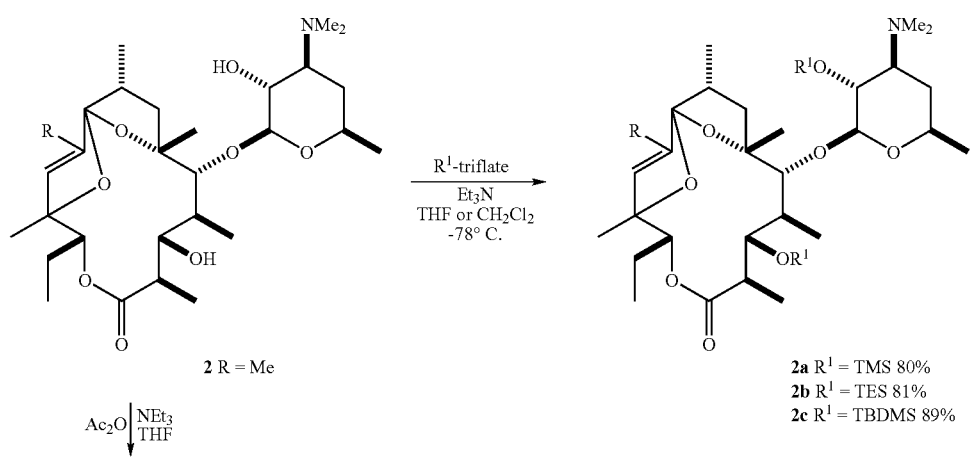

-continued
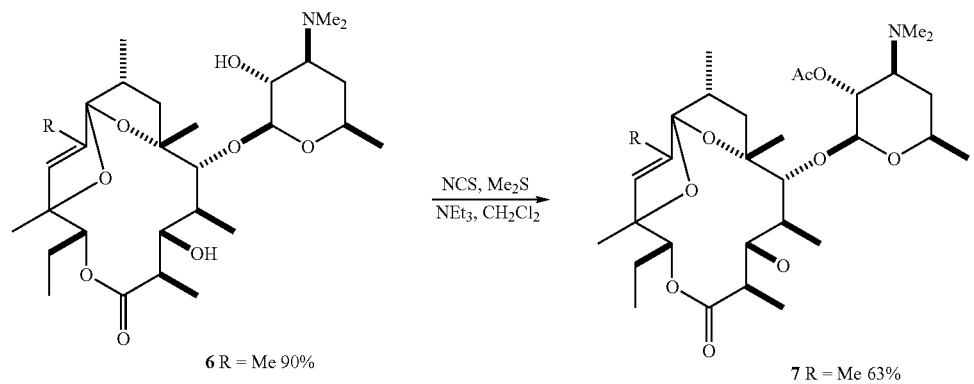
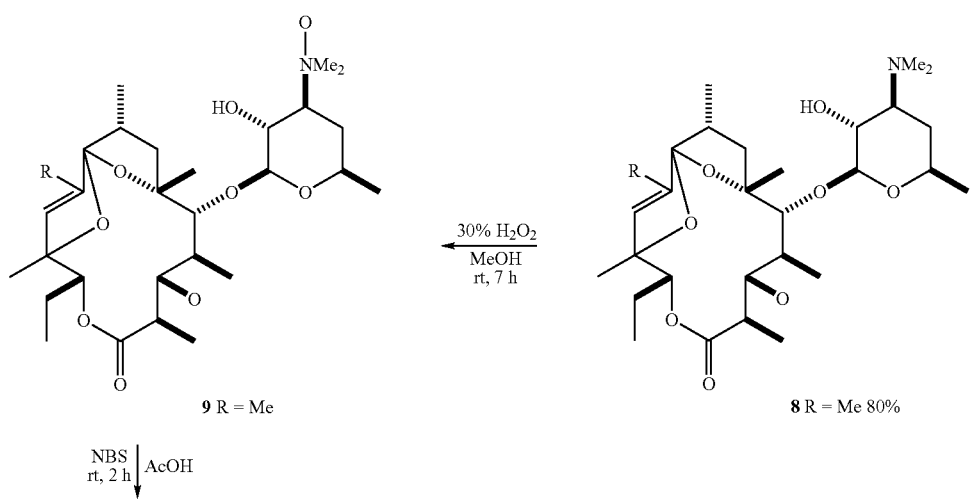
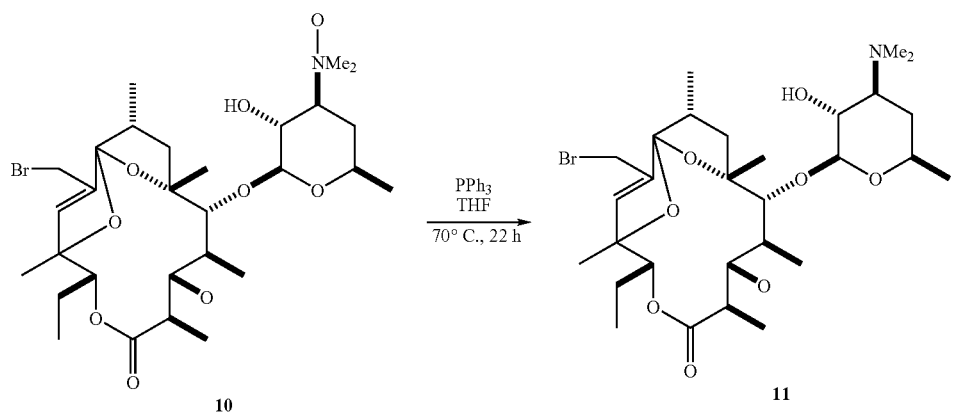

Scheme 3
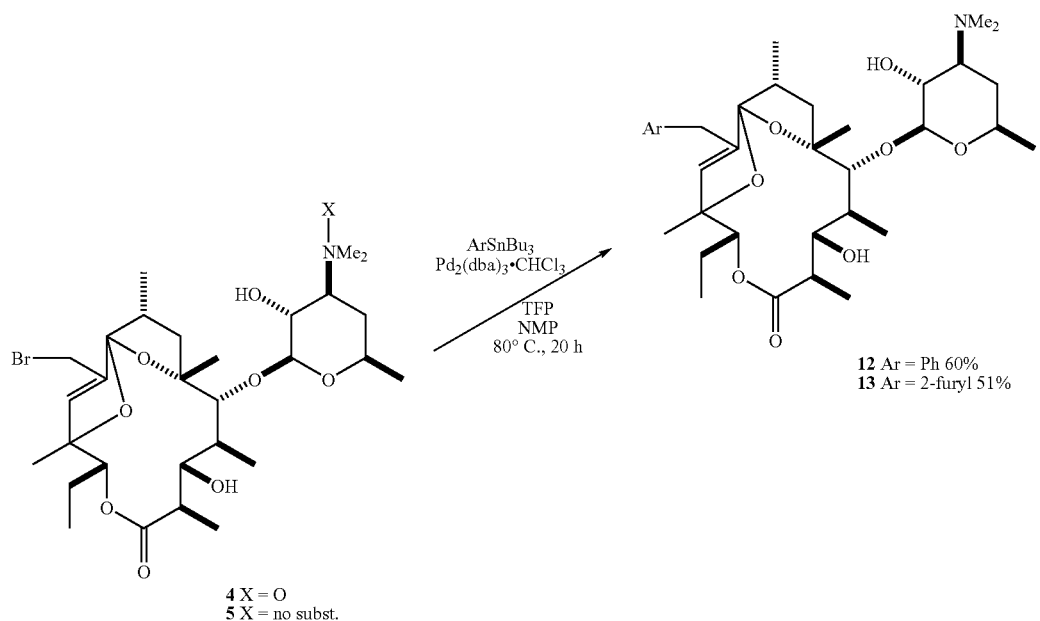
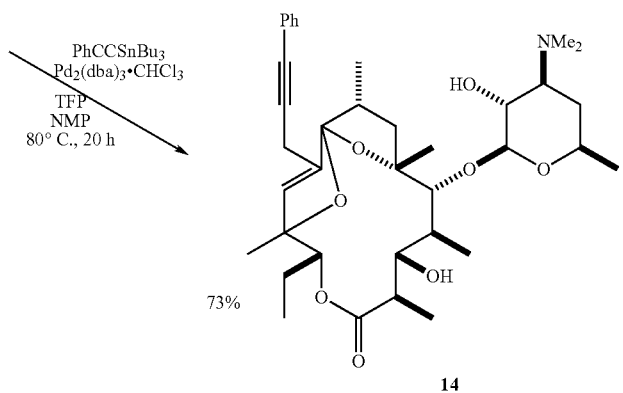
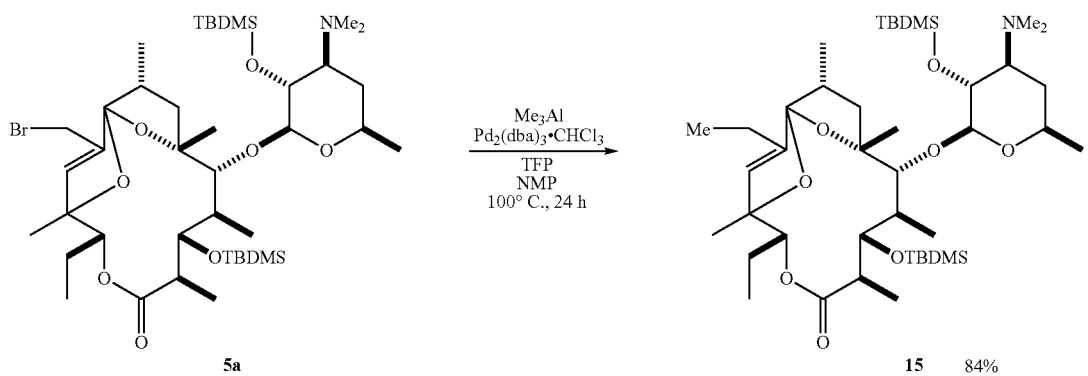

Scheme 4
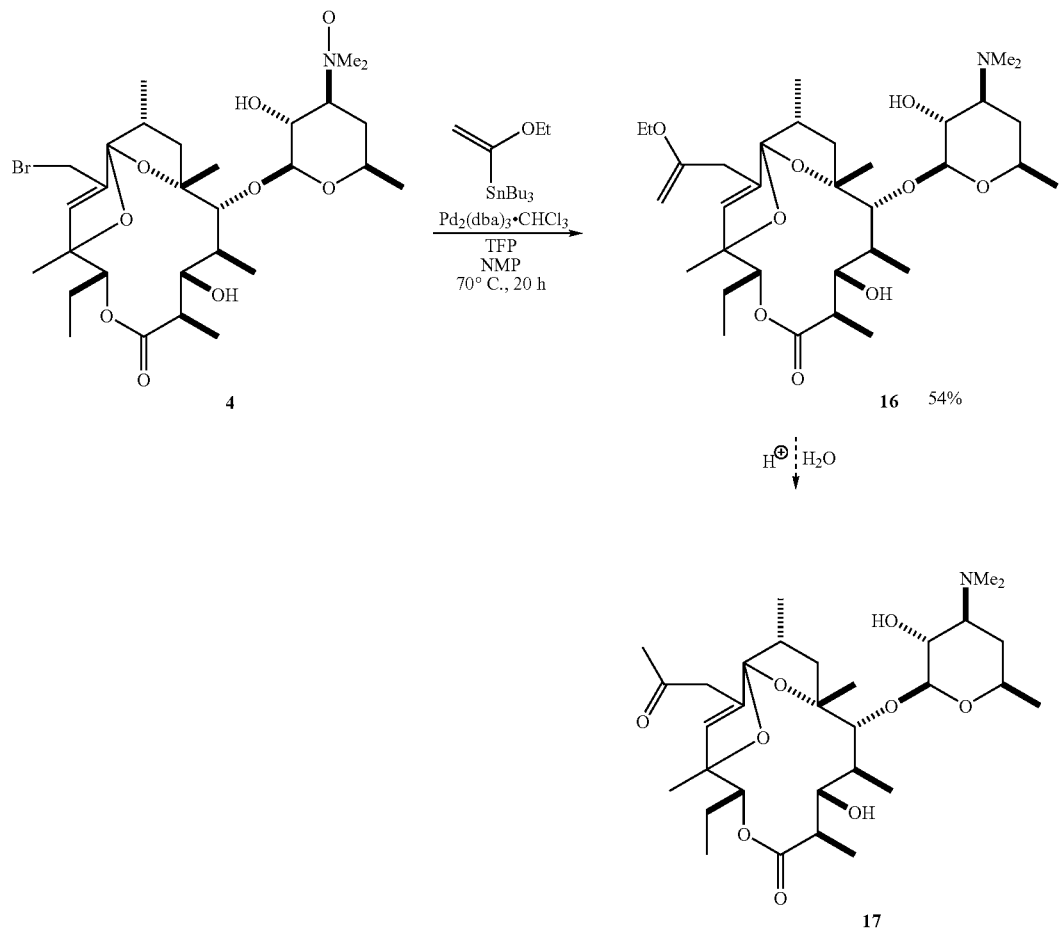
Scheme 5
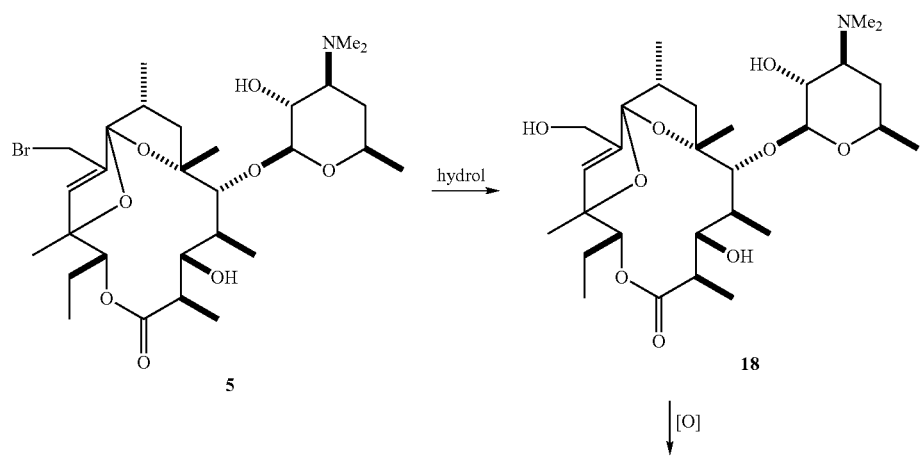

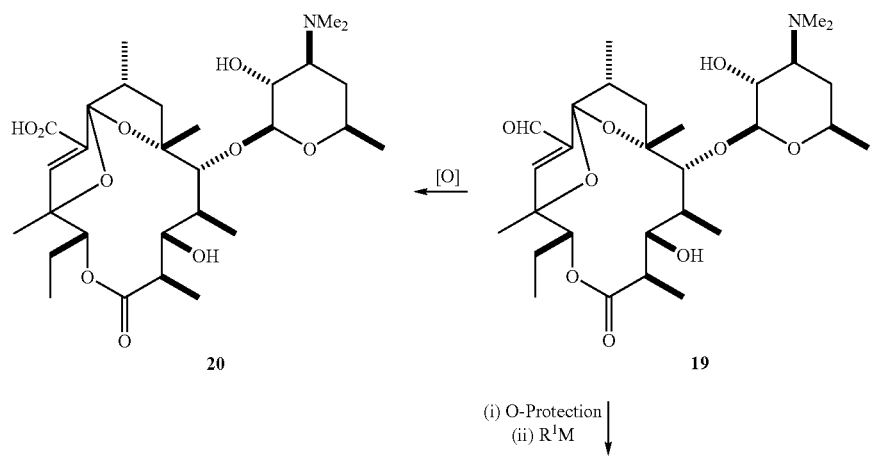
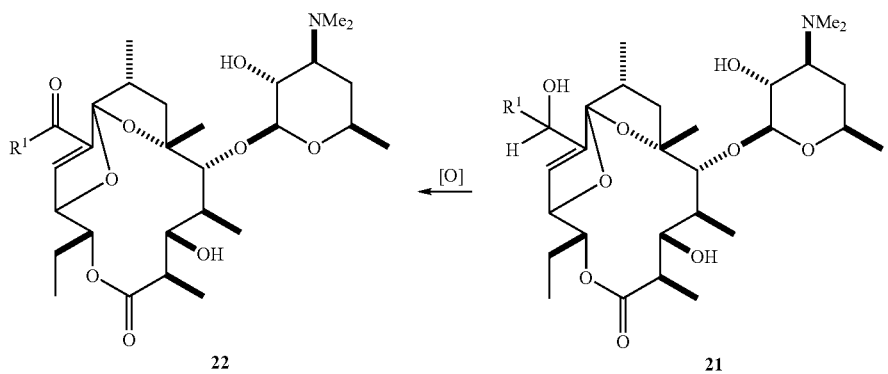
Scheme 6
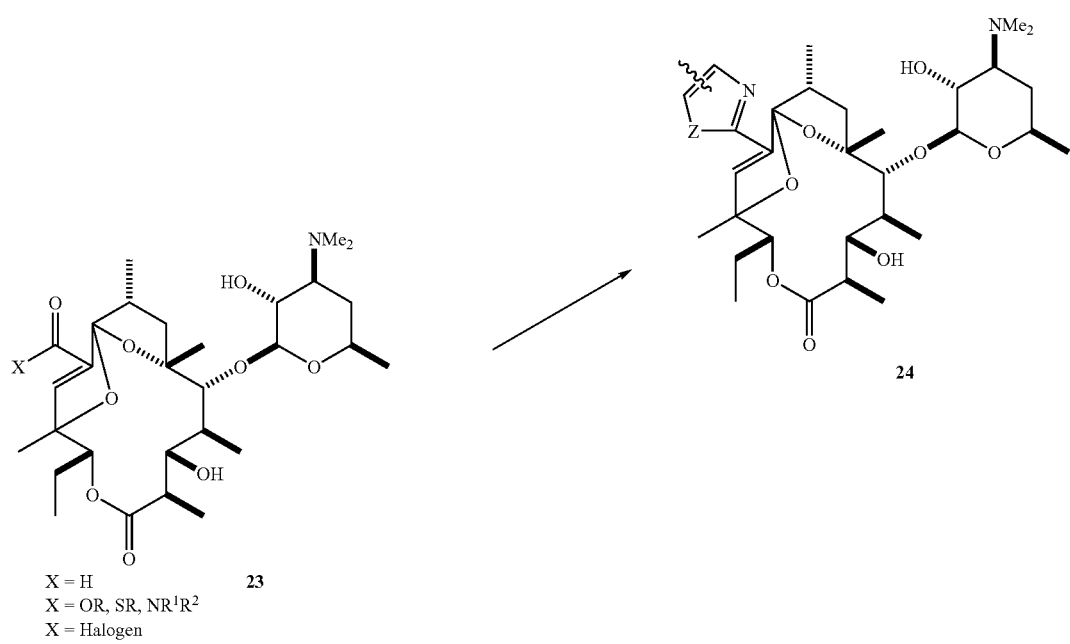
X = H  
X = OR, SR, NR¹R²  
X = Halogen

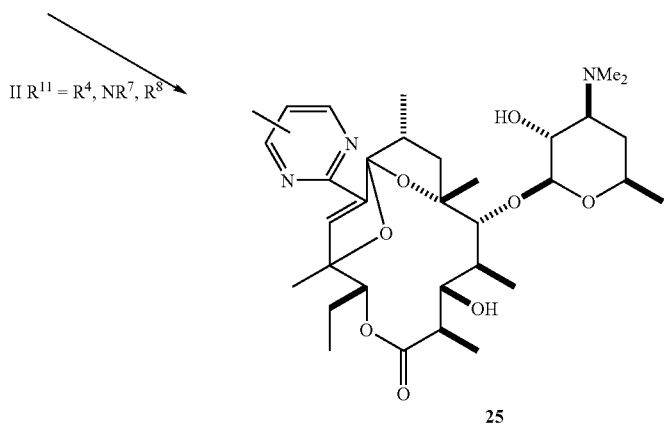
Scheme 7
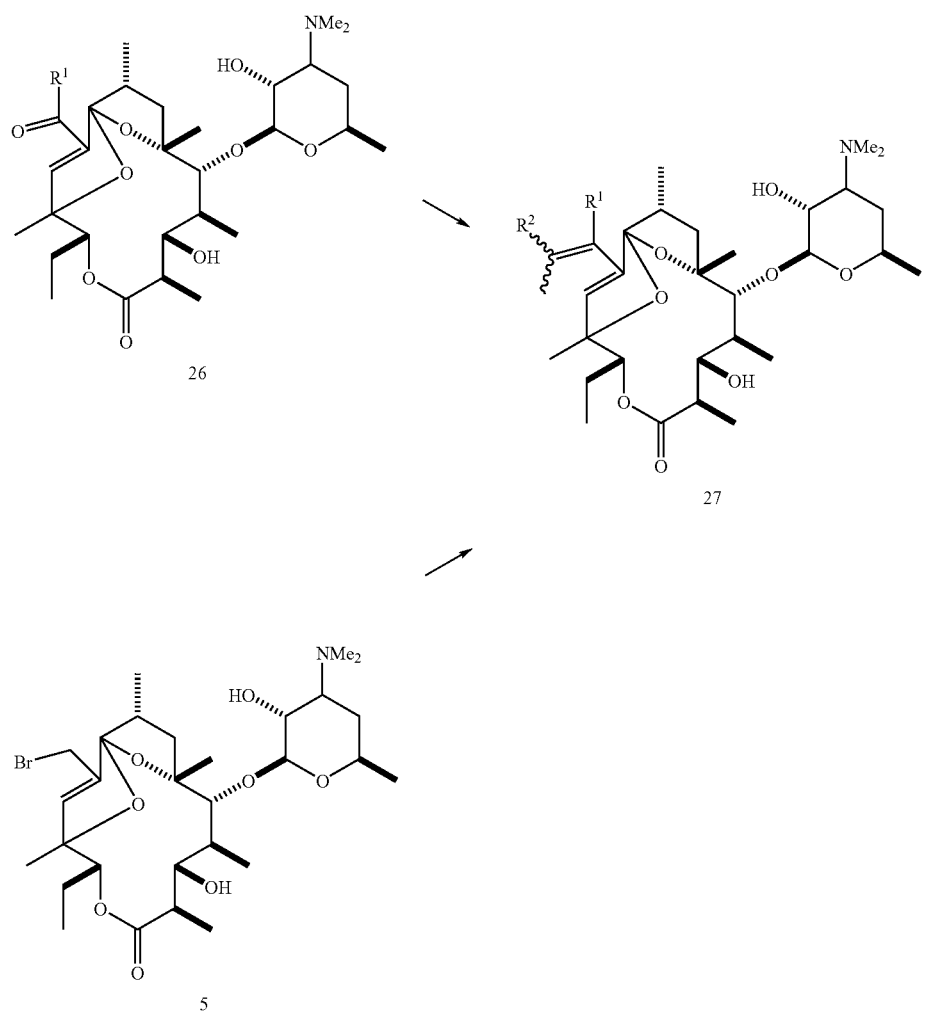

Scheme 8
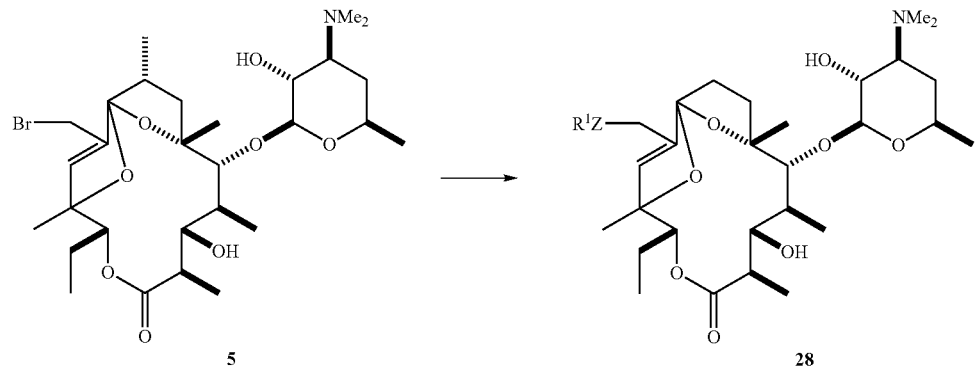
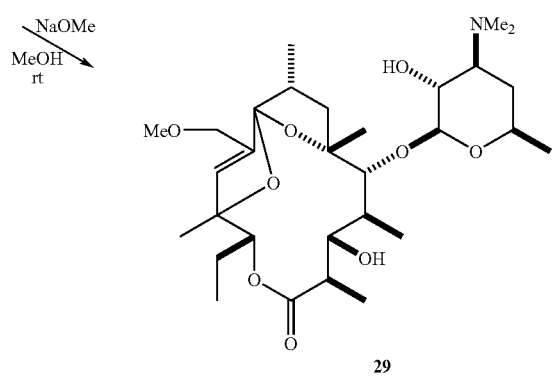
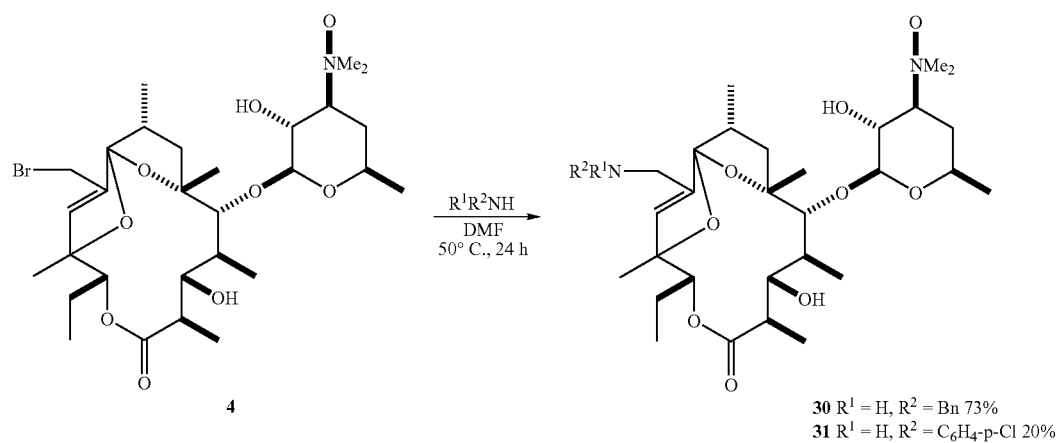

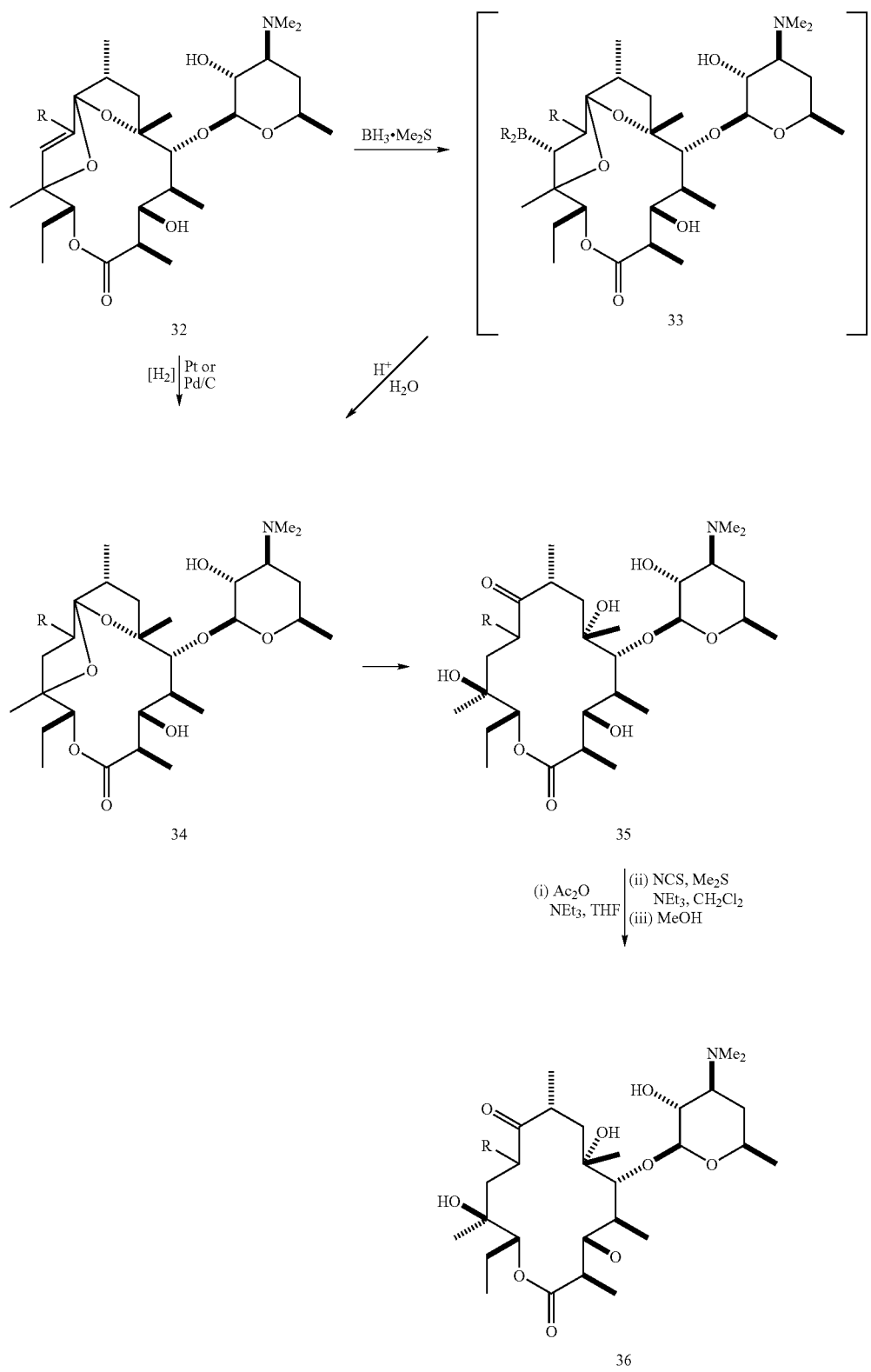
Scheme 9

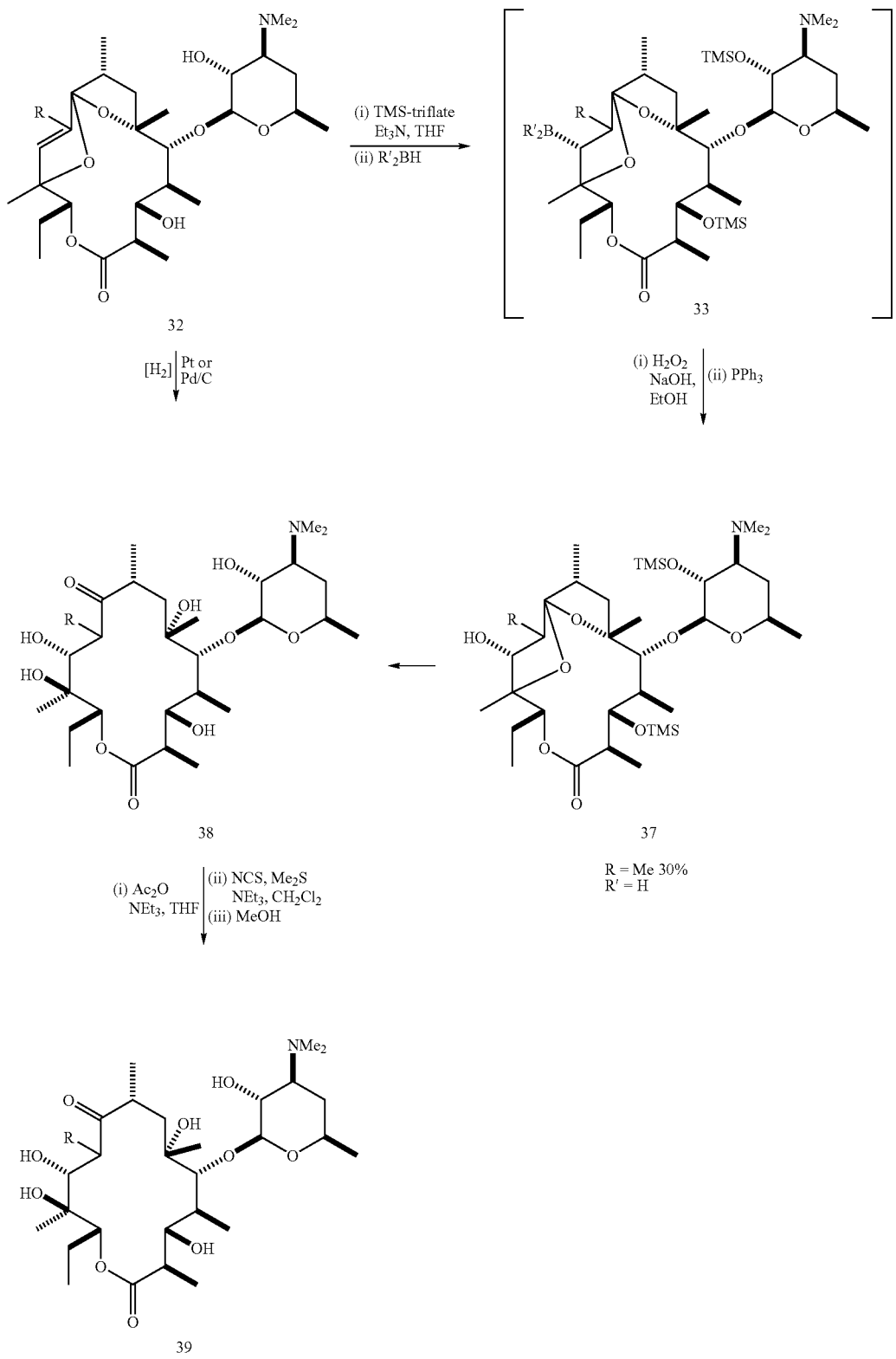

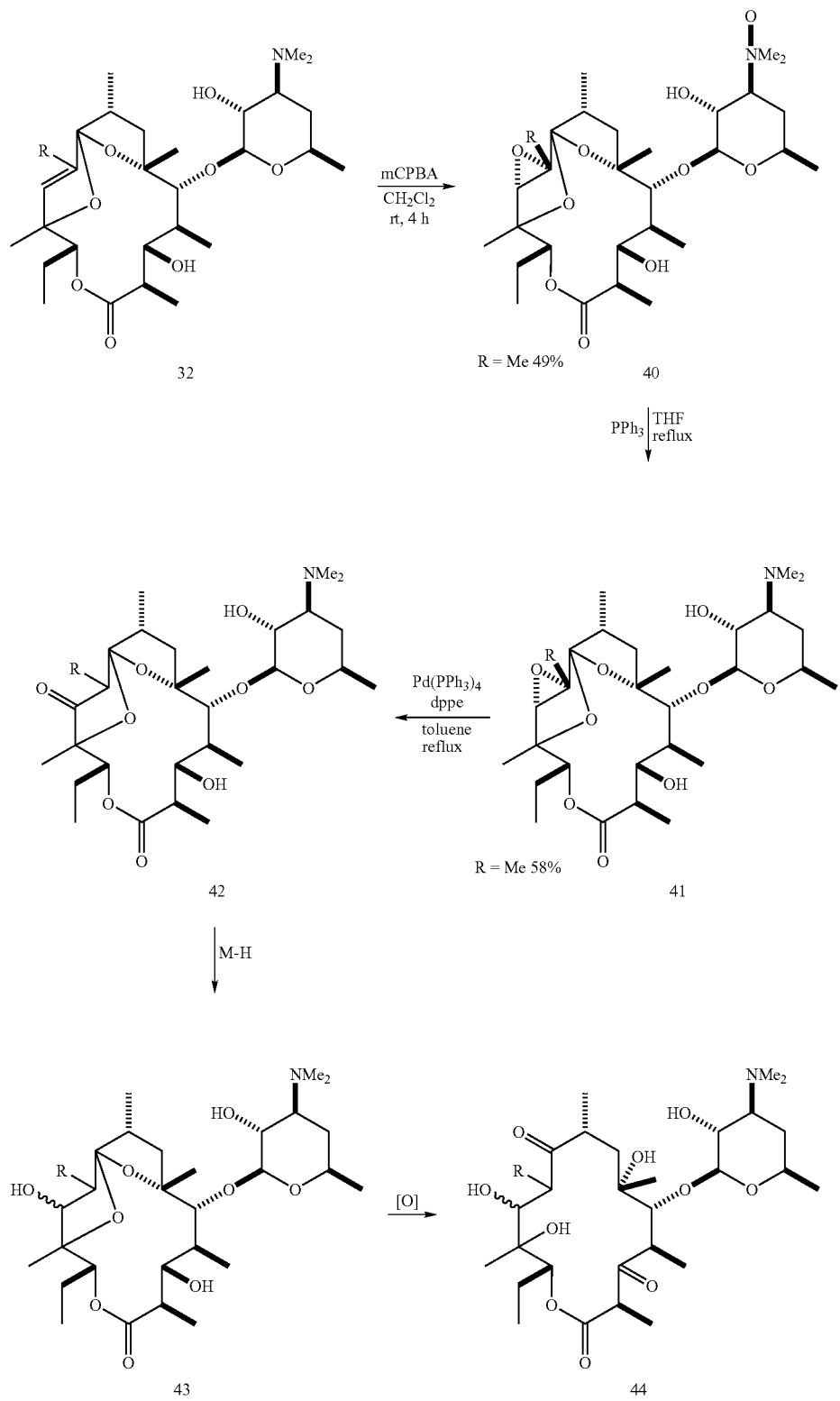

Scheme 12
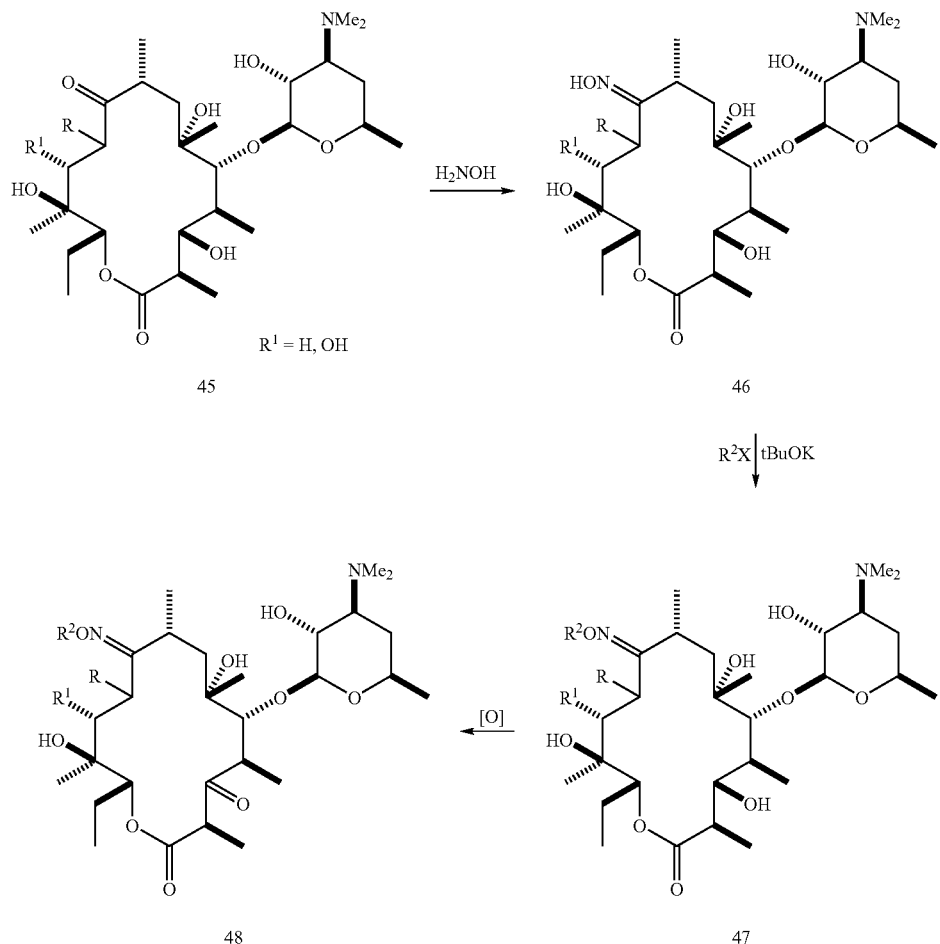
Scheme 13
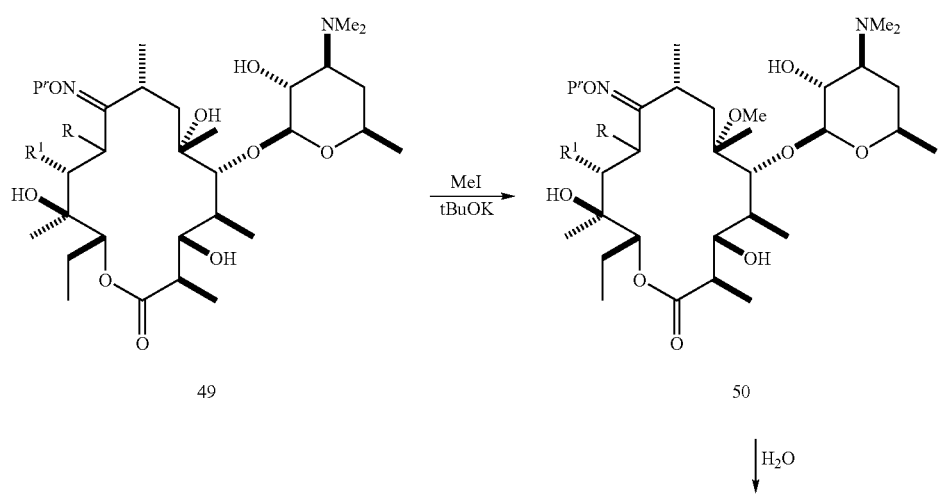

-continued
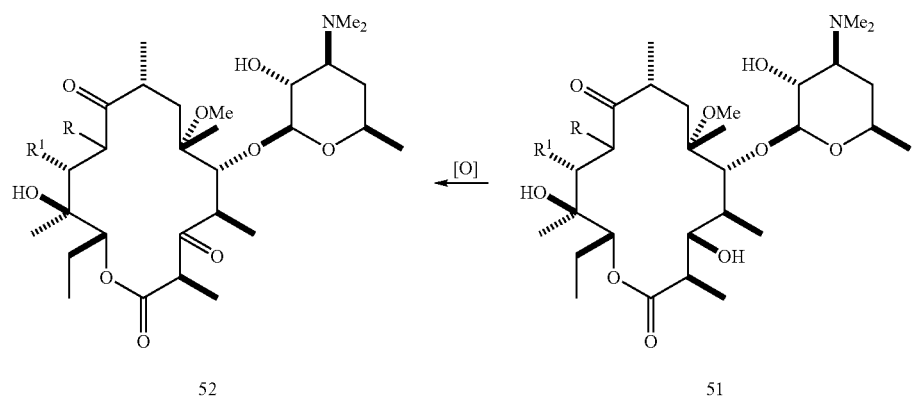
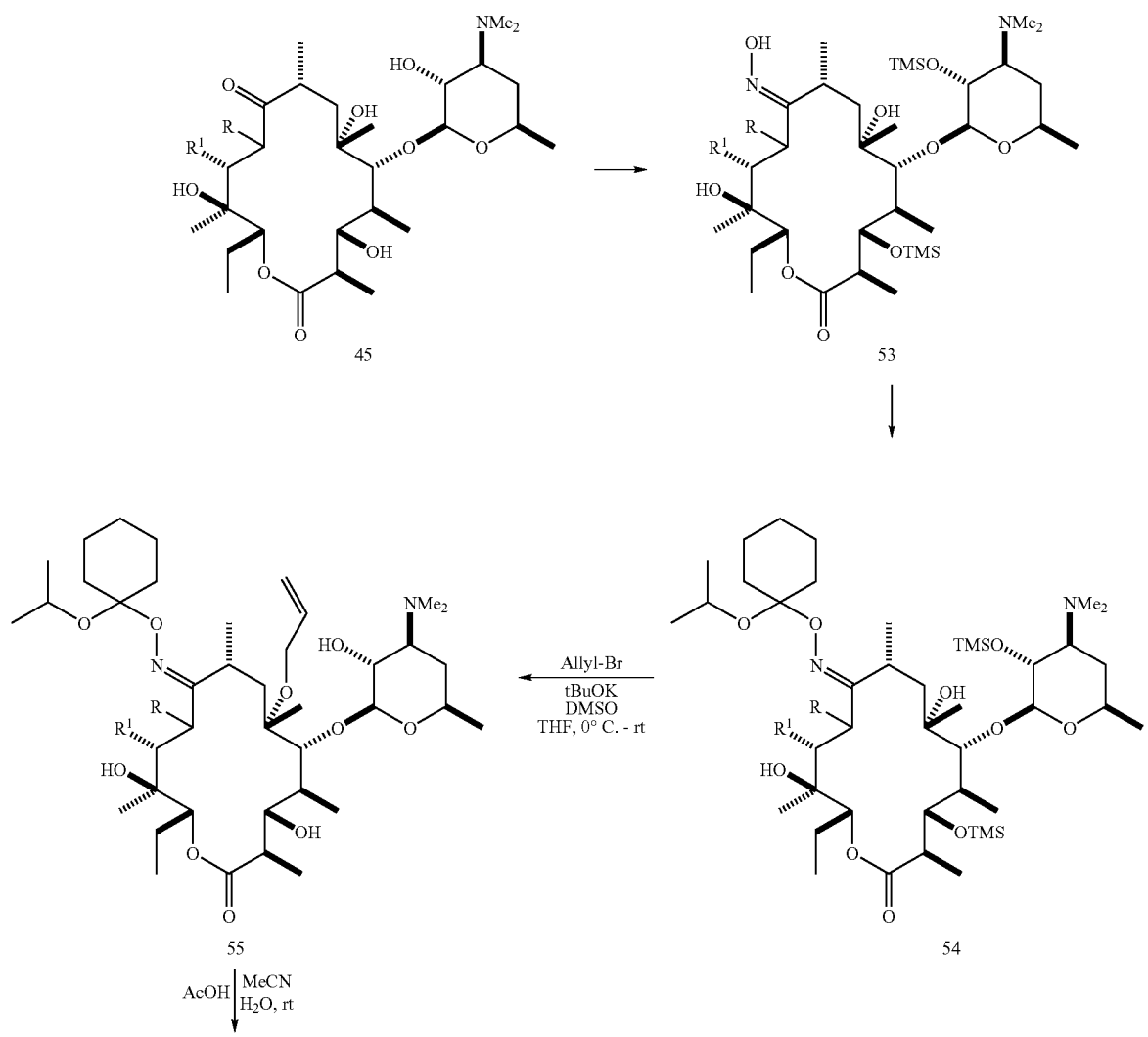

-continued
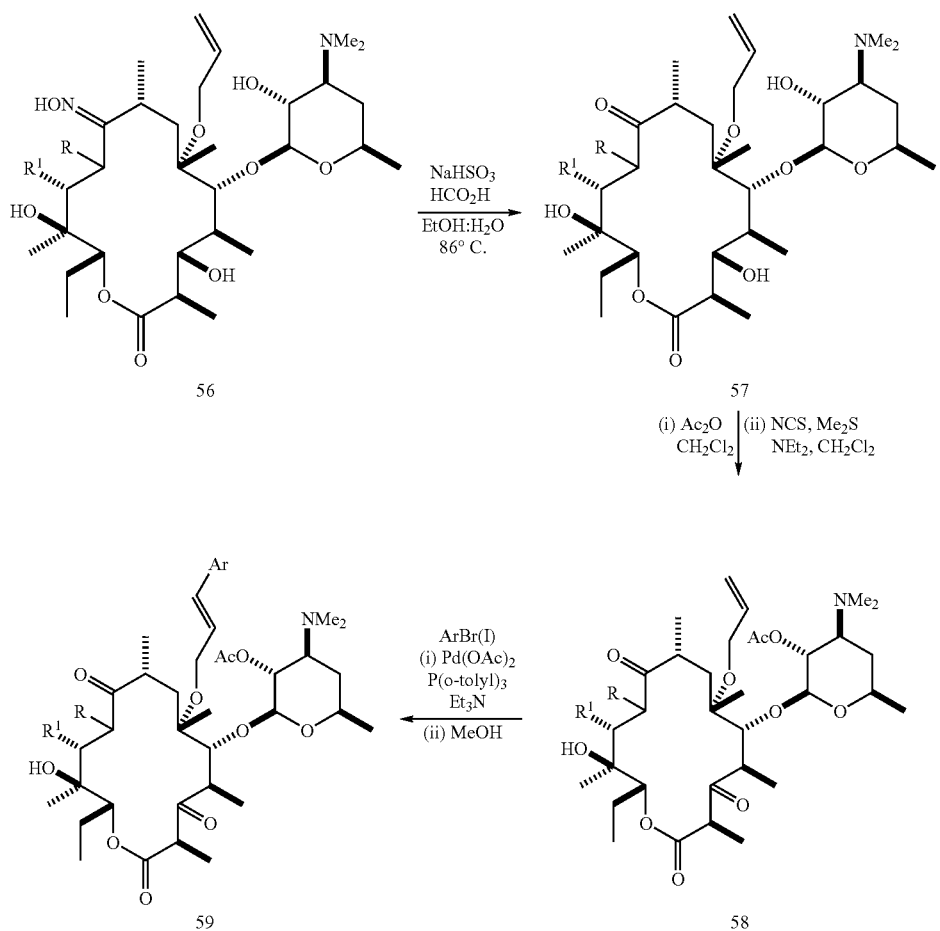
Scheme 15
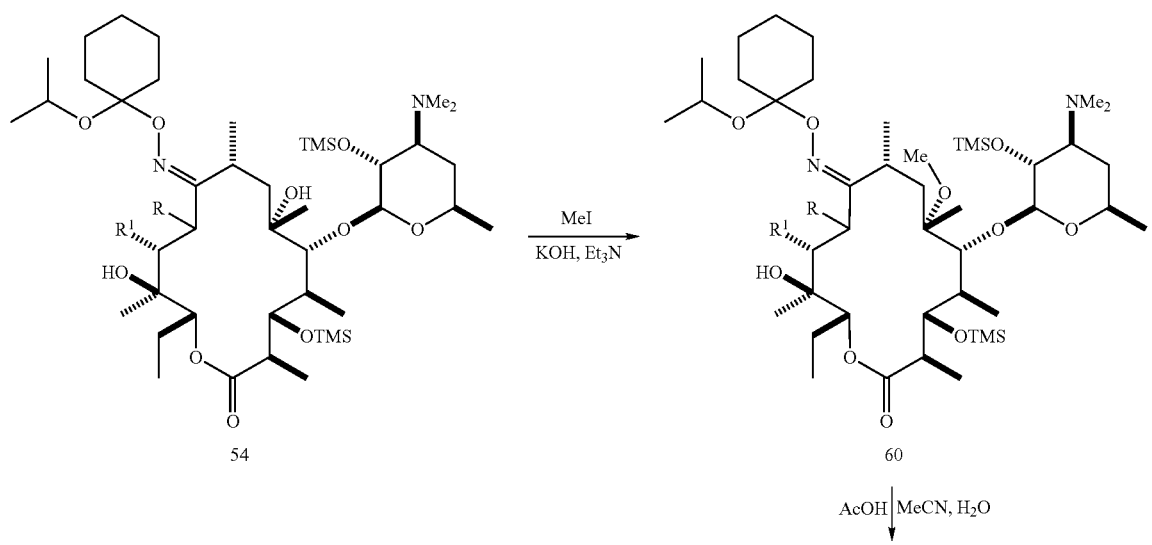

-continued
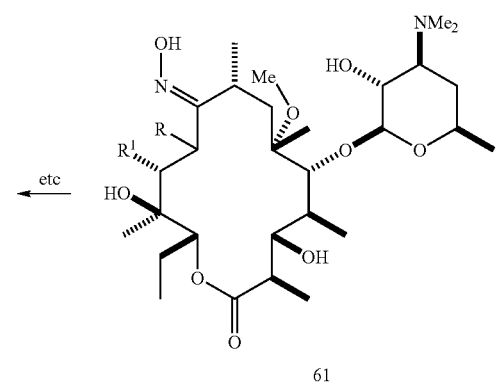
Scheme 16
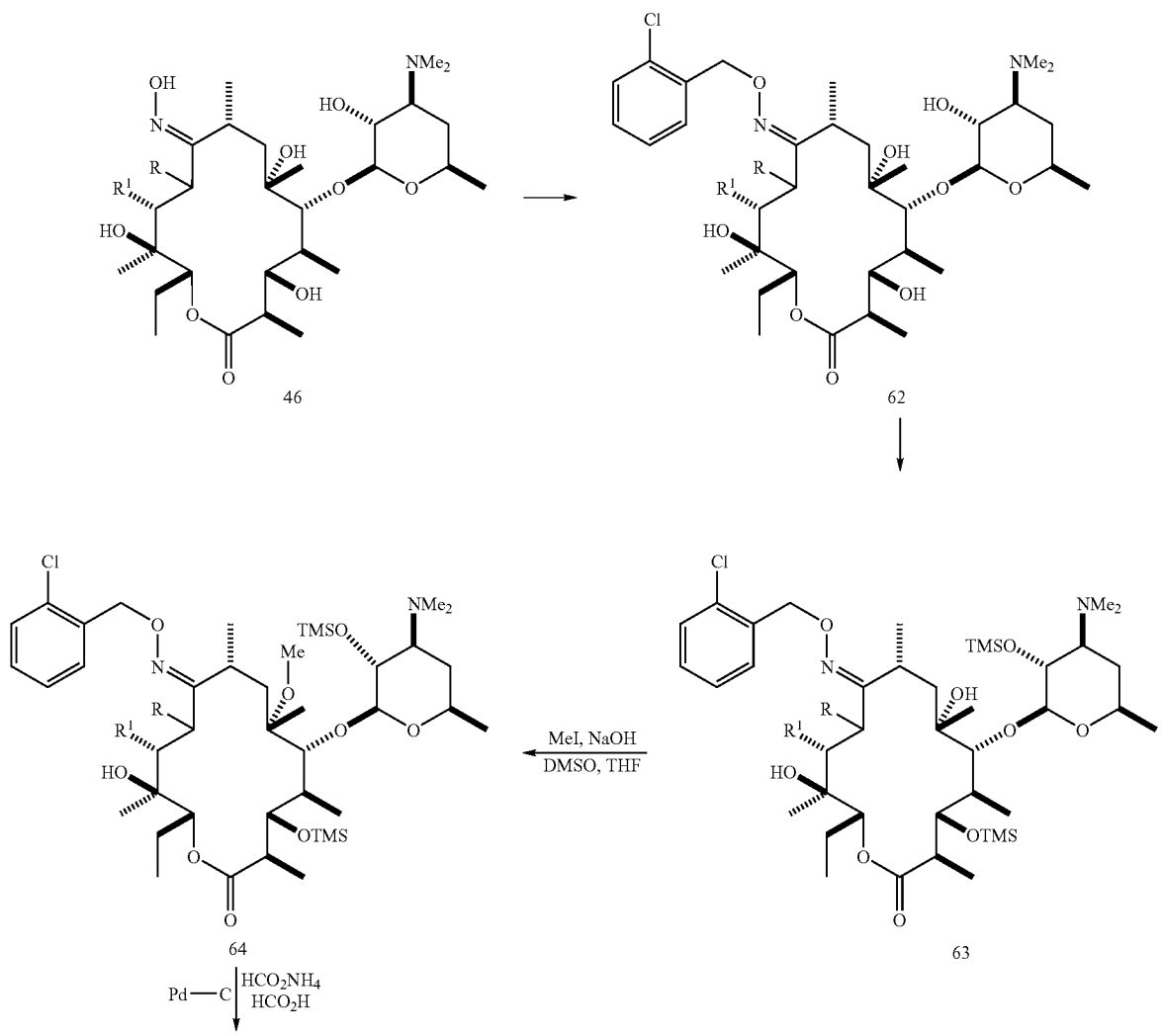

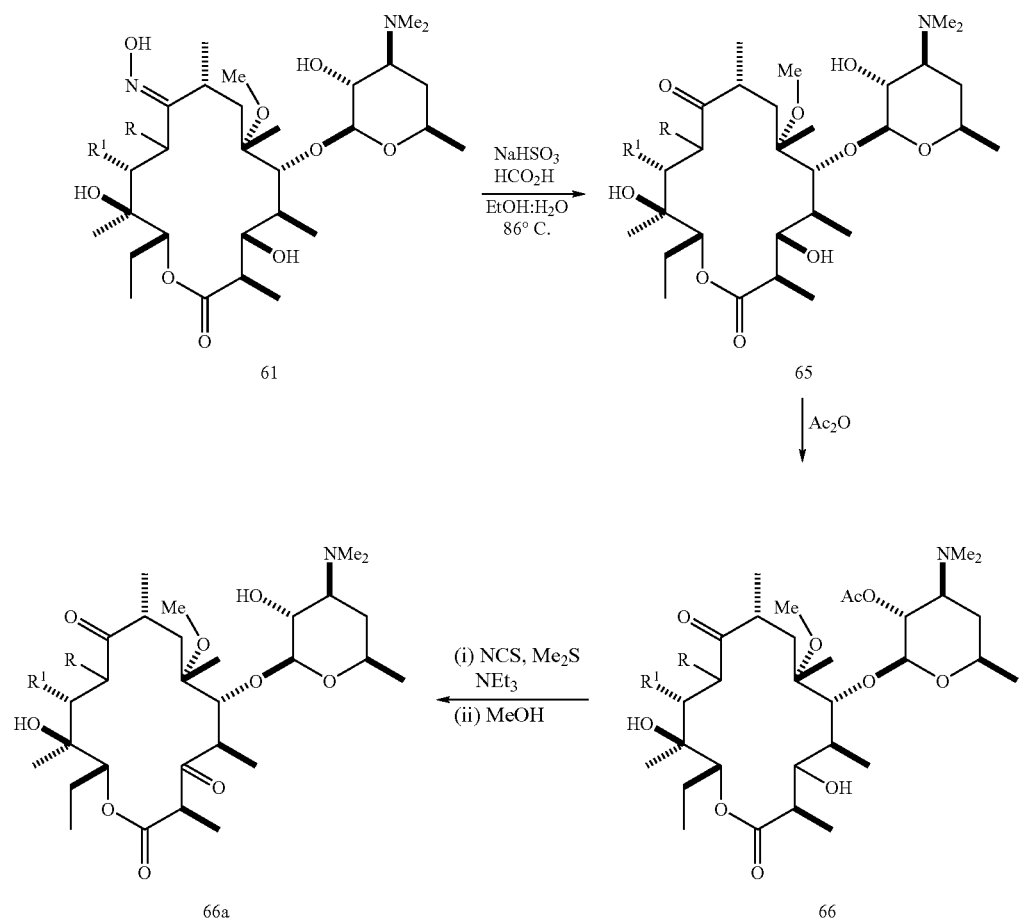
Scheme 17
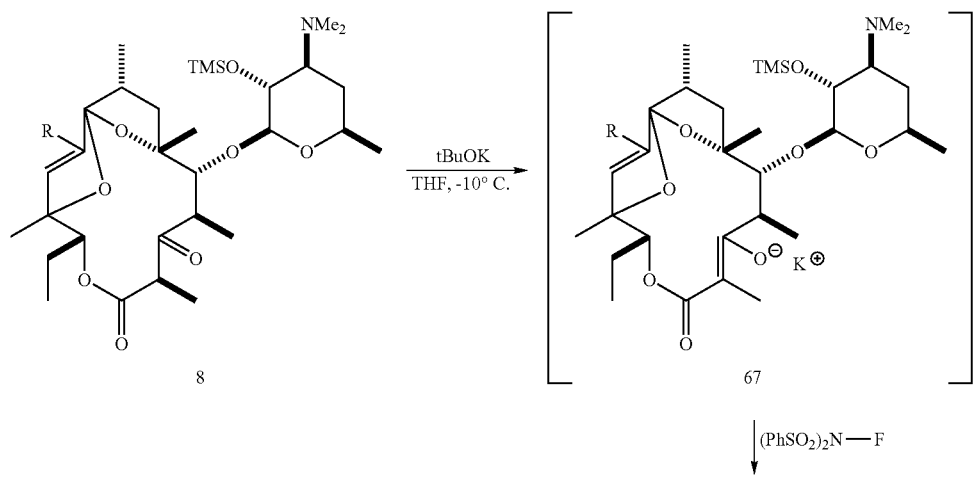

-continued
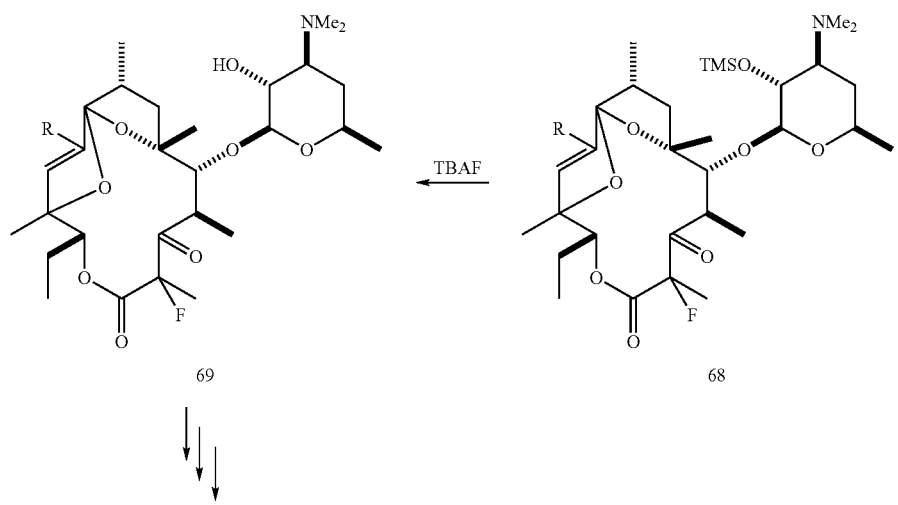
Scheme 18
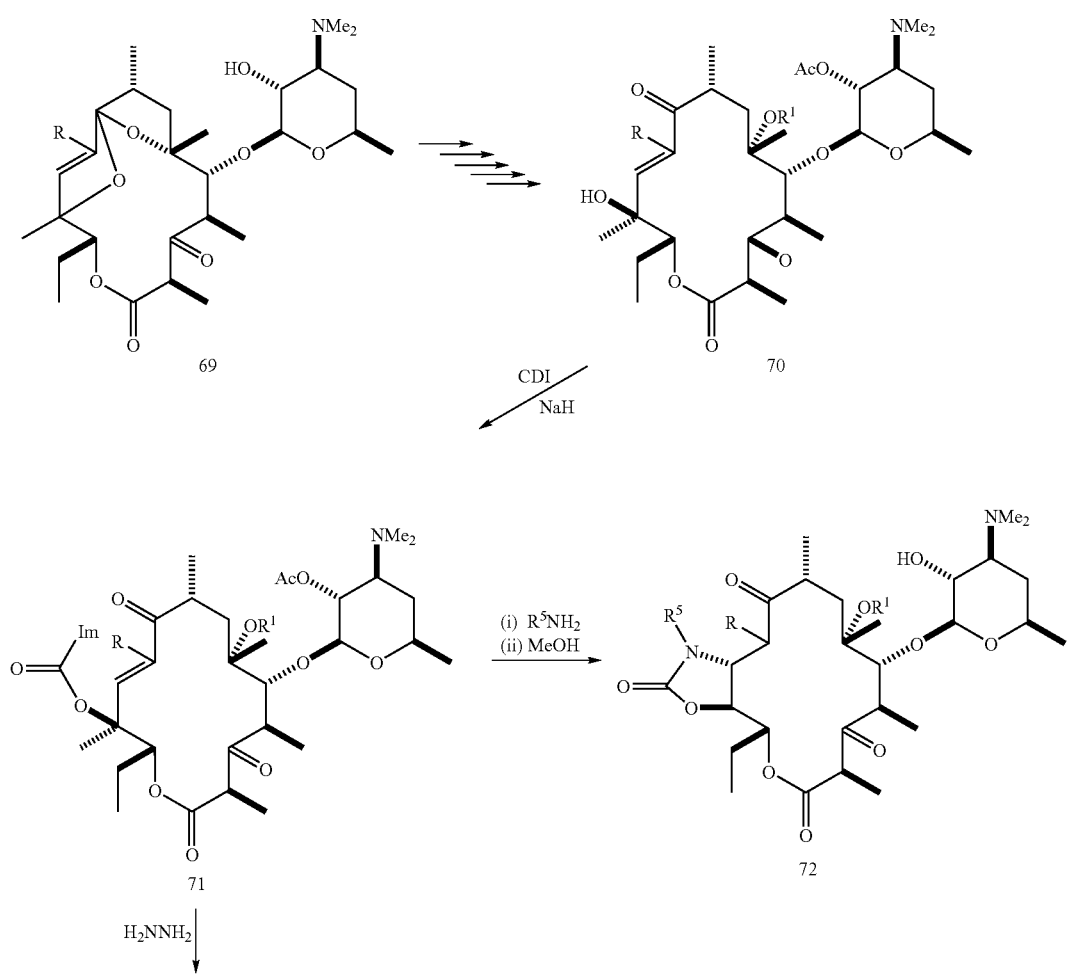

-continued
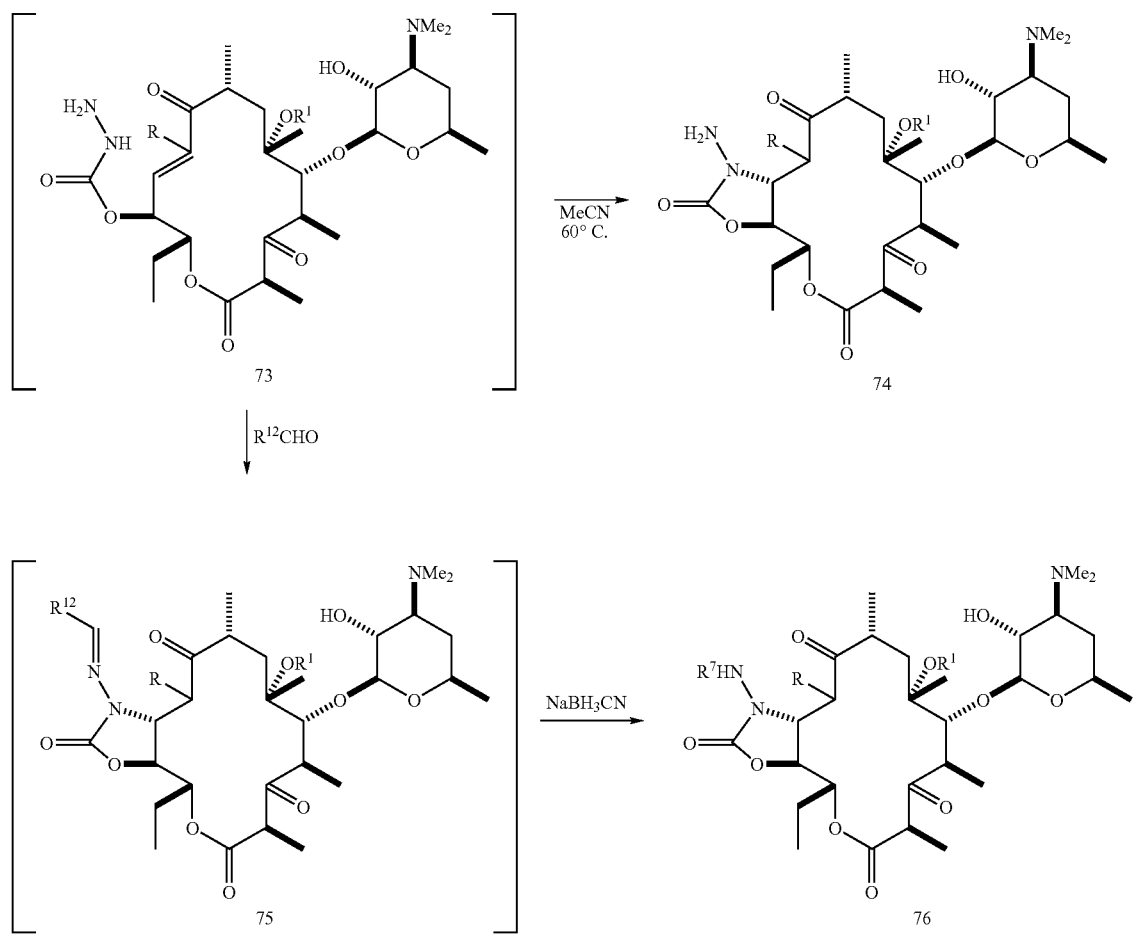
Scheme 19
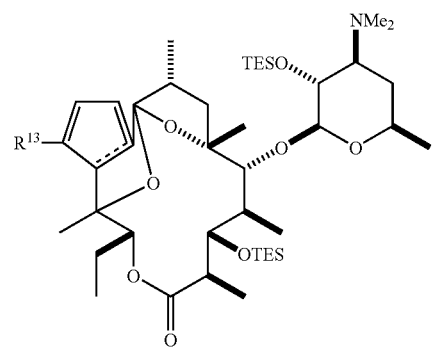

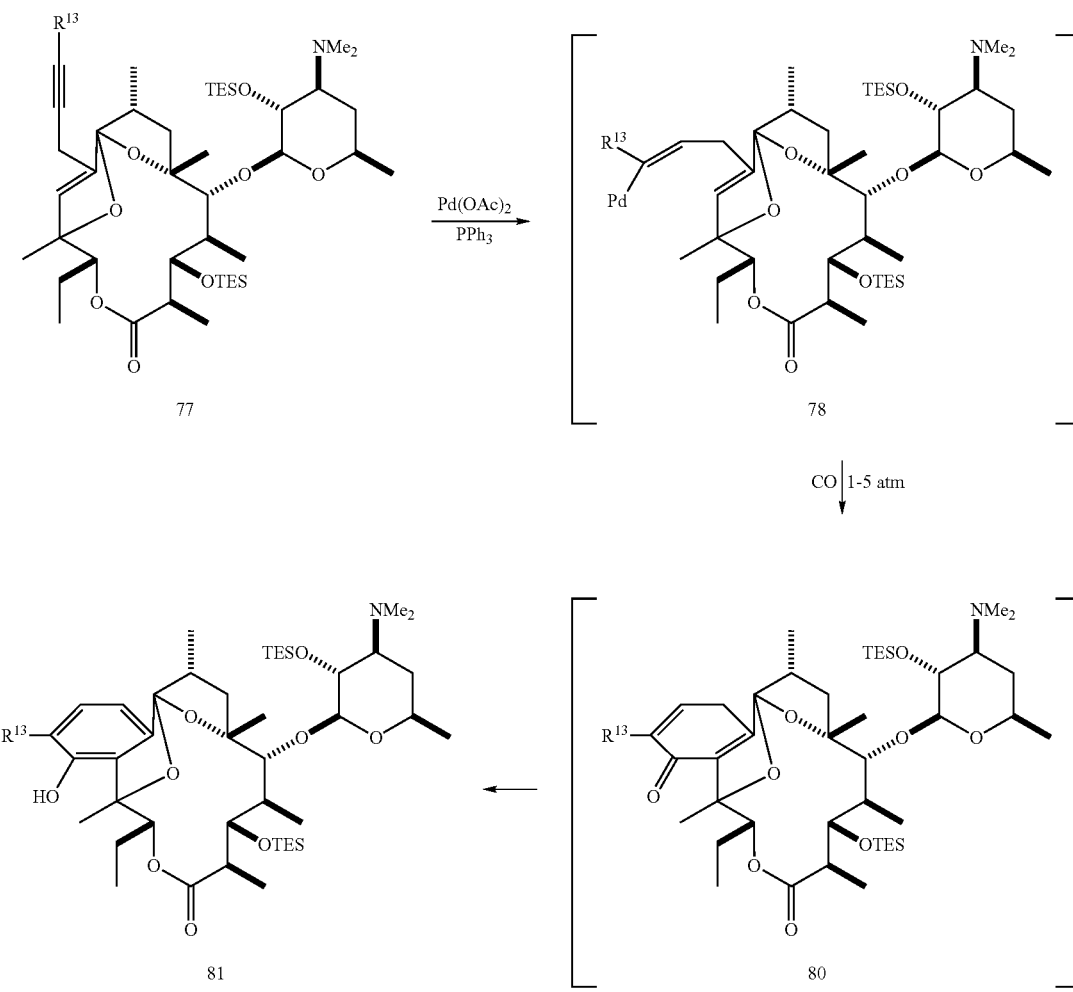
Scheme 20
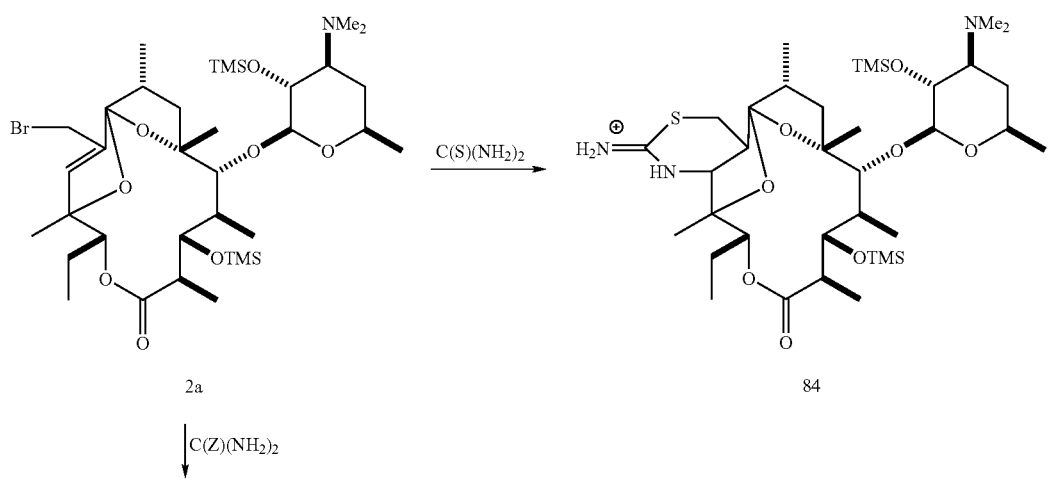

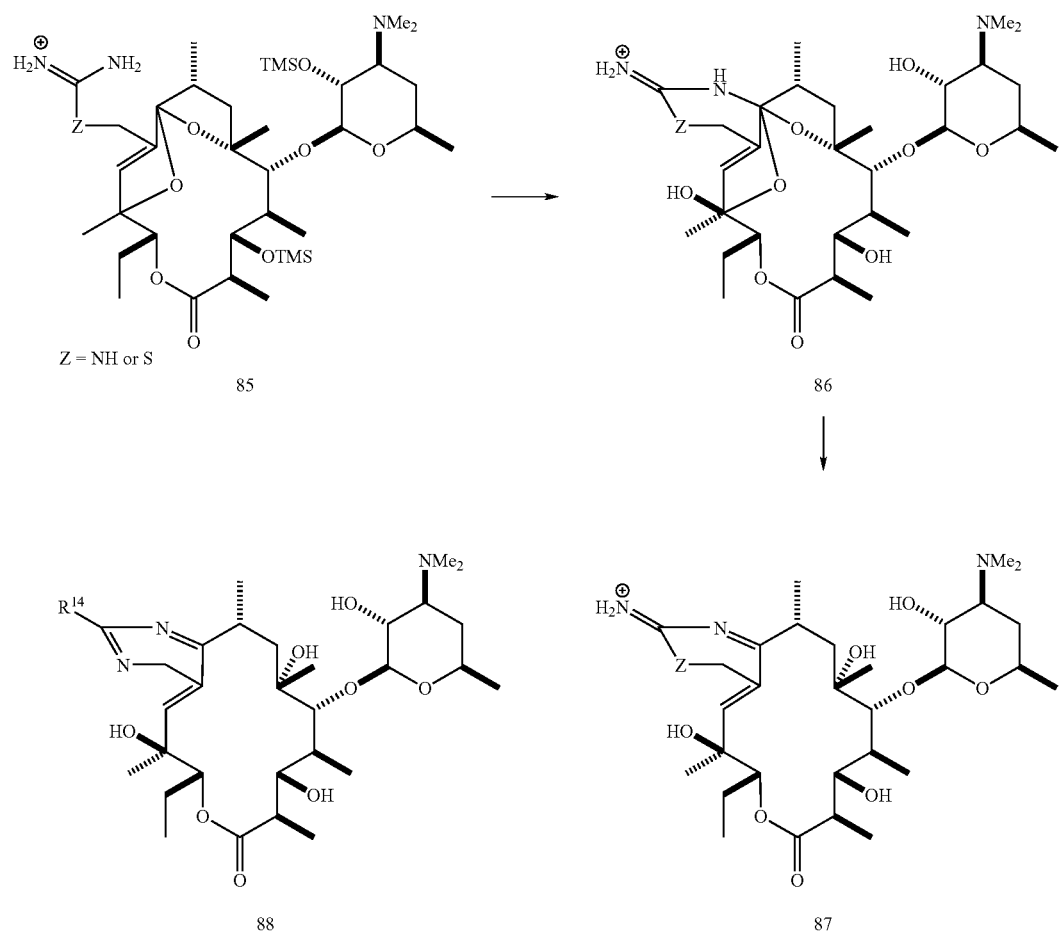
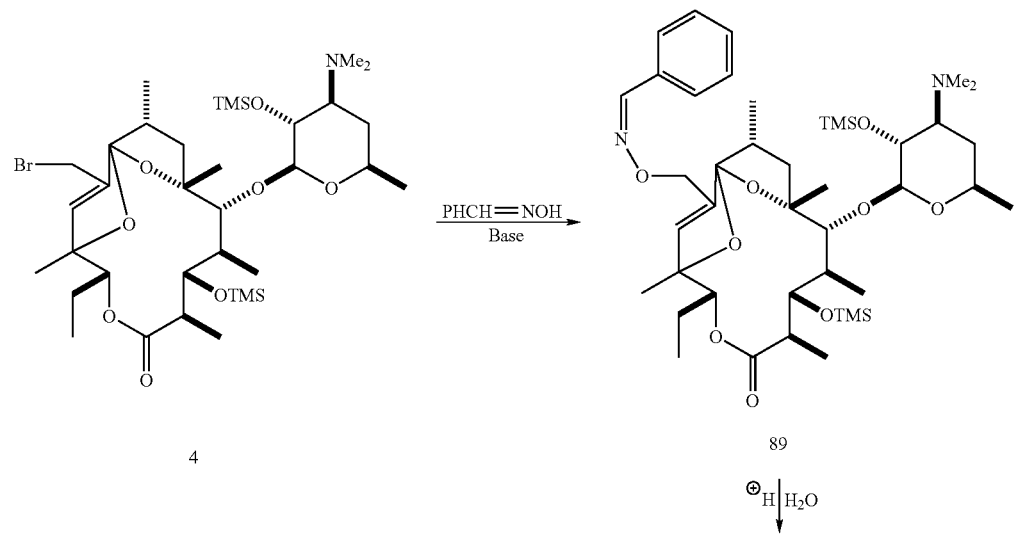
Scheme 21

-continued
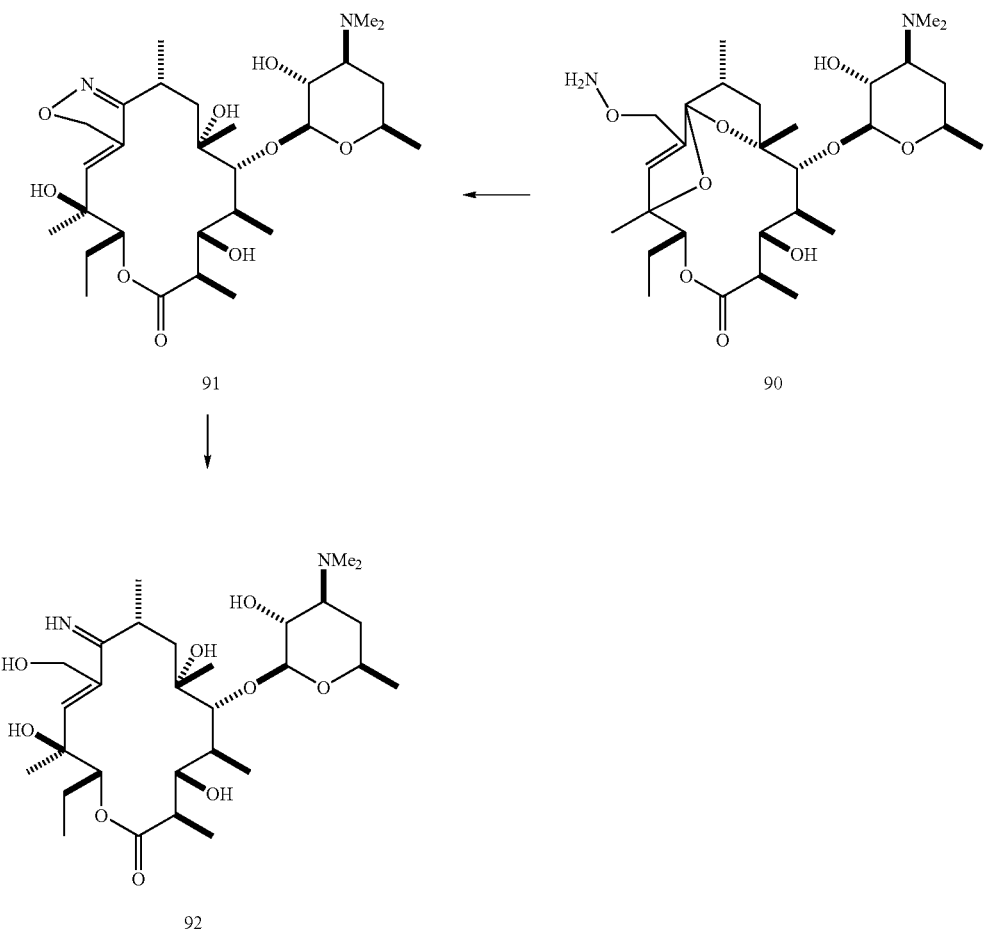
Scheme 22
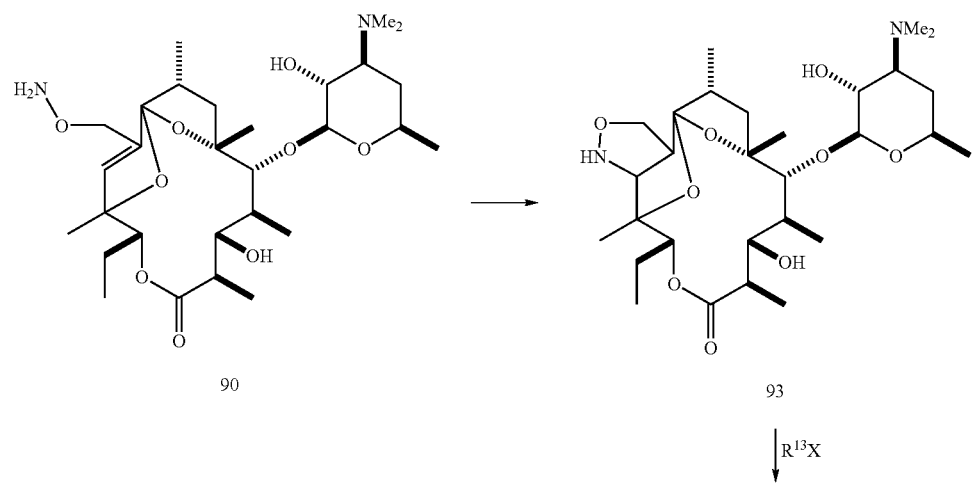

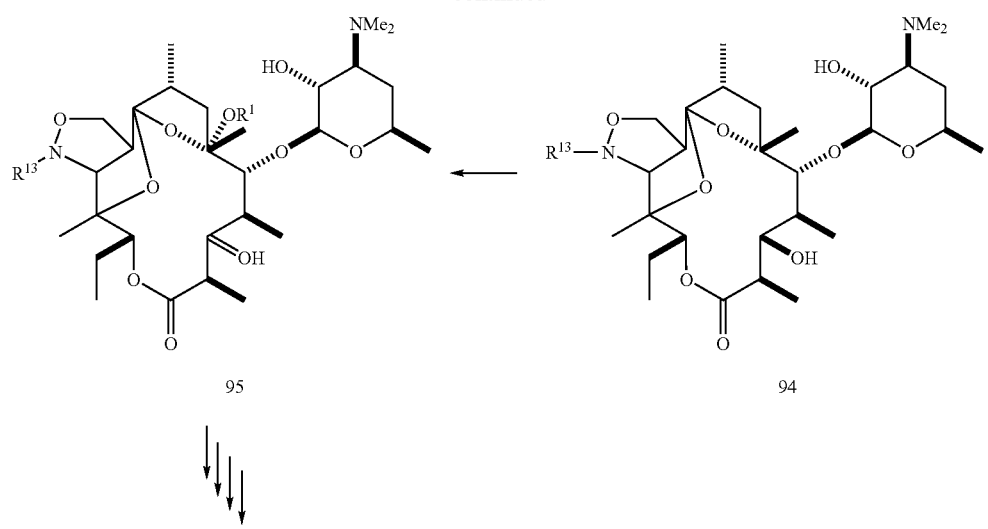
Scheme 23
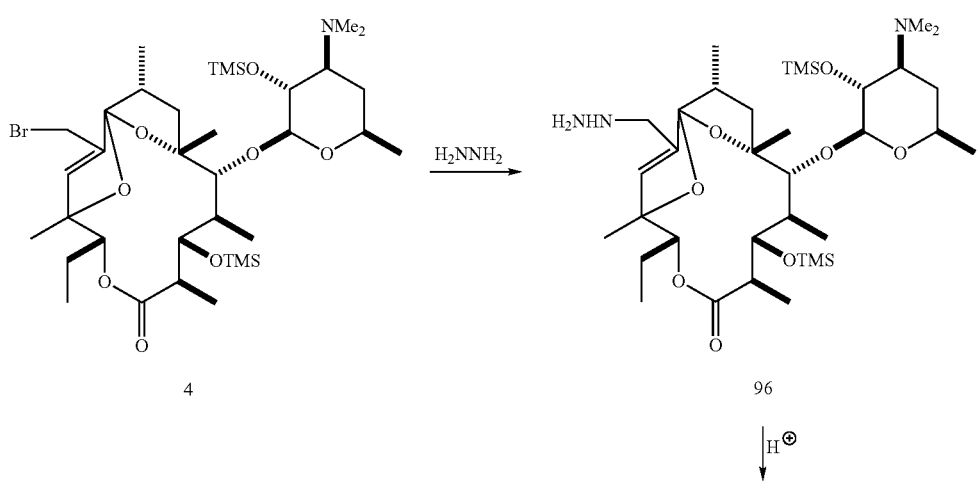
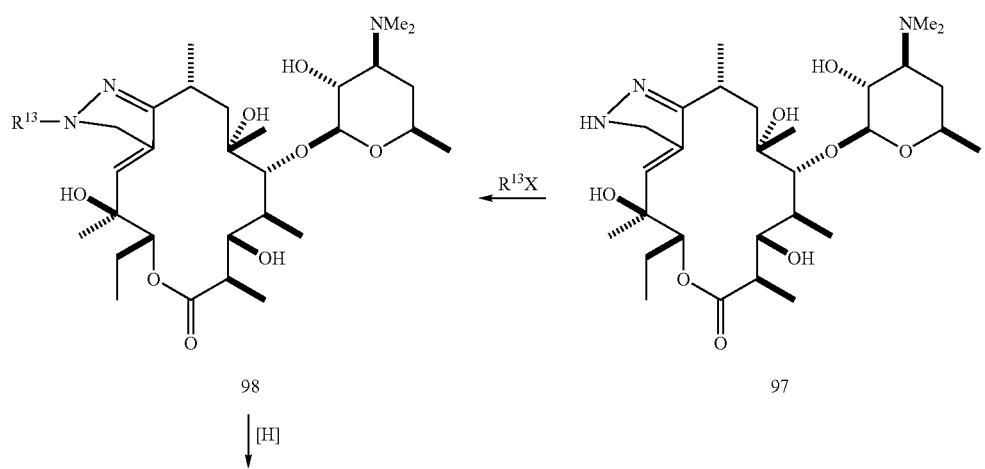

-continued
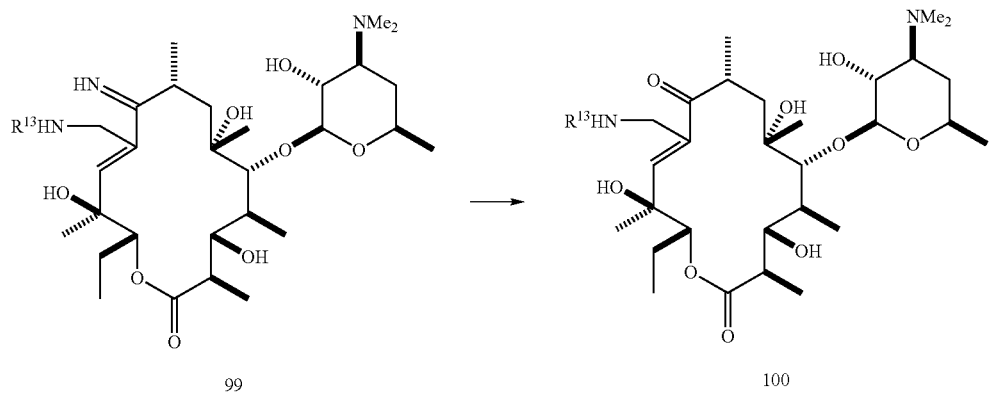
Scheme 24
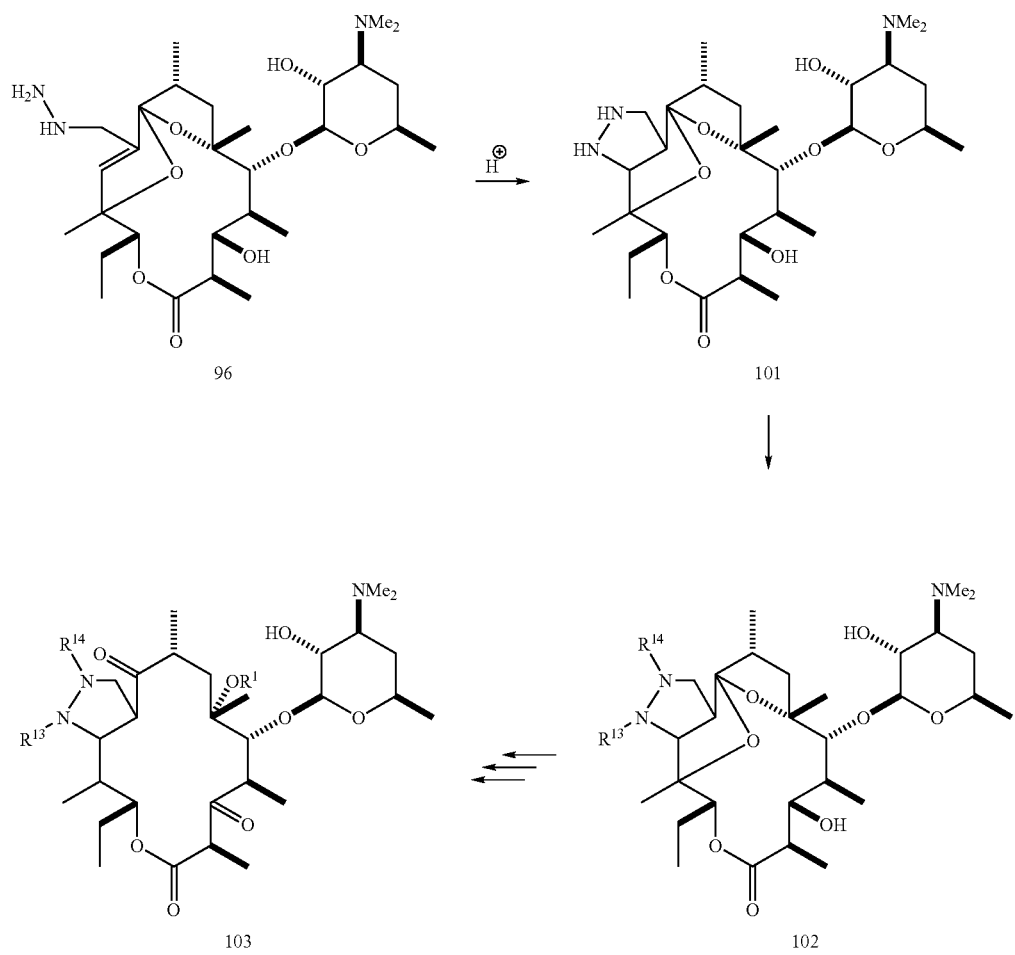

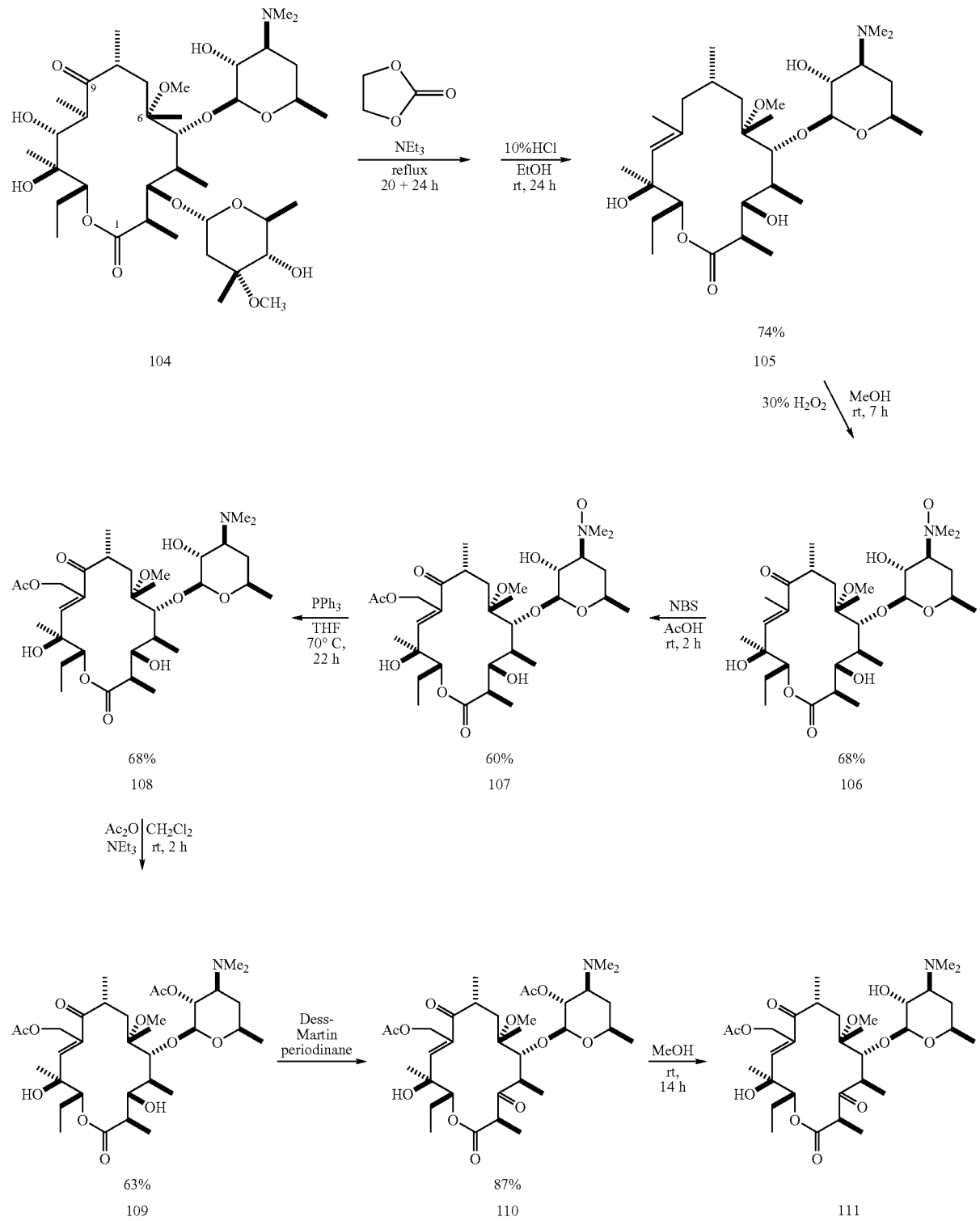
Scheme 25

Scheme 26
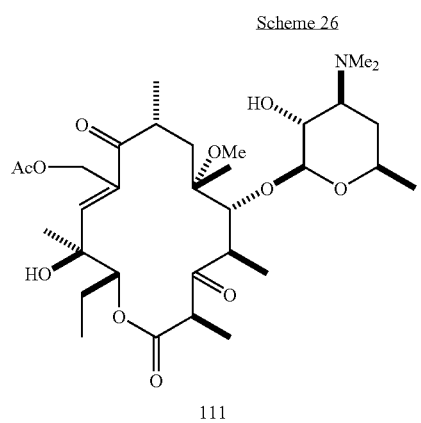 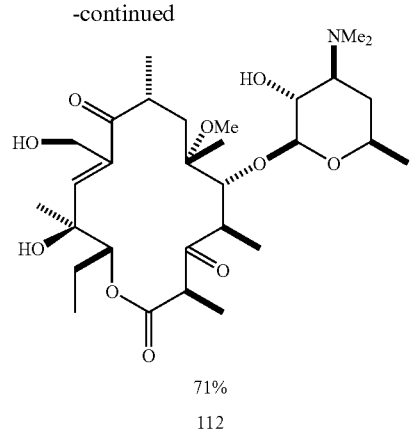
Scheme 27
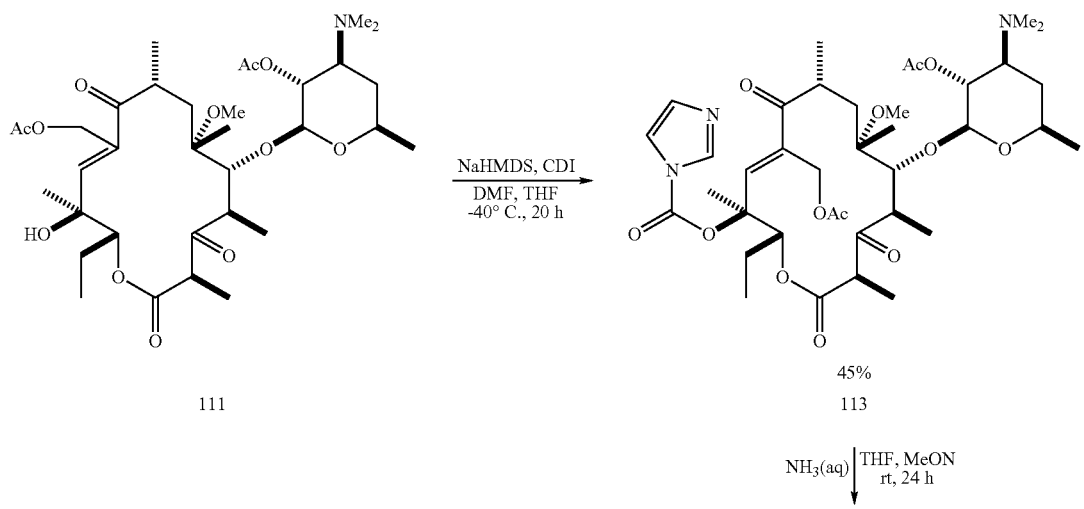
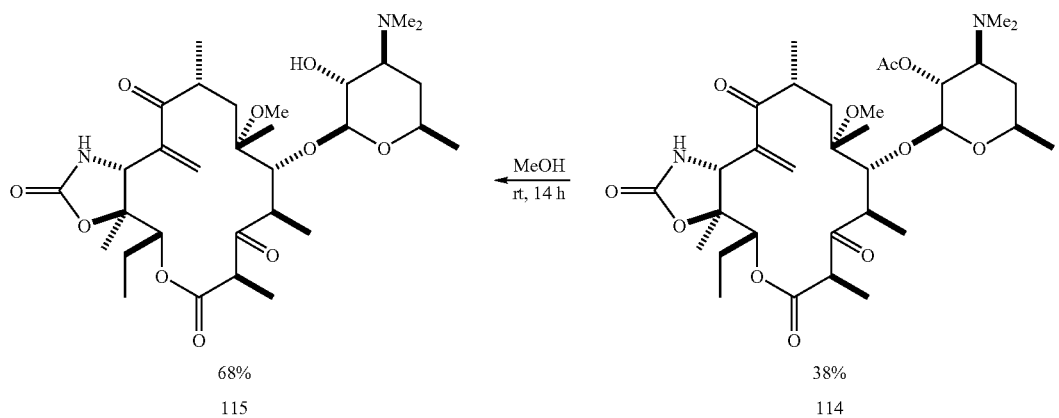

Scheme 28
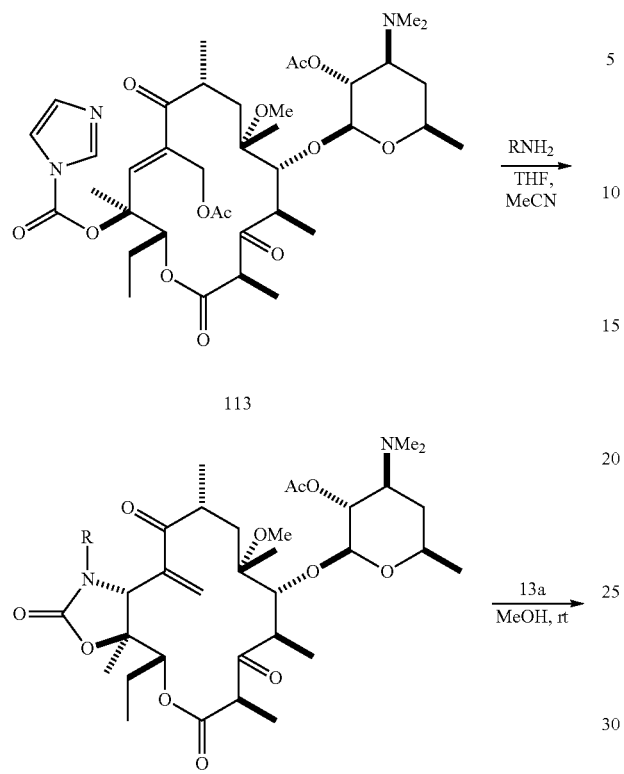
116a R = Bn 60% (rt, 21 h)
116b R = 4-Ph(CH₂)₄ = 76% (65° C., 20 h)
Scheme 29
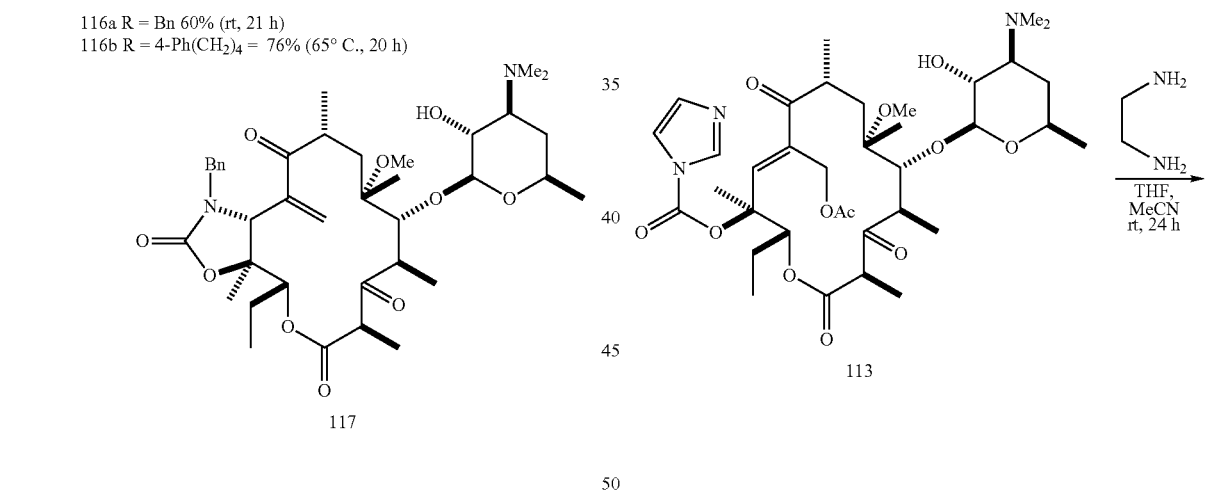
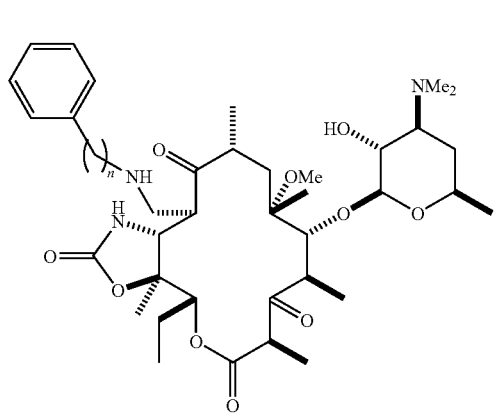
118a n = 1 (THF, reflux 17 h)
118b n = 3 (DMF, 60° C., 4 h)
Scheme 30
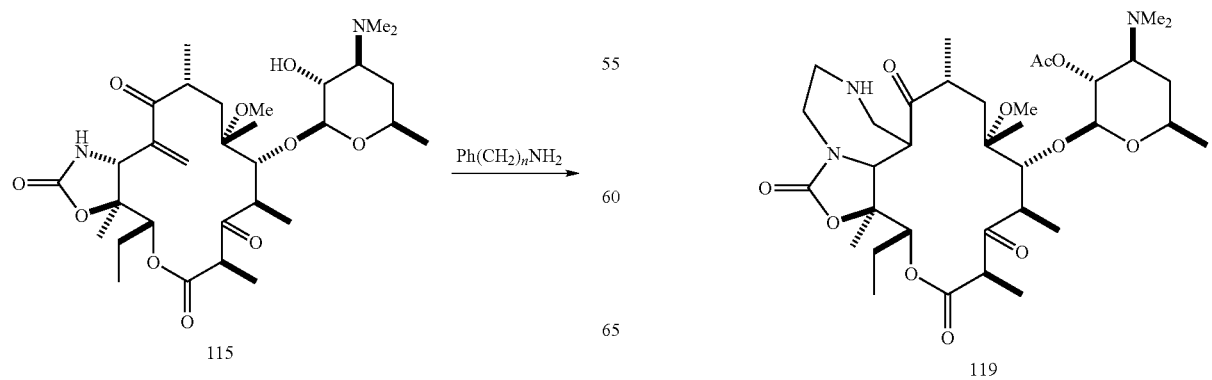

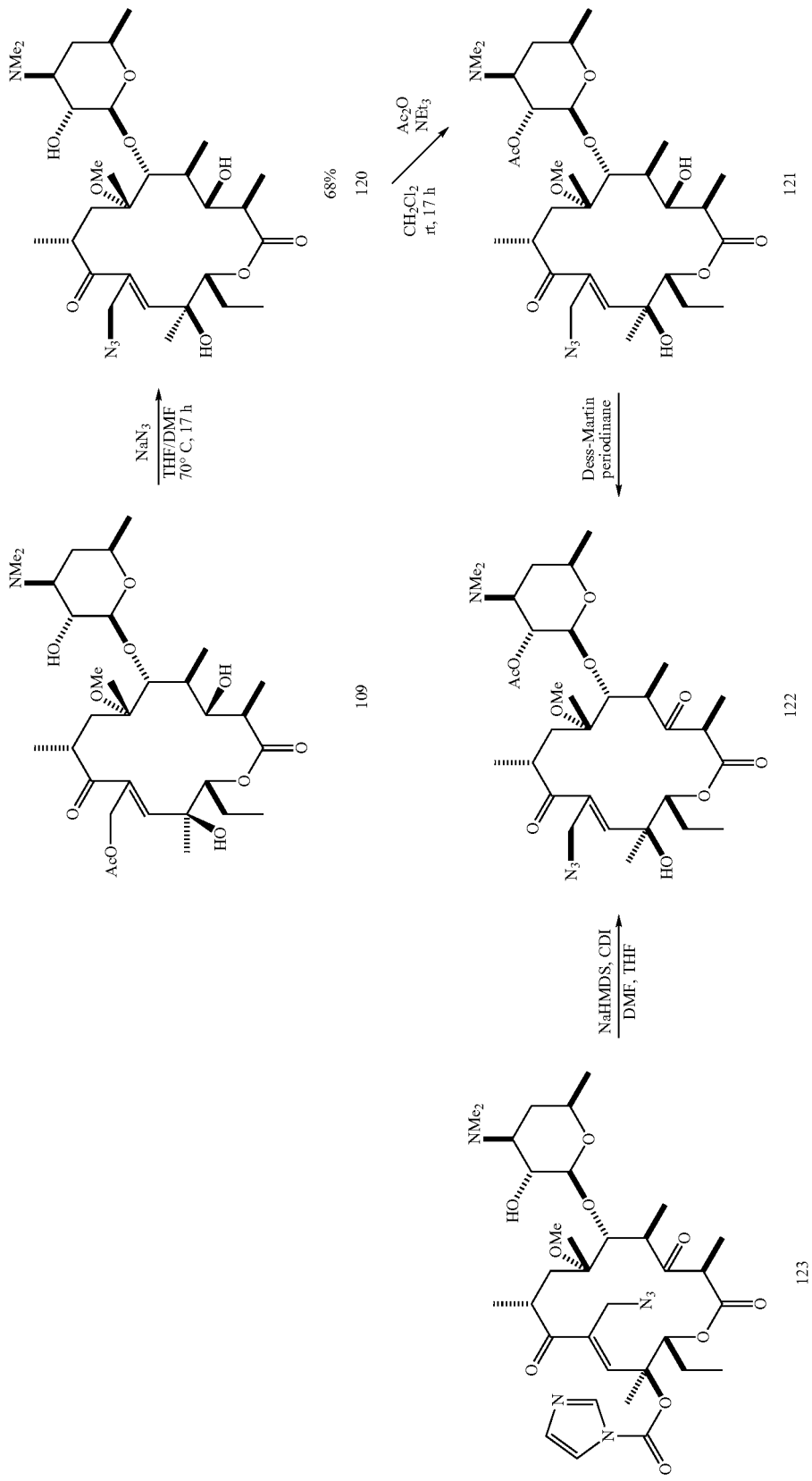

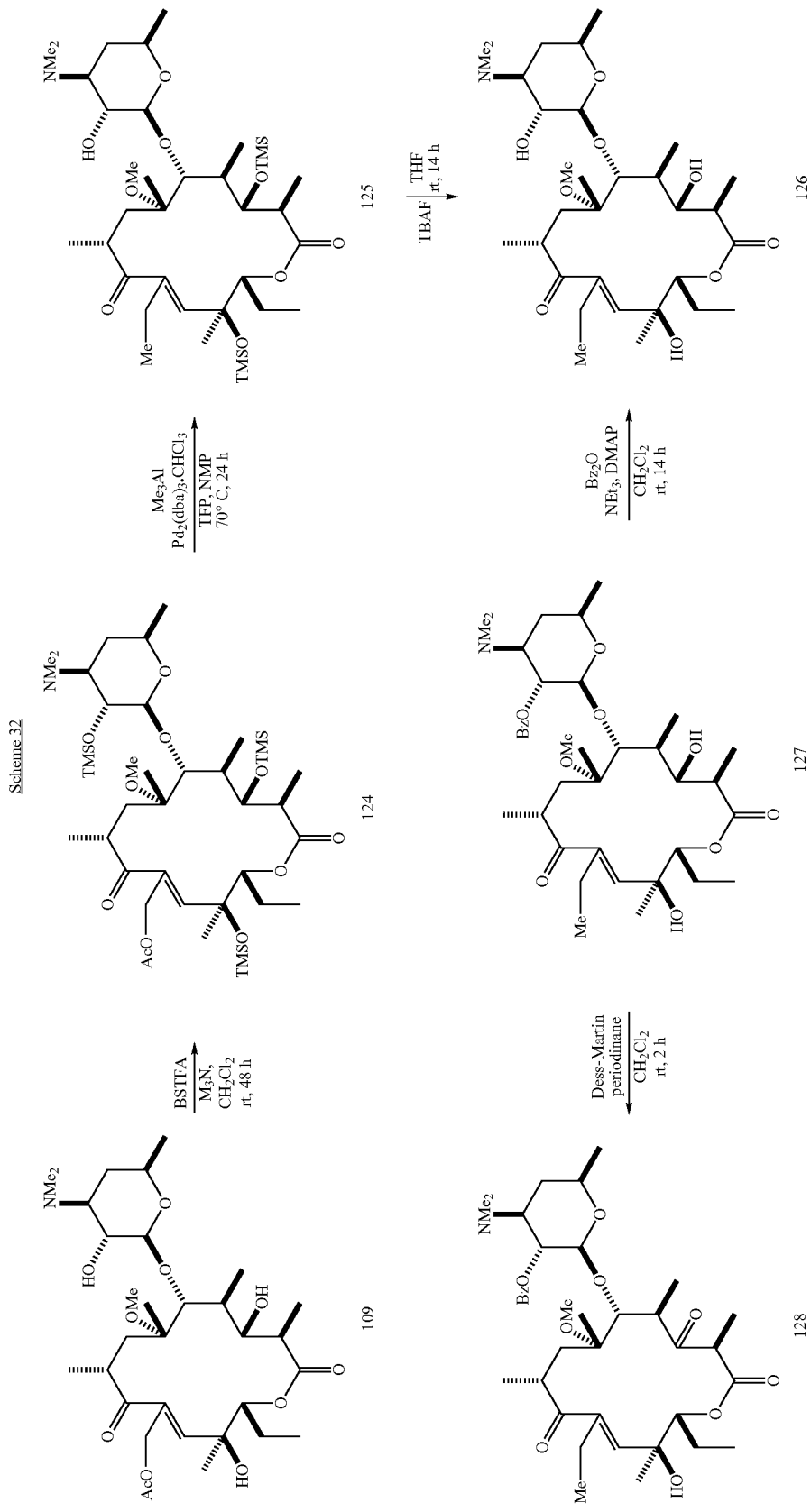

Scheme 33
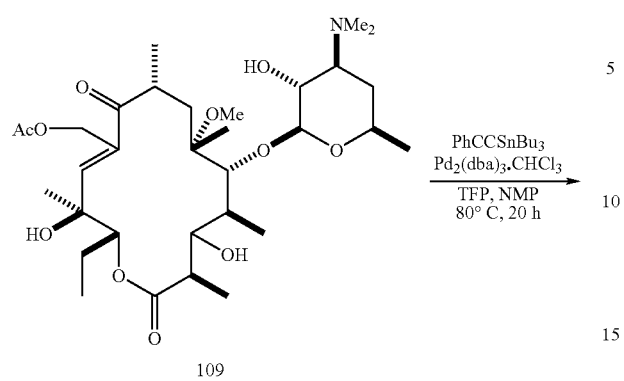
109
PhCCSnBu₃
Pd₂(dba)₃·CHCl₃
TFP, NMP
80° C, 20 h
-continued
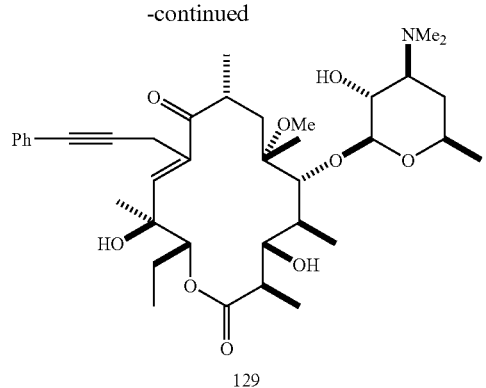
129

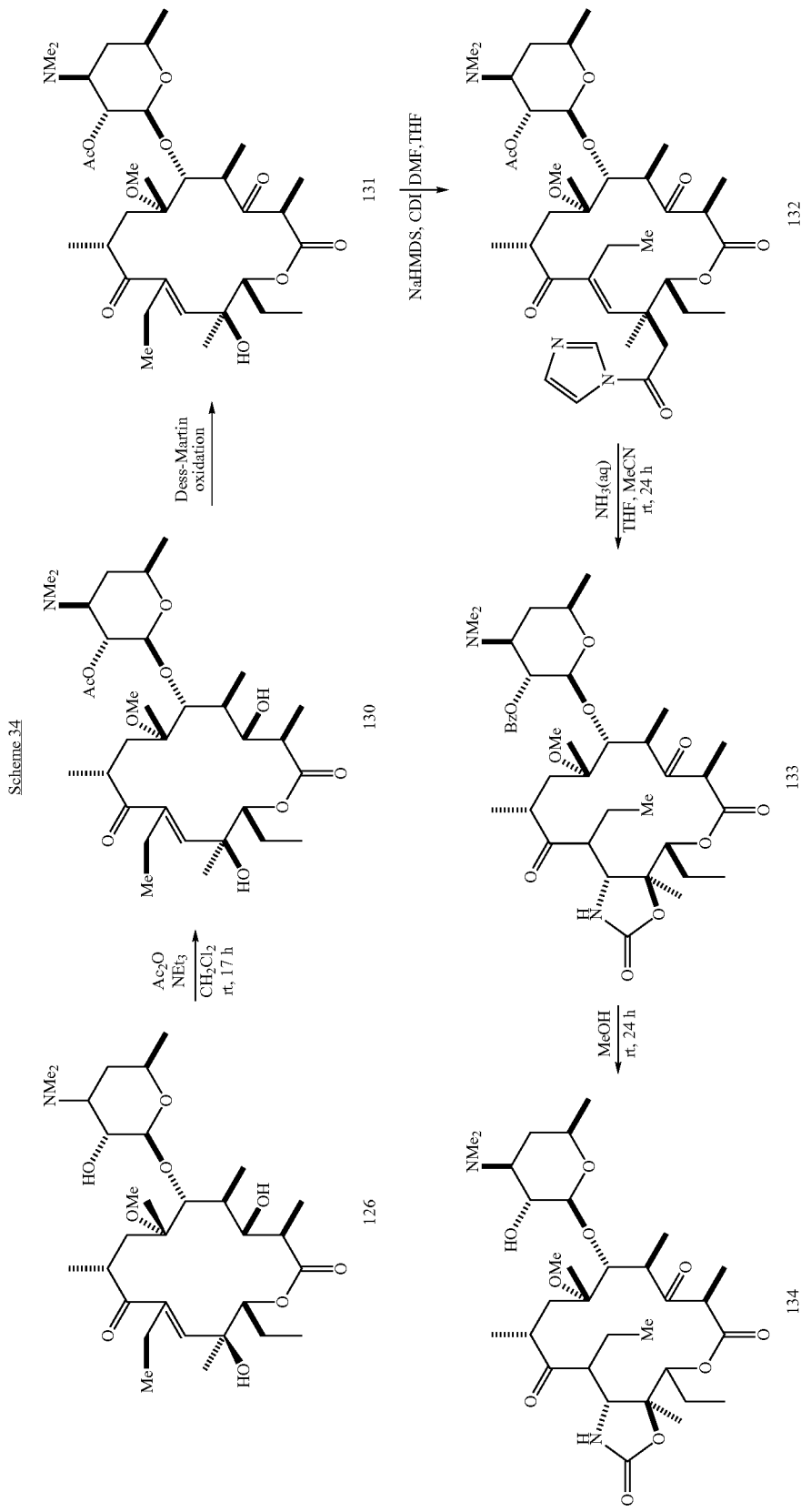

Scheme 35
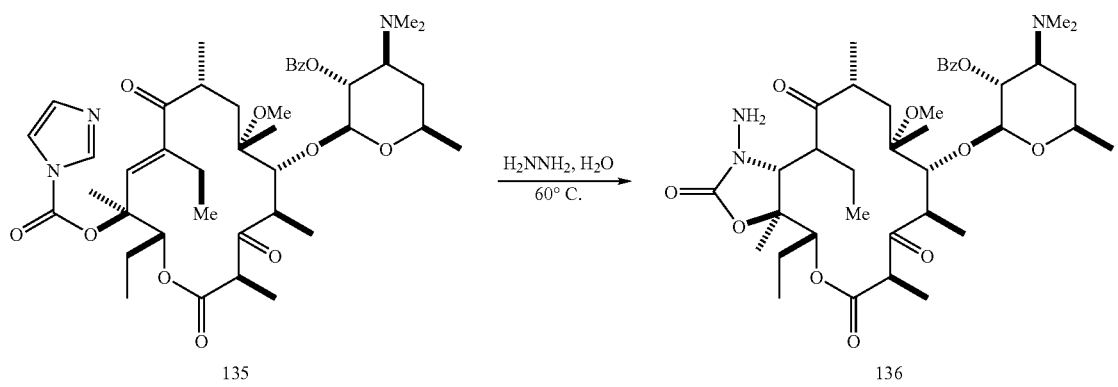
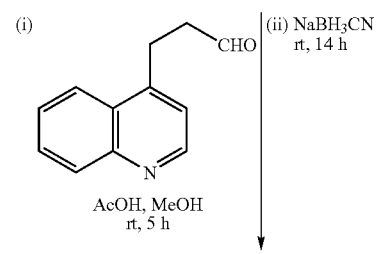
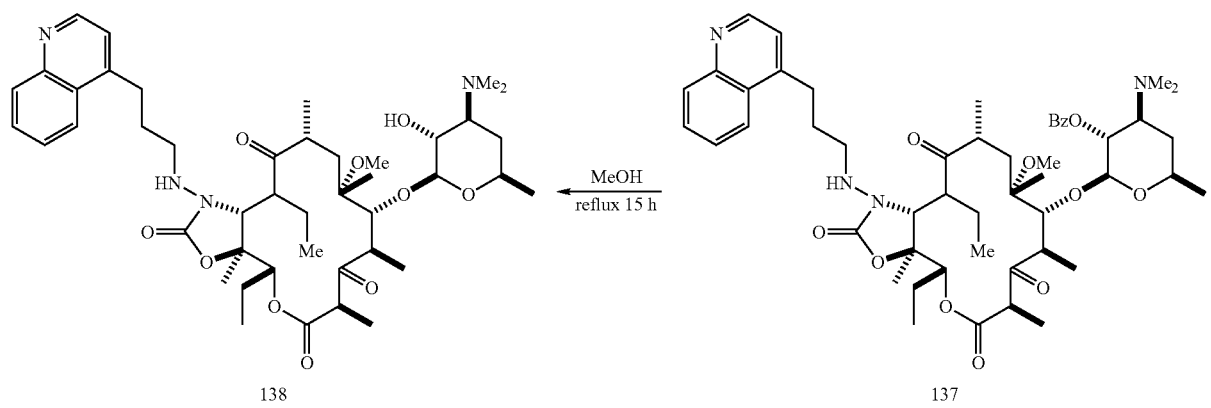

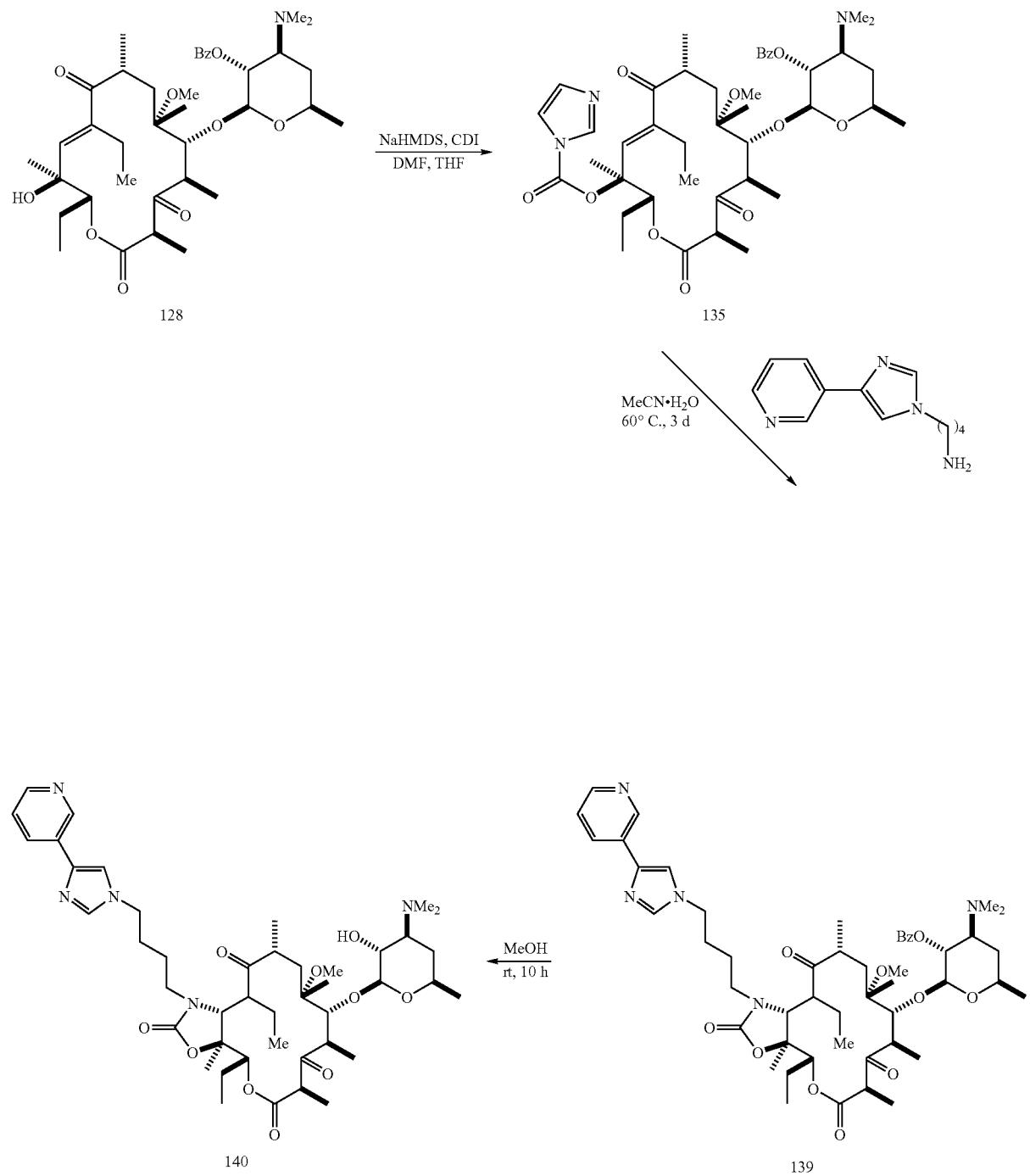

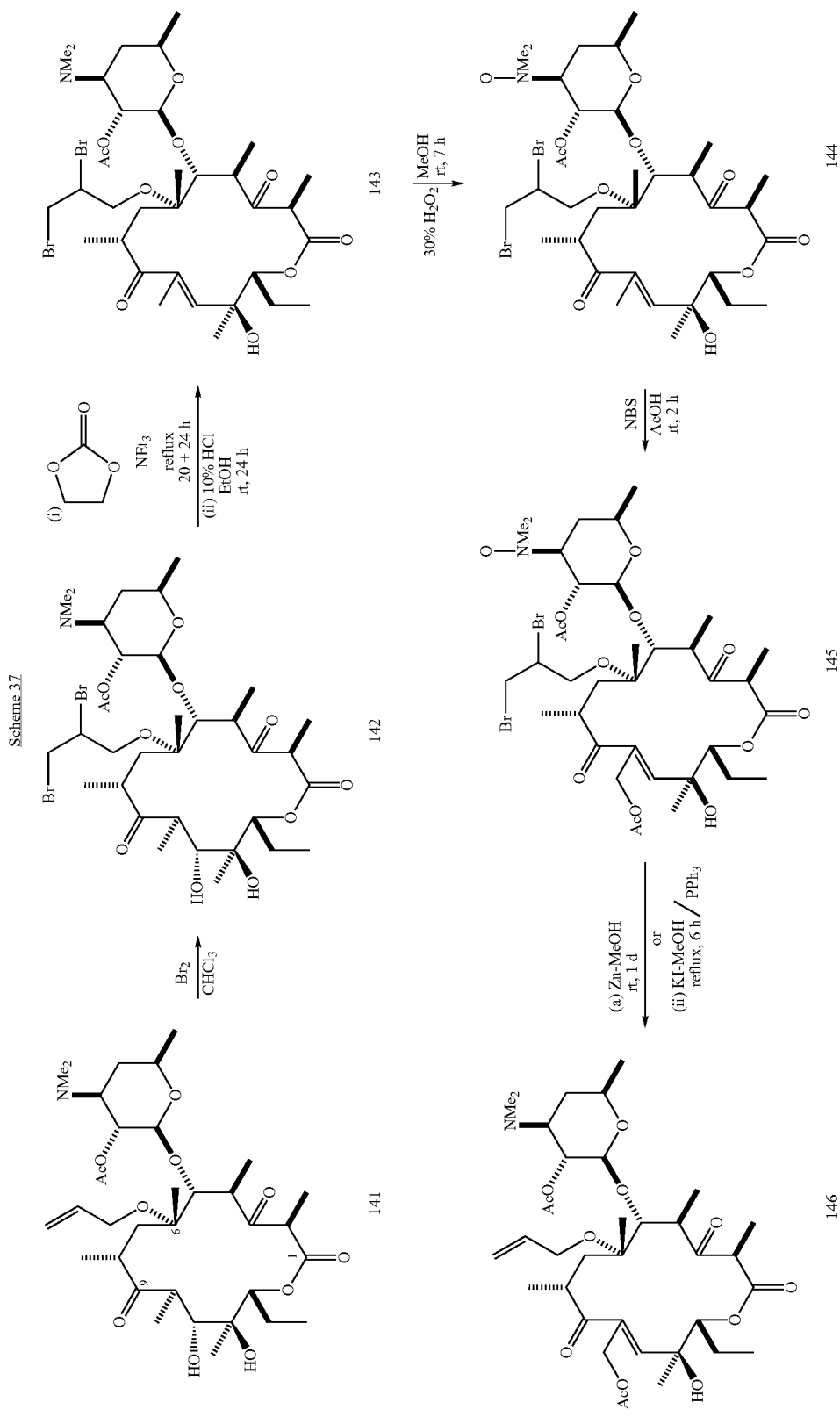

Embodiments of the invention, which illustrate the invention in a non-limiting fashion, are set out below in the following Examples.

EXAMPLE 1

Erythralosamine (2) [Flynn et al. J. Am. Chem. Soc. 76: 3121-3131 (1954)

A solution of erythromycin A (6.66 g, 9.1 mmol) in a mixture of EtOH (60 ml) and 10% HCl (200 ml) was stirred at ambient temperature for 24 h. The mixture was diluted with ethyl acetate (3×200 ml), washed with water (3×200 ml), dried (MgSO$_4$) and the solvent was evaporated. The residual material was subjected to flash chromatography on silica gel using CH$_2$Cl$_2$:MeOH:aq.NH$_3$, initially in ratio 90:4:1, then in ratio 90:8:2. Rf 0.19. The product was a white crystalline solid; yield 3.22 g (66%), mp 208° C.

HRMS: M 539.3412. Calc. for C$_{29}$H$_{19}$NO: 539.3458.

EXAMPLE 2

O$^{2',3}$-Bis (trimethylsilyl) erythralosamine (2a)

A solution of erythralosamine (2) (1.59 g, 0.0029 mol) and triethylamine (2.4 ml, 0.0174 mol) in THF (40 ml) under argon was cooled to −78° C. and trimethylsilyl trifluoromethanesulfonate (1.59 ml, 0.0088 mol) added dropwise. The mixture was stirred for 20 h, extracted into ethyl acetate, the solution shaken with brine, dried (MgSO$_4$) and evaporated. The residual material was subjected to flash chromatography on silica gel using hexane:Et$_2$O 3:1 with 1% Et$_3$N; yield: 1.59 g (80%) of a crystalline material.

HRMS: M 684.4338. Calc. for C$_{33}$H$_{65}$NO$_8$Si$_2$: 684.4321.

EXAMPLE 3

O$^{2',3}$-Bis(triethylsilyl)erythralosamine (2b)

A solution of erythralosamine (2) (0.673 g, 0.0012 mol) and triethylamine (0.50 ml, 0.0036 mmol) in dichloromethane (10 ml) under argon was cooled to −78° C. and TES-triflate (0.81 ml, 0.0036 mmol) was added dropwise. Ethyl acetate was added after 24 h, the solution shaken brine and dried (MgSO$_4$) before evaporation to dryness. The residual material was subjected to flash chromatography on silica gel using hexane:Et$_2$O 3:1 and 1% Et$_3$N; yield 0.75 g (81%) of a white crystalline material.

HRMS: M 768.5248. Calc. for C$_{41}$H$_{77}$NO$_8$Si$_2$: 768.5260.

EXAMPLE 4

O$^{2',3}$-Bis(t-butyldimethylsilyl)erythralosamine (2c)

A solution of erythralosamine (2) (0.475 g, 0.880 mmol) and triethylamine (0.37 ml, 2.640 mmol) in CH$_2$Cl$_2$ (5 ml) was cooled to 0° C. and TBDMS-triflate (0.50 ml, 2.640 mmol) was added dropwise to the reaction mixture. Water was added to the cold reaction mixture after 22 h, the mixture extracted with ethyl acetate, the extracts shaken with aqueous sodium hydrogen carbonate, with brine, dried (MgSO$_4$) and the solvent distilled off. The residual material was subjected to flash chromatography on silica gel using hexane:Et$_2$O 3:1; yield 0.593 g (89%) of a white crystalline solid, mp 92-93° C.

HRMS: [M+1] 768.5297. Calc. for C$_{41}$H$_{77}$NO$_8$Si$_2$: 768.5260.

EXAMPLE 5

Erythralosamine N-Oxide (3)

30% Hydrogen peroxide (1 ml) was added to a solution of erythralosamine (2) (1.4 g, 2.52 mmol) in methanol (10 ml) and the reaction mixture stirred at ambient temperature for 7 h. Saturated aqueous sodium bisulfite was added slowly to the reaction mixture to remove excess hydrogen peroxide before extraction with chloroform. The dried (MgSO$_4$) chloroform solution was evaporated. The residual material was the title compound that was sufficiently pure for use in the subsequent reaction. The product was a white crystalline solid with mp 153-155° C.; yield 100%.

HRMS: [M+1] 556.3484. Calc. for C$_{29}$H$_{50}$BrNO$_9$: 556.3480.

EXAMPLE 6

10-Bromomethyl-10-desmethyl-erythralosamine N-Oxide (4)

A solution of N-bromosuccinimide in acetic acid (15 ml) was added to a solution of erythralosamine N-oxide (3) (1.56 g, 2.5 mmol) in acetic acid (20 ml) and the resultant solution stirred at room temperature for 3 h when TLC showed the reaction to be complete. Most of the acetic acid was removed under reduced pressure and aqueous potassium hydroxide was added to the reaction mixture until pH 9-11. The product was extracted into chloroform that was washed and dried (MgSO$_4$) before the solvent was distilled off. The product was isolated after flash chromatography on silica gel using CH$_2$Cl$_2$:MeOH:NH$_3$, initially in ratio 9:1:0.1, and then 9:2: 0.1; yield 0.95 g (60%) of a white crystalline material, mp 149-151° C.

HRMS: M 634.2556. Calc. for C$_{29}$H$_{49}$BrNO$_9$: 634.2591.

EXAMPLE 7

10-Bromomethyl-10-desmethyl-erythralosamine (5)

A solution of 10-bromomethyl-10-desmethyl-erythralosamine N-oxide (4) (2.60 g, 0.004 mol) and triphenylphosphine (2.20 g, 0.008 mol) in THF (30 ml) was heated under reflux for 17 h when TLC monitoring showed that the reaction had gone to completion. Most of the THF was removed by distillation, the residual material extracted into ethyl acetate, the extracts shaken with aqueous sodium bicarbonate, washed with brine, dried (MgSO$_4$), the solution evaporated and the residual material subjected to flash chromatography on silica gel using CH$_2$Cl$_2$:MeOH:NH$_3$ 90:8:2; yield 2.13 g (86%) of a white crystalline material, mp 88-90° C.

HRMS: M 618.2607. Calc. for C$_{29}$H$_{48}$BrNO$_8$: 618.2636.

EXAMPLE 8

10-Bromomethyl-O$^{2',3}$-Bis(t-butyldimethylsilyl)-10-desmethyl-erythralosamine (5a)

A solution of 10-bromomethyl-10-desmethyl-erythralosamine (5) (0.250 g, 0.404 mmol) and trimethylamine (0.17 ml, 1.212 mmol) in CH$_2$Cl$_2$ (5 ml) was cooled to 0° C. and TBDMS-triflate (0.23 ml, 1.212 mmol) added dropwise to the reaction mixture. Water was added to the cold reaction mixture after 17 h, the mixture extracted with ethyl acetate, the extracts shaken with aqueous sodium hydrogen carbonate, with brine, dried (MgSO$_4$) and the solvent distilled off. The residual material was subjected to flash chromatography on silica gel using hexane:Et$_2$O 5:1; yield 0.25 g (73%) of a white crystalline solid, mp 151-152° C.

HRMS: [M+1], 846.4329. Calc. for C$_{41}$H$_{76}$NO$_8$Si$_2$Br: 846.4365.

EXAMPLE 9

O$^{2'}$-Acetyl-erythralosamine (6)

Acetic anhydride (0.88 ml, 9.30 mmol) and triethylamine (129 ml, 9.30 mmol) were added to a solution of erythralosamine (2)(2.50 g, 4.69 mmol) in CH$_2$Cl$_2$ (15 ml) and the reaction mixture stirred at room temperature for 2 h until TLC monitoring showed full conversion. The reaction mixture was diluted with ethyl acetate, the solution shaken with 5% Na$_2$CO$_3$ (aq), with brine, dried (MgSO$_4$) and evaporated. The residual material was subjected to flash chromatography using silica gel, 90:4:1 CH$_2$Cl$_2$:MeOH:NH$_3$ (aq); yield 2.30 g (84%) of a white solid, mp 153-154° C.

HRMS: M 581.3554. Calc. for C$_{29}$H$_{49}$NO$_8$: 581.3564.

EXAMPLE 10

O$^{2'}$-Acetyl-erythralosamine-3 ketolide (7)

Dimethyl sulfide (0.24 ml, 7.72 mmol) was added dropwise from a syringe over 5 min to a stirred solution of N-chlorosuccinimide (NCS) (0.363 g, 2.12 mmol) in dichloromethane (8 ml) at 10° C. under argon. The solution was stirred at this temperature for 10 min before a solution of O$^{2'}$-acetylerythralosamine (6) (1.05 g, 1.81 mmol) in dichloromethane (12 mL) was added dropwise over 20 min. The mixture was stirred for 30 min at −10 to −5° C. when triethylamine (0.28 mL, 1.99 mmol) was added over 5 min. The mixture was stirred for an additional 45 min at this temperature and then allowed to reach room temperature and the solvent removed at reduced pressure. The residual material was extracted into ethyl acetate, the solution shaken with 5% Na$_2$CO$_3$, with brine, dried (MgSO$_4$) and the solvent distilled off. The residual material was subjected to flash chromatography on silica gel using NEt$_3$:acetone:hexane 1:25:75; yield 0.66 g (63%) of a white solid, mp 235° C. Rf 0.17.

HRMS: M 580.3480. Calc. for C$_{31}$H$_{49}$NO$_9$: 580.3480.

EXAMPLE 11

Erythralosamine 3-ketolide (8)

O$^{2'}$-Acetyl-erythralosamine-3 ketolide (7) (0.50 g, 0.86 mmol) was dissolved in methanol (10 ml) and the reaction mixture stirred at room temperature for 16 h until TLC monitoring showed full conversion. The solvent was removed under reduced pressure and the residual material purified by flash chromatography on silica gel using NEt$_3$:acetone:hexane 1:25:75. Rf 0.15. Yield 0.37 g (80%) of a white solid, mp 179° C.

HRMS: M 538.3354. Calc. for C$_{29}$H$_{47}$NO$_8$: 538.3374.

EXAMPLE 12

Erythralosamine 3-ketolide N-Oxide (9)

30% Hydrogen peroxide (1 ml) was added to a solution of erythralosamine 3-ketolide (8) (0.307 g, 0.507 mmol) in methanol (2 ml) and the reaction mixture stirred at ambient temperature for 4 h. Saturated aqueous sodium bisulfite was added slowly to the reaction mixture to remove excess hydrogen peroxide before extraction with ethyl acetate. The dried (MgSO$_4$) solution was evaporated. The residual material was the title compound, which was sufficiently pure for use in the subsequent reaction. The product was a white crystalline solid with mp 139-141° C.; yield 73%.

HRMS: [M+1] 554.3315. Calc. for C$_{29}$H$_{47}$NO$_9$: 554.3323.

EXAMPLE 13

10-Benzyl-10-desmethyl-erythralosamine (12)

A solution of 10-bromomethyl-10-desmethyl-erythralosamine (5) (0.280 g, 0.453 mmol) in NMP (5 ml) was degassed and tris(2-furyl)phosphine (0.025 g, 0.109 mmol) and Pd$_2$ dba$_3$.CHCl$_3$ (0.014 g, 0.014 mmol) added. The reaction mixture was heated at 50° C. for 10 min before tributyl (phenyl)stannane (0.30 ml, 0.906 mmol) was added. The reaction mixture was heated at 100° C. for 20 h. The cold reaction mixture was extracted into ethyl acetate, the solution shaken with aqueous sodium hydrogen carbonate, with brine, dried (MgSO$_4$) and the solvents distilled off at reduced pressure. The residual material was subjected to flash chromatography on silica gel using CH$_2$Cl$_2$:MeOH:NH$_3$ 90:4:1 and then CH$_2$Cl$_2$:MeOH (9:2); yield 0.168 g (60%) of a white crystalline material mp. 151-152° C.

HRMS: M 616.3847. Calc. for C$_{35}$H$_{53}$NO$_8$: 616.3843.

EXAMPLE 14

10-(2-Furylmethyl)-10-desmethyl-erythralosamine (13)

A solution of 10-bromomethyl-10-desmethyl-erythralosamine N-oxide (4) (0.196 g, 0.310 mmol) in NMP (3 ml) was degassed and tris(2-furyl)phosphine (0.018 g, 0.077 mmol) and Pd$_2$ dba$_3$.CHCl$_3$ (0.010 g, 0.010 mmol) added. The reaction mixture was heated at 50° C. for 10 min and more tris(2-furyl)phosphine (0.12 ml, 0.372 mmol) added. The reaction mixture was heated at 80° C. for 22 h. The product was extracted with ethyl acetate, the organic phase washed with aqueous sodium hydrogen carbonate, brine and dried (MgSO$_4$). The NMP was removed under reduced pressure and the residual material subjected to flash chromatography on silica gel using CH$_2$Cl$_2$:MeOH:NH$_3$ 90:4:1, yield 0.096 g (51%) of a white crystalline solid.

HRMS: [M+1] 606.3654. Calc. for C$_{33}$H$_{51}$NO$_9$: 606.3636.

EXAMPLE 15

10-Phenylethynylmethyl-10-desmethyl-erythralosamine (14)

1-methyl-2-pyrrolidone was degassed and tris(2-furyl) phosphine (0.022 g, 0.096 mmol) and Pd$_2$ dba$_3$ CHCl$_3$ (0.013 g, 0.012 mmol) added. The reaction mixture was heated at 50° C. for 10 min before tributyl(phenylethynyl)stannane (0.21 ml, 0.589 mmol) was added. The reaction mixture was heated at 80° C. for 17 h. The solvents were distilled off at reduced pressure. The crude product was subjected to flash chromatography on silica gel using CH$_2$Cl$_2$:MeOH:NH$_3$ 90:4:1 and then CH$_2$Cl$_2$:MeOH (9:2); yield 0.240 g (76%) of a yellow foam.

HRMS: [M+1] 640.3817 (Calc. for C$_{37}$H$_{53}$NO$_8$: 640.3843).

EXAMPLE 16

$O^{2',3}$ Bis(t-butyldimethylsilyl)-10-ethyl-10-desmethyl-erythralosamine (15)

A solution of 10-bromomethyl-$O^{2',3}$-bis(t-butyldimethylsilyl)-10-desmethyl-erythralosamine (5a) (0.064 g, 0.080 mmol) in NMP (1 ml) was degassed for 1 h before tris(dibenzylideneacetone)dipalladium chloroform complex (0.002 g, 0.002 mmol) and tri(2-furyl)phosphine (0.004 g, 0.016 mmol) were added. The mixture was heated to 50° C. to generate the active catalyst and trimethylaluminium 2 M in hexane (0.2 ml, 0.400 mmol) added carefully through a syringe. The resultant reaction mixture was heated at 100° C. for 24 h. The cold reaction mixture was passed through a silica plug and the solvent was removed from the filtrate by distillation. The residual material was subjected to flash chromatography on silica gel using hexane:$Et_2O$ 4:1; yield 0.053 g (84%) of a white crystalline material.

HRMS: [M+1] 782.5383. Calc. for $C_{42}H_{79}NO_8Si_2$: 782.5417.

EXAMPLE 17

10-(2-Ethoxyprop-2-en-1-yl)-10-desmethyl-erythralosamine (16)

10-Bromomethyl-10-desmethyl-erythralosamine N-oxide (4) (0.100 g, 0.158 mmol) was deoxygenated when a solution with tris(2-furyl)phosphine (0.036 g, 0.158 mmol) in NMP (1 ml) was heated at 70° C. for 17 h. The catalyst $Pd_2dba_3.CHCl_3$ (0.005 g, 0.005 mmol) and tris(2-furyl)phosphine (0.009 g, 0.038 mmol) for the cross-coupling reaction were added to the reaction mixture together with tributyl (1-ethoxyethenyl)stannane (0.064 ml, 0.189 mmol). The resultant mixture was heated at 70° C. for 24 h. The solvent was removed at reduced pressure, the residue extracted into ethyl acetate, the solution shaken with aqueous sodium hydrogen carbonate, with brine, dried ($MgSO_4$), evaporated and the residual material subjected to flash chromatography on silica gel $CH_2Cl_2$:MeOH:$NH_3$ 90:4:1; yield 0.052 g (54%) of a white crystalline material.

HRMS: [M+1] 610.3948. Calc. for $C_{33}H_{55}NO_9$: 610.3949.

EXAMPLE 18

C-10 Benzylaminomethyl-10-desmethyl-erythralosamine (30)

A solution of 10-bromomethyl-10-desmethyl-erythralosamine (5) (0.502 g, 0.812 mmol) and benzylamine (0.35 ml, 3.246 mmol) in DMF (4 ml) was heated at 60° C. for 16 h. Water was added to the cold reaction mixture, the mixture extracted with ethyl acetate, the extracts shaken with aqueous sodium hydrogen carbonate, with brine, dried ($MgSO_4$) and the solvent distilled off. The residual material was subjected to flash chromatography on silica gel using $CH_2Cl_2$:MeOH:aq.$NH_3$ 90:8:2; yield 0.40 g (78%) of a white crystalline solid, mp 151-152° C.

HRMS: M 645.4102. Calc. for $C_{29}H_{48}BrNO_8$: 645.4109.

EXAMPLE 19

10-p-Chloroanilinomethyl-10-desmethyl-erythralosamine N-Oxide (31)

A solution of 10-bromomethyl-10-desmethyl-erythralosamine N-oxide (4) (0.613 g, 0.968 mmol) and p-chloroaniline (0.540 g, 3.872 mmol) in NMP (5 ml) was heated at 100° C. for 20 h. Water was added to the cold reaction mixture, the mixture extracted with ethyl acetate, the extracts shaken with aqueous sodium hydrogen carbonate, with brine, the solution dried ($MgSO_4$) and the solvent distilled off. The residual material was subjected to flash chromatography on silica gel using $CH_2Cl_2$:MeOH:aq.$NH_3$ 90:4:1; yield 0.129 g (20%) of a white crystalline material. HRMS [H$^+$]665.3547 (calculated for $C_{35}H_{53}N_2O_8Cl_1$ 665.3563.

HRMS: [M+1] 665.3547. Calc. for $C_{35}H_{53}NO_8Cl$: 665.3547.

EXAMPLE 20

11-Hydroxy-$O^{2',3}$-bis(trixmethylsilyl)erythralosamine N-oxide (37)

$O^{2',3}$-Bis(trimethylsilyl) erythralosamine (2a) (0.409 g, 0.598 mmol) was dissolved in a borane-methyl sulfide complex in THF (2M, 3 ml, 5.978 mmol) and the mixture stirred at ambient temperature for 17 h. Ethanol (0.5 ml) and 1 M sodium hydroxide (0.5 ml) were added to the resultant reaction mixture which was cooled to 0° C. before addition of hydrogen (30%, 2 ml). Stirring was continued for 2 h, the mixture extracted with ethyl acetate, the extracts shaken with sodium hydrogen carbonate, brine, dried ($MgSO_4$), and evaporated. The residual material was subjected to flash chromatography on silica gel using hexane:$Et_2O$ 1:1; yield 0.144 g (35%) of a white solid.

EXAMPLE 21

10,11-Epoxy-erythralosamine N-oxide (40)

A solution of erythralosamine (0.573 g, 1.062 mmol) and MCPBA (1.66 g, 7.432 mmol) in dichloromethane (20 ml) was heated under reflux for 4 h, another portion of MCPBA added (0.55 g, 3.16 mmol) and the heating continued for another 4 h. Sodium hydrogen carbonate was added to the cold mixture, stirred overnight and extracted with dichloromethane. The organic phase was washed with $Na_2SO_3$, brine and dried ($MgSO_4$). The crude product was purified by flash chromatography (silica gel) $CH_2Cl_2$:MeOH 9:1; yield 0.298 g, (49%) of a white crystalline material.

HRMS [M+1] 572.3456. Calc. for $C_{29}H_{49}N_1O_{10}$: 572.3456.

EXAMPLE 22

10,11-Epoxy-erythralosamine (41)

A solution of 10,11-epoxy-erythralosamine N-oxide (37) (0.380 g, 0.665 mmol) and triphenylphosphine (0.350 g, 1.33 mmol) in THF (5 ml) was heated at reflux for 17 h. Most of the THF was removed by distillation, the residual material extracted into ethyl acetate, the extracts shaken with aqueous sodium bicarbonate, washed with brine and dried ($MgSO_4$). The solution was evaporated and the residual material subjected to flash chromatography on silica gel using $CH_2Cl_2$: MeOH:$NH_3$ 90:8:2; yield 0.216 g (60%) of a white crystalline material.

HRMS: M 556.3474. Calc. for $C_{29}H_{49}NO_9$: 556.3480.

EXAMPLE 23

10,11-Anhydro-6-O-methyl-descladinosyl-erythromycin A (105)

A suspension of 6-O-methyl-erythromycin A (1.21 g, 1.60 mmol), ethylene carbonate (0.86 g, 9.70 mmol and triethylamine (5 ml) was refluxed with vigorous stirring for 24 h when more ethylene carbonate (0.43 g, 4.85 mmol) was added, and the reaction mixture was refluxed for an additional 20 h. Excess triethylamine was removed under reduced pressure, water (4 ml), 10% aqueous HCl (2 ml) and ethanol (0.5 ml) were added and the mixture was stirred at room temperature for 24 h. The pH was adjusted to 10-11 with aq. KOH. The mixture was extracted with EtOAc, the organic phase washed with brine, dried ($MgSO_4$) and concentrated to afford the crude product as a white solid mp 175-177° C.; yield 0.68 g (74%) after flash chromatography using $CH_2Cl_2$:MeOH:$NH_3$(aq) 90:4:2-90:10:2: HRMS [Electrospray, Na+]: M 594.3626. Calc. for $C_{30}H_{53}NO_9$: 594.3612.

EXAMPLE 24

10,11-Anhydro-6-O-methyl-descladinosyl-erythromycin A N-oxide (106)

Hydrogen peroxide (2.0 ml) was added to a solution of 10,11-anhydro-6-O-methyl-descladinosyl-erythromycin A (105) (1.60 g, 2.80 mmol) in methanol (20 ml). The reaction mixture was stirred at ambient temperature for 5 h. Cyclohexene (2 ml) was added to remove excess hydrogen peroxide and the reaction mixture was stirred at room temperature overnight. The solvents were removed under reduced pressure and the crude product was purified by flash chromatography using $CH_2Cl_2$:MeOH:$NH_3$(aq) 90:20:2; yield 1.11 g (68%) of a white crystalline material, mp. 192-193° C. HRMS [Electrospray, H+]: M 588.3727. Calc. for $C_{30}H_{53}NO_{10}$: 588.3742.

EXAMPLE 25

10-Acetoxymethyl-10,11-anhydro-10-desmethyl-6-O-methyl-descladinosyl-erythromycin A N-oxide (107)

NBS (1.00 g, 5.60 mmol) was added to a solution of the N-oxide (106) (1.11 g, 1.90 mmol) in acetic acid (10 ml) at room temperature and the mixture stirred at this temperature overnight. The solvent was removed under reduced pressure, the residual material dissolved in $CHCl_3$, washed with $NaHCO_3$, dried ($MgSO_4$) and concentrated to afford the crude product as a white solid, mp 154-157° C.; yield 0.995 g (80%) after flash chromatography using $CH_2Cl_2$:MeOH:$NH_3$(aq) 90:10:2. HRMS [Electrospray, H+]: M 646.3800 (Calc. for $C_{32}H_{55}NO_{12}$: 646.3797).

EXAMPLE 26

10-Acetoxymethyl-10,11-anhydro-10-desmethyl-6-O-methyl-descladinosyl-erythromycin A (108)

The N-oxide (107) (0.69 g, 0.001 mol) and triphenylphosphine (0.56 g, 0.003 mol) were heated under refluxed with stirring in THF overnight. The cold reaction mixture was extracted with EtOAc, the extracts washed with $NaHCO_3$, brine and dried ($MgSO_4$). The crude product was subjected to flash chromatography. (A simpler workup procedure is to remove the THF under reduced pressure and add the crude product onto the flash column) The product was obtained as a white solid, mp. 95-97° C.; yield 0.43 g (68%). HRMS [Electrospray, M+]:
M 652.3674. Calc. for $C_{32}H_{55}NO_{11}$: 652.3667.

EXAMPLE 27

10-Acetoxymethyl-2'O-acetyl-10,11-anhydro-10-desmethyl-6O-methyl-descladinosyl-erythromycin A (109)

A solution of the acetoxymethyl derivative (108) (0.35 g, 0.556 mmol), triethylamine (0.15 ml, 1.11 mmol) and acetic acid anhydride (0.10 ml, 1.11 mmol) in dichloromethane (10 ml) was stirred at room temperature for 17 h. The reaction mixture was concentrated under reduced pressure and the product was extracted into ethyl acetate, the solution washed with $NaHCO_3$, brine and dried ($MgSO_4$). The solution was evaporated and the residual material subjected to flash chromatography using acetone:hexane 1:2. The product was a white solid mp. 83-85° C.; yield 0.24 g (63%) HRMS [Electrospray, Na+]: M 694.3779 (Calc. for $C_{34}H_{57}NO_{12}$: 694.3773).

EXAMPLE 28

10-Acetoxymethyl-2'O-acetyl-10,11-anhydro-10-desmethyl-6O-methyl-3-oxo-descladinosyl-erythromycin A (110)

The 3-OH compound (109) (1.50 g, 2.30 mmol) was dissolved in dichloromethane (40 ml) and Dess-Martin periodinane reagent (1.40 g, 3.10 mmol) was added. The reaction mixture was stirred at room temperature for 2 h before the reaction mixture was concentrated under reduced pressure. The residual material was triturated with ethyl acetate, the solution washed with water/KOH (pH adjusted to 10-11), with brine and dried ($MgSO_4$). The crude product was subjected to flash chromatography using acetone:hexane 1:1. The product was a white solid, mp. 172-174° C., 0.93 g, (87%).
HRMS [Electrospray, Na+]: M 692.3586 (Calc. for $C_{34}H_{53}NO_{12}$: 692.3616).

EXAMPLE 29

10-Acetoxymethyl-10,11-anhydro-10-desmethyl-6-O-methyl-3-oxo-descladinosyl-erythromycin (111)

A solution of 10-acetoxymethyl-2'O-acetyl-10,11-anhydro-10-desmethyl-6-O-methyl-3-oxo-descladinosylerythromycin A (110) in methanol is stirred at room temperature overnight. The methanol is distilled off and the residual material subjected to flash chromatography on silica gel using $CH_2Cl_2$:MeOH:$NH_3$(aq) 90:8:2 to provide the title compound as a white solid.

EXAMPLE 30

10-hydroxymethyl-10-11-anhydro-10-desmethyl-6-O-methyl-descladinosyl-erythromycin A (112)

The allylic acetate (111) (0.045 g, 0.071 mmol) was dissolved in methanol (1 ml) and cooled to 0° C. Sodium methoxide (1 M) (0.09 ml, 0.086 mmol) was added slowly and the reaction mixture was stirred for 16 h. Two more portions of sodium methoxide was added over the next 2 days. TLC showed full conversion to the product after 3 days. The reaction mixture was quenched with sodium bicarbonate and the methanol removed under reduced pressure. The product was extracted with ethyl acetate and purified by flash chromatography using $CH_2Cl_2$:MeOH:$NH_3$ 90:10:2. The allylic alcohol

EXAMPLE 31

10-Acetoxymethyl-2'O-acetyl-10-desmethyl-12-O-(imidazolocarbonyl)-6-O-methyl-3-oxo-descladinosyl-erythromycin A (113)

1 M NaHMDS (1.6 ml, 1.50 mmol) THF was added dropwise over 30 min to a cold (−40° C.) solution of the ketolide (111) (0.887 g, 1.30 mmol) in THF (10 ml). The solution was stirred at this temperature for 45 min. A solution of carbonyl diimidazole (CDI) (0.843 g, 5.20 mmol) in THF (10 ml) and DMF (5 ml) was added dropwise over 30 min to the reaction mixture at room temperature. The reaction mixture was stirred at this temperature for 20 h and quenched with sodium bicarbonate at 0° C. The product was extracted with ethyl acetate, washed with water (pH 10-11), with brine and dried ($Na_2SO_4$). The crude product was subjected to flash chromatography using acetone:hexane 1:1. The product was a white foam; yield 0.37 g (45%). HRMS [Electrospray, Na+]: M 786.3778 (Calc. for $C_{38}H_{57}N_3O_{13}$: 786.3783).

EXAMPLE 32

2'O-Acetyl-11-amino-[11N-12O]-carbonyl-11-deshydroxy-10-desmethyl-10-methylene-6-O-methyl-3-oxo-descladinosyl-erythromycin (114)

Ammonia (aq) (0.2 ml) was added to a solution of the imidazole derivative (113) (0.127 g, 0.166 mmol) in acetonitrile (2 ml) and THF (0.2 ml) and the mixture stirred at room temperature for 24 h. The reaction mixture was concentrated under reduced pressure and the residual material triturated with ethyl acetate, the solution washed with water/KOH (pH adjusted to 10-11), with brine and dried ($MgSO_4$). The solution was evaporated and the residual material subjected to flash chromatography using acetone:hexane initially 2:1, then 1:1. The product was a white solid, mp. 142-145° C.; yield 0.042 g (38%). HRMS [Electrospray, H+]: M 653.3627 (Calc. for $C_{33}H_{52}N_2O_{11}$: 653.3643).

EXAMPLE 33

11-Amino-[11N-12O]carbonyl-11-deshydroxy-10-desmethyl-10-methylene-6-O-methyl-3-oxo-descladinosyl-erythromycin A (115)

Methanol (2 ml) was added to the cyclic carbamate (114) (0.072 g, 0.11 mmol) and the mixture stirred at room temperature overnight. The methanol was removed under reduced pressure and the crude product was purified by flash chromatography on silica gel using $CH_2Cl_2$:MeOH:$NH_3$(aq) 90:8:2. The product was a white solid, mp. 161-163° C.; yield 0.046 g, (68%). HRMS [Electrospray, H+]: M 611.3525 (Calc. for $C_{31}H_{50}N_2O_{10}$: 611.3538).

EXAMPLE 34

2'O-Acetyl-11-benzylamino-[11N-12O]-carbonyl-11-deshydroxy-10-desmethyl-10-methylene-6-O-methyl-3-oxo-descladinosyl-erythromycin A (116a)

Benzylamine (0.12 ml, 1.13 mmol) was added to a solution of the imidazole derivative (113) (172 mg, 0.225 mmol) in acetonitrile (2 ml) and THF (0.2 ml) and the mixture stirred at room temperature for 21 h. The reaction mixture was concentrated under reduced pressure and the residual material triturated with ethyl acetate, the solution washed with water/KOH (pH adjusted to 10-11), with brine and dried ($MgSO_4$). The solution was evaporated and the residual material subjected to flash chromatography using acetone:hexane, initially 2:1 and then 1:1. The product was a yellow oil; yield 100 mg (60%). HRMS [Electrospray, H+]: M 743.4132 (Calc. for $C_{40}H_{58}N_2O_{11}$: 743.4113).

EXAMPLE 35

2'O-Acetyl-11-(4-phenylbut-1-yl-amino)-[11N-12O]-carbonyl-11-deshydroxy-10-desmethyl-10-methylene-6-O-methyl-3-oxo-descladinosyl-erythromycin A (116b)

4-Phenylbutane-1-amine (0.08 ml, 0.524 mmol) was added to a solution of the imidazole derivative (113) (100 mg, 0.131 mmol) in acetonitrile (3 ml) and THF (0.2 ml) and the mixture was stirred at 65° C. for 20 h. The reaction mixture was concentrated under reduced pressure and the residual material triturated with ethyl acetate, the solution washed with water/KOH (pH adjusted to 10-11), with brine and dried ($MgSO_4$). The solution was evaporated and the residual material was subjected to flash chromatography using acetone:hexane, initially 2:1 and then 1:1. The product was a yellow oil; yield 83 mg (76%). HRMS [Electrospray, Na+]: M 807.4 (Calc. for $C_{40}H_{58}N_2O_{11}$)

EXAMPLE 36

11-Benzylamino-[11N-12O]-carbonyl-11-deshydroxy-10-desmethyl-10-methylene-6-O-methyl-3-oxo-descladinosyl-erythromycin A (117)

A solution of 2'O-acetyl-11-benzylamino-[11N-12O]-carbonyl-11-deshydroxy-10-desmethyl-10-methylene-6-O-methyl-3-oxo-descladinosyl-erythromycin A (116a) in methanol (5 ml) was stirred at room temperature for 17 h. The solvent was removed under reduced pressure. Evaporation of the solvent left the title compound as a yellow oil. HRMS [H+]: M 701.4011 (Calc. for $C_{38}H_{56}N_2O_{10}$ 701.4007).

EXAMPLE 37

11-Amino-[11N-12O]carbonyl-11-deshydroxy-10-desmethyl-6-O-methyl-3-oxo-10-benzylaminomethyl-descladinosyl-erythromycin A (118a)

A solution of benzylamine (0.13 ml, 1.18 mmol) and 11-amino-[11N-12O]carbonyl-11-deshydroxy-10-desmethyl-6-O-methyl-3-oxo-descladinosyl-erythromycin A (115) (0.257 g, 3.39 mmol) in THF (4 ml) was heated at reflux for 17 h. Another portion of benzylamine (0.13 ml, 1.18 mmol) was added and the solution heated for another 24 hours. The solution was concentrated at reduced pressure and the residual material extracted with ethyl acetate, the solution washed with $NaHCO_3$, with brine and dried ($MgSO_4$). The solution was evaporated and the residual material was subjected to flash chromatography on silica gel using acetone:hexane 1:1. The product was a white solid with mp 185-187° C.; yield 0.150 g (48%) HRMS [H+]: M 618.4273 (Calc. for $C_{38}H_{59}N_3O_{10}$: 718.4273).

was a white solid 0.030 g (71%) with mp 205-206° C. HRMS [Electrospray, Na+]: M 610.3558 (Calc. for $C_{30}H_{53}NO_{10}$: 610.3561).

EXAMPLE 38

11-Amino-[11N-12O]carbonyl-11-deshydroxy-10-desmethyl-6-O-methyl-3-oxo-10-(3-phenylprop-1-yl-aminomethyl)-descladinosyl-erythromycin A (118b)

A solution of 3-phenylpropane-1-amine (1.2 mmol) and 11-amino-11N-12O]carbonyl-11-deshydroxy-10-desmethyl-6-O-methyl-3-oxo-descladinosyl-erythromycin A (115) (1 mmol) in DMF (5 ml) was heated at 60° C. for 4 h. The cold solution was taken into ethyl acetate, the acetate solution washed with brine, dried ($Na_2SO_4$), evaporated and the product isolated from the residual material after flash chromatography on silica gel using $CH_2Cl_2$:MeOH 9:1.

EXAMPLE 39

10,11-Anhydro-10-azidomethyl-10-desmethyl-6-O-methyl-descladinosyl-erythromycin A (120)

A solution of the descladinosyl-erythromycin allylic acetate (109) (0.048 g, 0.076 mmol) and $NaN_3$ (0.010 g, 0.152 mmol) in THF (1 ml)/DMF (5 ml) was heated at 70° C. for 17 h. The solution was concentrated at reduced pressure and the residual material extracted with ethyl acetate, the solution washed with $NaHCO_3$, with brine and dried ($MgSO_4$). The solution was evaporated and the residual material was subjected to flash chromatography on silica gel using $CH_2Cl_2$:MeOH:$NH_3$(aq) initially 90:4:2, then 90:8:2. The product was a white solid, mp. 98-100° C.; yield 0.022 g (68%) HRMS [M+]: M 613.3796 (Calc. for $C_{30}H_{52}N_4O_9$: 613.3807).

EXAMPLE 40

2'-O-Acetyl-10,11-anhydro-10-azidomethyl-10-desmethyl-6-O-methyl-descladinosyl-erythromycin A (121)

10,11-Anhydro-10-azidomethyl-10-desmethyl-6-O-methyl-descladinosyl-erythromycin A (120) (0.239 g, 0.390 mmol) was dissolved in dichloromethane (3 ml). Triethylamine (0.11 ml, 0.780 mmol) and acetic acid anhydride (0.07 ml, 0.780 mmol) were added. The reaction mixture was stirred at ambient temperature for 15 h. The reaction mixture was concentrated under reduced pressure and the product was extracted with ethyl acetate and washed with $NaHCO_3$, brine and dried ($MgSO_4$). The crude product was subjected to flash chromatography using gradient elution with acetone:hexane (1:2-1:1) as eluent. The phases were concentrated to afford the product as a white solid, mp. 170-172° C., yield 0.136 g (54%). HRMS [H+]: M 655.3928 (Calc. for $C_{32}H_{54}N_4O_{10}$ 655.3912).

EXAMPLE 41

2'-O-Acetyl-10,11-anhydro-10-azidomethyl-10-desmethyl-6-O-methyl-3-oxo-descladinosyl-erythromycin A (122)

The Dess-Martin periodinane reagent (0.140 g, 0.324 mmol) was added to a solution of 2'O-acetyl-10,11-anhydro-10-azidomethyl-10-desmethyl-6-O-methyl-descladinosyl-erythromycin A (121) (0.106 g, 0.162 mmol) in dichloromethane (2 ml). The reaction mixture was stirred at room temperature for 2 h, concentrated under reduced pressure, the residual material dissolved in ethyl acetate, the solution washed with water/KOH (pH adjusted to 10-11), with brine and dried ($MgSO_4$) before evaporation. The product was isolated after flash chromatography of the residual material using gradient elution with acetone:hexane 2:1-1:1. The product was a white solid which was crystallized from diethyl ether and hexane, mp. 110-115° C., yield 0.079 g (75%). HRMS [Na+]: M 675.3608 (Calc. for $C_{32}H_{52}N_4O_{10}$ 675.3575).

EXAMPLE 42

2'-O-Acetyl-10,11-anhydro-10-azidomethyl-10-desmethyl-12-O-(imidazolocarbonyl)-6-O-methyl-3-oxo-descladinosyl-erythromycin A (123)

2'-O-Acetyl-10,11-anhydro-10-azidomethyl-10-desmethyl-6-O-methyl-3-oxo-descladinosyl-erythromycin A (112) (0.044 g, 0.067 mmol) in THF (2 ml) at 0° C. was added to NaH (0.006 g, 0.2002 mmol). Carbonyl diimidazole (CDI) dissolved in THF (1 ml) was added dropwise over 5 min to the reaction mixture. The solution was stirred for 17 h and the reaction mixture was cooled to 0° C. again before it was quenched with sodium bicarbonate and extracted with ethyl acetate and washed with water (pH 10-11), with brine and dried ($Na_2SO_4$). The crude product was a white solid, yield 0.050 g (98%). HRMS [Na+]: M 769.3760 (Calc. for $C_{36}H_{54}N_6O_{11}$ 769.3742). (The crude product was used without purification).

EXAMPLE 43

10-Acetoxymethyl-10,11-anhydro-10-desmethyl-6-O-methyl-2',3,12-$O_3$-trimethylsilyl-descladinosyl-erythromycin A (124)

A solution of the descladinosyl-erythromycin allylic acetate (109) (0.069 g, 0.110 mmol) and BSTFA (0.29 ml, 1.10 mmol) in pyridine (0.22 ml) under argon was stirred at room temperature for 48 h. The solution was evaporated to dryness under reduced pressure, the residual material extracted into ethyl acetate, the solution washed with $NaHCO_3$, with brine and dried ($MgSO_4$). The residual material was subjected to flash chromatography on silica gel using acetone:hexane 1:4. The product was a white foam, yield 0.036 g (40%). HRMS [Electrospray, H+]: M 846.5065 (Calc. for $C_{44}H_{79}NO_{11}Si_3$: 846.5033).

EXAMPLE 44

10,11-Anhydro-10-desmethyl-10-ethyl-6-O-methyl-2',3,12-$O_3$-trimethylsilyl-descladinosyl-erythromycin A (125)

Tris(2-furyl)phosphine (TFP) (0.002 g, 0.008 mmol) and $Pd_2$ $dba_3$.$CHCl_3$ (0.002 g, 0.002 mmol) were added to a deoxygenated solution of 2',3,12-$O_3$-trimethylsilyl-descladinosyl-erythromycin (124) (0.070 g, 0.083 mmol) in NMP (1 ml) under argon and the solution was heated at 50° C. for 10 min to generate the catalyst. Subsequently, a solution of trimethylaluminium in THF (2 M, 0.21 ml, 0.414 mmol) was added. The resultant mixture was heated at 70° C. for 24 h. The solvent was removed at reduced pressure, the residue extracted into ethyl acetate, the solution shaken with aqueous sodium hydrogen carbonate, with brine, dried ($MgSO_4$), evaporated and the residual material subjected to flash chromatography on silica gel to give 0.007 g (10%) of a white crystalline material. HRMS [Electrospray, H+]: M 802.5140 (Calc. for $C_{41}H_{79}NO_9Si_3$: 802.5135).

EXAMPLE 45

10,11-Anhydro-10-desmethyl-10-ethyl-6-O-methyl-descladinosyl-erythromycin A (126)

TBAF in THF (2.0 mmol, 2 ml) is added to a solution of 10,11-anhydro-10-desmethyl-10-ethyl-6-O-methyl-2',3,12-$O_3$-trimethylsilyl-descladinosyl-erythromycin A (125) (0.5 mmol) in THF (10 ml) at 0° C. The mixture is stirred at this temperature for 30 min and at room temperature overnight. The solvent is then distilled off, and the residual material is subjected to flash chromatography on silica gel using $CH_2Cl_2$:MeOH:$NH_3$ (aq) 90:6:2.

EXAMPLE 46

10,11-Anhydro-2'O-benzoyl-10-desmethyl-10-ethyl-6-O-methyl-descladinosyl-erythromycin A (127)

A solution of 10,11-anhydro-10-desmethyl-10-ethyl-6-O-methyl-descladinosyl-erythromycin A (126), (0.5 mmol), benzoic anhydride (1.5 mmol), triethylamine (2 mmol) and DMAP (2 mmol) in dichloromethane (10 ml) is stirred at room temperature overnight. The reaction mixture is shaken with 5% aqueous sodium carbonate, the organic solution dried ($Na_2SO_4$) and the solution evaporated to dryness. The residual material is subjected to flash chromatography on silica gel using dichloromethane.

EXAMPLE 47

10,11-Anhydro-2'O-benzoyl-10-desmethyl-10-ethyl-6-O-methyl-3-oxo-descladinosyl-erythromycin A (128)

The Dess-Martin periodinane reagent (3.0 mmol) is added to a solution of 10,11-anhydro-2'O-benzoyl-10-desmethyl-10-ethyl-6-O-methyl-descladinosyl-erythromycin A (127) (2.0 mmol) in dichloromethane (30 ml). The reaction mixture is stirred at room temperature for 2 h before the reaction mixture is concentrated under reduced pressure. The residual material is triturated with ethyl acetate, the solution washed with water/KOH (pH adjusted to 10-11), with brine and dried ($MgSO_4$). The crude product is subjected to flash chromatography using acetone:hexane 1:1 to provide the title compound.

EXAMPLE 48

10,11-Anhydro-10-desmethyl-6-O-methyl-10-(3-phenylprop-2-yn-1-yl)-descladinosyl-erythromycin A (129)

Tris(2-furyl)phosphine (0.007 g, 0.032 mmol) and $Pd_2$ $dba_3$.$CHCl_3$ (0.004 g, 0.004 mmol) was added to a deoxygenated solution of 10-acetoxymethyl-10,11-anhydro-10-desmethyl-6-O-methyl-descladinosyl-erythromycin A (109) (0.100 g, 0.159 mmol) in NMP (1 ml) under argon and the solution heated at 50° C. for 10 min to generate the catalyst system. Subsequently, a solution of tributyl(phenylethynyl) tin (0.07 ml, 0.191 mmol) was added and the resultant mixture was heated at 80° C. for 24 h. The solvent was removed under reduced pressure, the residue extracted into ethyl acetate, the solution shaken with aqueous sodium hydrogen carbonate, with brine, dried ($MgSO_4$), evaporated and the residual material subjected to flash chromatography on silica gel to give 0.035 g (33%) of a yellow oil. HRMS [Electrospray, H+]: M 672.4120 (Calc. for $C_{38}H_{57}NO_9$: 672.4106).

EXAMPLE 49

2'O-Acetyl-10,11-anhydro-10-desmethyl-10-ethyl-6-O-methyl-descladinosyl-erythromycin A (130)

A solution of 10,11-anhydro-10-desmethyl-10-ethyl-6-O-methyl-descladinosyl-erythromycin A (126) (0.6 mmol), triethylamine (0.16 ml, 1.2 mmol) and acetic acid anhydride (1.2 mmol) in dichloromethane (10 ml) is stirred at room temperature for 17 h. The reaction mixture is concentrated under reduced pressure and the product extracted into ethyl acetate, the solution washed with $NaHCO_3$, brine and dried ($MgSO_4$). The solution is evaporated and the residual material subjected to flash chromatography on silica gel using acetone:hexane 1:1.

EXAMPLE 50

2'O-Acetyl-10,11-anhydro-10-desmethyl-10-ethyl-6-O-methyl-3-oxo-descladinosyl-erythromycin A (131)

The Dess-Martin periodinane reagent (3.10 mmol) is added to a solution of 2'O-acetyl-10,11-anhydro-10-desmethyl-10-ethyl-6-O-methyl-descladinosylerythromycin A (130) (2.30 mmol) in dichloromethane (40 ml). The reaction mixture is stirred at room temperature for 2 h, concentrated under reduced pressure, the residual material triturated with ethyl acetate, the solution washed with water/KOH (pH adjusted to 10-11), with brine and dried ($MgSO_4$) before evaporation. The product is isolated after flash chromatography of the residual material using acetone:hexane 1:1.

EXAMPLE 51

2'O-Acetyl-10,11-anhydro-10-desmethyl-10-ethyl-12-O-(imidazolocarbonyl)-6-O-methyl-3-oxo-descladinosyl-erythromycin A (132)

1 M NaHMDS (1.6 ml, 1.50 mmol) in THF is added dropwise over 30 min to a cold (−40° C.) solution of 2'O-acetyl-10,11-anhydro-10-desmethyl-10-ethyl-6-O-methyl-3-oxo-descladinosyl-erythromycin A (131) (1.30 mmol) in THF (10 ml). The solution is stirred at this temperature for 45 min. A solution of carbonyl diimidazole (CDI) (5.20 mmol) in THF (10 ml) and DMF (5 ml) is added dropwise over 30 min to the reaction mixture at room temperature. The reaction mixture is stirred at this temperature for 20 h and quenched with sodium bicarbonate at 0° C. The reaction mixture is extracted with ethyl acetate, the organic solution washed with water (pH 10-11), with brine and dried ($Na_2SO_4$). The crude product is subjected to flash chromatography using acetone:hexane 1:1.

EXAMPLE 52

2'O-Acetyl-11-amino-[11N=12-O]carbonyl-11-deshydroxy-10-desmethyl-10-ethyl-6-O-methyl-3-oxo-descladinosyl-erythromycin A (133)

Ammonia (aq) (0.2 ml) is added to a solution of 2'O-acetyl-10,11-anhydro-10-desmethyl-10-ethyl-12-O-(imidazolocarbonyl)-6-O-methyl-3-oxo-descladinosyl-erythromycin A (132)(0.17 mmol) in acetonitrile (2 ml) and THF (0.2 ml) and the mixture stirred at room temperature for 24 h. The reaction mixture is concentrated under reduced pressure and the residual material triturated with ethyl acetate. The solution is washed with water/KOH (pH adjusted to 10-11), with brine and dried (MgSO$_4$). The solution is evaporated and the residual material subjected to flash chromatography using acetone:hexane, initially 2:1, then 1:1.

EXAMPLE 53

11-Amino-[11N-12O]carbonyl-11-deshydroxy-10-desmethyl-10-ethyl-6-O-methyl-3-oxo-descladinosyl-erythromycin A (134)

A solution of 2'O-acetyl-11-amino-[11N-12O]carbonyl-11-deshydroxy-10-desmethyl-10-ethyl-6-O-methyl-3-oxo-descladinosyl-erythromycin A (133) in methanol is stirred at room temperature overnight. The methanol is distilled off and the residual material subjected to flash chromatography on silica gel using CH$_2$Cl$_2$:MeOH:NH$_3$ (aq) 90:8:2 to provide the title compound.

EXAMPLE 54

10,11-Anhydro-2'O-benzoyl-10-desmethyl-10 ethyl-12-O-(imidazolocarbonyl)-6-O-methyl-oxo-descladinosyl-erythromycin A (135)

1 M NaHMDS (1.50 mmol) THF is added dropwise over 30 min to a cold (−40° C.) solution of 10,11-anhydro-2'O-benzoyl-10-desmethyl-10-ethyl-6-O-methyl-3-oxo-descladinosyl-erythromycin A (128) (1.30 mmol) in THF (10 ml). The solution is stirred at this temperature for 45 min. A solution of carbonyl diimidazole (CDI) (5.20 mmol) in THF (10 ml) and DMF (5 ml) is added dropwise over 30 min to the reaction mixture at room temperature. The reaction mixture is stirred at this temperature for 20 h and the reaction quenched with sodium bicarbonate at 0° C. The mixture is extracted with ethyl acetate, washed with water (pH 10-11), with brine and dried (Na$_2$SO$_4$). The pure title compound is obtained after flash chromatography of the crude product using acetone:hexane 1:1.

EXAMPLE 55

11-Amino-[11N-12O]carbonyl-N11-amino-2'O-benzoyl-11-deshydroxy-10-desmethyl-10-ethyl-6-O-methyl-oxo-descladinosyl-erythromycin A (136)

Hydrazine hydrate (1.6 mmol) is added to a solution of 10,11-anhydro-2'O-benzoyl-10-desmethyl-10 ethyl-12-O-(imidazolocarbonyl)-6-O-methyl-3-oxo-descladinosyl-erythromycin A (135) (0.4 mmol) in DMF (5 ml) and the resultant solution stirred at room temperature for 3 h. The reaction mixture is taken up into ethyl acetate, the resultant solution washed with water and brine, dried (Na$_2$SO$_4$) and evaporated. The residual material is purified by flash chromatography on silica gel using hexane:EtOAc 5:2 with 2% NEt$_3$.

EXAMPLE 56

11-Amino-[11N-12O]carbonyl-2'O-benzoyl-11-deshydroxy-10-desmethyl-10-ethyl-6-O-methyl-3-oxo-N$^{11}$-[3-(4-quinolinyl) propylamino]-descladinosyl-erythromycin A (137)

Acetic acid (10 ml) is added to a solution of 11-amino-[11N-12O]carbonyl-N$^{11}$-amino-2'O-benzoyl-11-Deshydroxy-10-desmethyl-10-ethyl-6-O-methyl-3-oxo-descladinosyl-erythromycin A (136) (1 mmol) and 3-(4-quinolinyl) propanal (1.2 mmol) in methanol (4 ml). The solution is stirred at room temperature for 5 h before sodium cyanoborohydride (2 mmol) is added. The reaction mixture is stirred at room temperature overnight before the reaction is quenched by addition of saturated aqueous sodium carbonate and the reaction mixture poured into ethyl acetate. The phases are separated, the organic phase washed with brine, dried (Na$_2$SO$_4$) and evaporated. The product is isolated after flash chromatography on silica gel using hexane:EtOAc 1:1 with 2% Et$_3$N.

EXAMPLE 57

11-Amino-[11N-12O]carbonyl-11-deshydroxy-10-desmethyl-10-ethyl-6-O-methyl-3-oxo-N$^{11}$-[3-(4-quinolinyl) propylamino]-descladinosyl-erythromycin A (138)

A solution of 11-amino-[11N-12O]carbonyl-2'O-benzoyl-11-deshydroxy-10-desmethyl-10-ethyl-6-O-methyl-3-oxo-N$^{11}$-[3-(4-quinolinyl)propylamino]-descladinosyl-erythromycin A (137) (1 mmol) in methanol (10 ml) is heated under reflux for 15 h before the solution is evaporated to dryness. The solid title compound is isolated from the residual material after flash chromatography on silica gel using hexane:EtOAc 2:3 with 2% Et$_3$N.

EXAMPLE 58

11-Amino-[11N-12O]carbonyl-2'O-benzoyl-11-deshydroxy-10-desmethyl-10-ethyl-6-O-methyl-3-oxo-N$^{11}$-4-[4-(3-pyridinyl)imidazolyl]butyl-descladinosyl-erythromycin A (139)

4-[4-(3-Pyridinyl)imidazolyl]butylamine (1.6 mmol) is added to a solution of 10,11-anhydro-2'O-benzoyl-10-desmethyl-10-ethyl-12-O-(imidazolocarbonyl)-6-O-methyl-3-oxo-descladinosyl-erythromycin A (135) (0.4 mmol) in wet acetonitrile (10 ml). The reaction mixture is stirred at 60° C. for 3 d and taken up in ethyl acetate. The resulting mixture is washed with 5% NaOH, dried (Na$_2$SO$_4$) and evaporated. The residual material is purified by flash chromatography on silica gel using acetone:hexane 1:1.

EXAMPLE 59

11-Amino-[11N-12O]carbonyl-11-deshydroxy-10-desmethyl-10-ethyl-6-O-methyl-3-oxo-N11-[4-(3-pyridinyl) imidazolyl]butyl-descladinosyl-erythromycin A (140)

A solution of 11-amino-[11N-12O]carbonyl-2'O-benzoyl-11-deshydroxy-10-desmethyl-10-ethyl-6-O-methyl-3-oxo-N$^{11}$-4-[4-(3-pyridinyl)imidazolyl]butyl-descladinosyl-erythromycin A (139) in methanol is heated under reflux for 10 h. Evaporation of the solvent and flash chromatography of the residual material on a silica gel column using CH$_2$Cl$_2$:MeOH 9:1 provides the pure title compound.

In Examples 60 to 63, the active substance used is preferably the compound of Example 118b.

EXAMPLE 60

Tablets Containing 50 mg of Active Substance

Composition:

| active substance | 50 mg |
|---|---|
| lactose | 120 mg |
| maize starch | 40 mg |
| magnesium stearate | 2 mg |
| Povidone K 25 | 18 mg |

The active substance, lactose and maize starch are homogeneously mixed; granulated with an aqueous solution of Povidone; mixed with magnesium stearate; and compressed in a tablet press. Weight of tablet 230 mg.

EXAMPLE 61

Capsules Containing 50 mg Active Substance

Composition:

| active substance | 50 mg |
|---|---|
| maize starch | 80 mg |
| highly dispersed silica | 5 mg |
| magnesium stearate | 2.5 mg |

The active substance, maize starch and silica are homogeneously mixed; mixed with magnesium stearate; and the mixture is packed into hard gelatine capsules in a capsule filling machine.

EXAMPLE 62

Suppositories Containing 50 mg of Active Substance

Composition:

| active substance | 50 mg |
|---|---|
| hard fat q.s. ad | 1700 mg |

Hard fat is melted at about 38° C.; ground active substance is homogeneously dispersed in the molten hard fat; and after cooling to about 35° C. it is poured into chilled moulds.

EXAMPLE 63

Injectable Solution Containing 10 mg of Active Substance per 1 ml

Composition:

| active substance | 10 mg |
|---|---|
| mannitol | 50 mg |
| human serum albumin | 10 mg |
| water for injections ad | 1 ml |

Mannitol is dissolved in water for injections; human serum albumin is added; the active ingredient is dissolved with heating; the solution is made up to the specified volume with water for injections and transferred into ampoules under nitrogen gas.

unsaturated macrolide analog, for use as an intermediate.

The invention claimed is:

1. A 10-substituted-10-desmethyl macrolide of formula II, IV or V

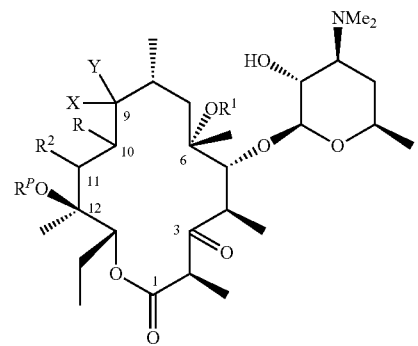

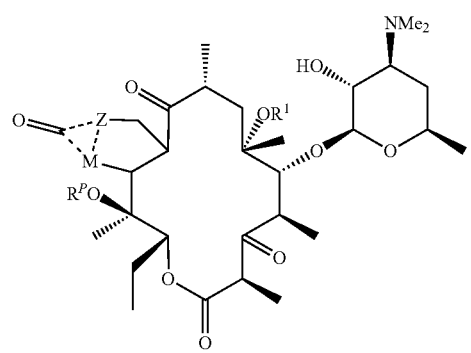

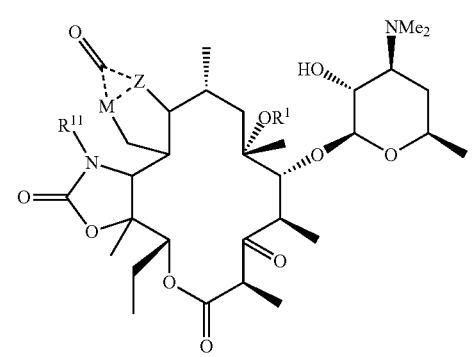

$R^{11} = R^4, NR^7R^8$ wherein R is selected from the group consisting of
  (1) methyl substituted with one or more substituents selected from the group consisting of
    (i) CN,
    (ii) F,
    (iii) $CO_2R^3$ wherein $R^3$ is selected from hydrogen, $C_1$-$C_3$-alkyl or aryl substituted $C_1$-$C_3$-alkyl, or heteroaryl substituted $C_1$-$C_3$-alkyl,
    (iv) $OR^4$ wherein $R^4$ is selected from hydrogen, $C_1$-$C_4$-alkyl or aryl substituted $C_1$-$C_4$-alkyl, or heteroaryl substituted $C_1$-$C_4$-alkyl, heterocycloalkyl and optionally substituted cycloalkyl, $C_1$-$C_3$-alkoxy-$C_1$-$C_3$-alkoxy, $C_2$-$C_4$-alkenyl or aryl substituted $C_2$-$C_4$-alkenyl, or heteroaryl substituted $C_2$-$C_4$-alkenyl, heterocycloalkyl and optionally substituted cycloalkyl, aryl or optionally substituted aryl, heteroaryl or optionally substituted heteroaryl,
(v) $S(O)_nR^3$ wherein n=0, 1 or 2 and $R^3$ is as previously defined
(vi) $NR^4C(O)R^3$ wherein $R^3$ and $R^4$ are as previously defined
(vii) $NR^4C(O)NR^5R^6$ wherein $R^4$ is defined as defined previously, and $R^5$ and $R^6$ are independently selected from hydrogen, $C_1$-$C_3$-alkyl, $C_1$-$C_3$ alkyl substituted with aryl, substituted aryl, heteroaryl, substituted heteroaryl
(viii) $NR^7R^8$ wherein $R^7$ and $R^8$ are independently selected from the group consisting of
(a) hydrogen
(b) $C_1$-$C_{12}$-alkyl, and optionally substituted $C_1$-$C_{12}$-alkyl
(c) $C_2$-$C_{12}$-alkenyl, and optionally substituted $C_2$-$C_{12}$-alkenyl
(d) $C_2$-$C_{12}$-alkynyl, and optionally substituted $C_2$-$C_{12}$-alkynyl
(e) aryl, and optionally substituted aryl
(f) heteroaryl, and optionally substituted heteroaryl
(g) heterocycloalkyl, and optionally substituted heterocycloalkyl
(h) $C_1$-$C_{12}$ alkyl substituted with aryl, and optionally substituted with substituted aryl
(i) $C_1$-$C_{12}$ alkyl substituted with heteroaryl, and optionally substituted with substituted heteroaryl
(j) $C_1$-$C_{12}$ alkyl substituted with heterocycloalkyl, and with optionally substituted heterocycloalkyl, and
(k) $R^7$ and $R^8$ taken together with the atom to which they are attached form a 3-10-membered heterocycloalkyl ring which may contain one or more additional heteroatoms and may be substituted with one or more substituents independently selected from the group consisting of
(aa) halogen, hydroxy, $C_1$-$C_3$-alkoxy, alkoxy-$C_1$-$C_3$-alkoxy, oxo, $C_1$-$C_3$-alkyl, aryl and optionally substituted aryl, heteroaryl and optional substituted heteroaryl
(bb) $CO_2R^3$ wherein $R^3$ is as previously defined, and
(cc) $C(O)NR^5R^6$ wherein $R^5$ and $R^6$ are as previously defined,
(ix) aryl, and optionally substituted aryl, and
(x) heteroaryl, and optionally substituted heteroaryl,
(2) $C_2$-$C_{10}$-alkyl,
(3) $C_2$-$C_{10}$-alkyl substituted with one or more substituents selected from the group consisting of
(i) halogen,
(ii) $OR^4$ wherein $R^4$ is as defined previously
(iii) —CHO,
(iv) oxo,
(v) $NR^7R^8$ wherein $R^7$ and $R^8$ are defined as previously
(vi) =N—O—$R^4$ is wherein $R^3$ is as previously defined
(vii) —CN
(viii) —$S(O)_nR^3$ wherein n=0, 1 or 2 and $R^3$ is as previously defined
(ix) aryl, and optionally substituted aryl
(x) heteroaryl, and optionally substituted heteroaryl
(xi) $C_3$-$C_8$-cycloalkyl, and optionally substituted $C_3$-$C_8$-cycloalkyl
(xii) heterocycloalkyl, and optionally substituted heterocycloalkyl
(xiii) $NR^4C(O)R^3$ where $R^3$ and $R^4$ are as previously defined
(xiv) $NR^4C(O)NR^5R^6$ wherein $R^4$, $R^5$ and $R^6$ are as previously defined
(xv) =N—$NR^7R^8$ wherein $R^7$ and $R^8$ are as previously defined
(xvi) =N—$R^4$ wherein $R^4$ is as previously defined
(xvii) =N—$NR^4C(O)R^3$ wherein $R^3$ and $R^4$ are as previously defined, and
(xviii) =N—$NR^4C(O)NR^5R^6$ wherein $R^4$, $R^5$ and $R^6$ are as previously defined,
(4) $C_2$-$C_{10}$-alkenyl,
(5) $C_2$-$C_{10}$-alkenyl substituted with one or more substituents selected from the group consisting of
(i) halogen,
(ii) $OR^4$ wherein $R^4$ is as previously defined
(iii) O—$S(O)_nR^3$ where n and $R^3$ are as previously defined
(iv) —CHO,
(v) oxo,
(vi) —$CO_2R^3$ where $R^3$ is as previously defined
(vii) —$C(O)$—$R^4$ where $R^4$ is as previously defined
(viii) —CN
(ix) aryl, and optionally substituted aryl
(x) heteroaryl, and optionally substituted heteroaryl
(xi) $C_3$-$C_7$-cycloalkyl
(xii) $C_1$-$C_{12}$-alkyl substituted with heteroaryl
(xiii) $NR^7R^8$ wherein $R^7$ and $R^8$ are as previously defined
(xiv) $NR^4C(O)R^3$ where $R^3$ and $R^4$ are as previously defined
(xv) $NR^4C(O)NR^5R^6$ where $R^4$, $R^5$ and $R^6$ are as previously defined
(xvi) =N—O—$R^4$ where $R^4$ is as previously defined
(xvii) =N—$NR^7R^8$ wherein $R^7$ and $R^8$ are as previously defined
(xviii) =N—$NR^4$ wherein $R^4$ is as previously defined
(xix) =N—$NR^4C(O)R^3$ wherein $R^3$ and $R^4$ are as previously defined, and
(xx) =N—$NR^4C(O)NR^5R^6$ wherein $R^4$, $R^5$ and $R^6$ are as previously defined,
(6) $C_2$-$C_{10}$-alkynyl
(7) $C_2$-$C_{10}$-alkynyl substituted with one or more substituents selected from the group consisting of
(i) trialkylsilyl
(ii) halogen,
(iii) —CN
(iv) $OR^4$ where $R^4$ is defined as previously
(v) —CHO,
(vi) oxo,
(vii) —$CO_2R^3$ where $R^3$ is as previously defined
(viii) —$C(O)NR^5R^6$ wherein $R^5$ and $R^6$ are as previously defined
(ix) $NR^7R^8$ wherein $R^7$ and $R^8$ are as previously defined
(x) O—$S(O)_nR^3$ where n and $R^3$ are as previously defined
(xi) $C_3$-$C_7$-cycloalkyl
(xii) $C_1$-$C_{12}$-alkyl substituted with heteroaryl
(xiii) aryl, and optionally substituted aryl
(xiv) heteroaryl, and optionally substituted heteroaryl
(xv) $NR^4C(O)R^3$ where $R^3$ and $R^4$ are as previously defined
(xvi) $NR^4C(O)NR^5R^6$ where $R^4$, $R^5$ and $R^6$ are as previously defined
(xvii) =N—O—$R^4$ where $R^4$ is as previously defined
(xviii) =N—$NR^7R^8$ wherein $R^7$ and $R^8$ are as previously defined
(xix) =N—$NR^4C(O)R^3$ wherein $R^3$ and $R^4$ are as previously defined, and
(xx) =N—$NR^4C(O)NR^5R^6$ wherein $R^4$, $R^5$ and $R^6$ are as previously defined,
(8) cyclic substituents
(i) aryl, and optionally substituted aryl
(ii) heteroaryl, and optionally substituted heteroaryl
(iii) heterocycloalkyl, and optionally substituted heterocycloalkyl, and (iv) $C_3$-$C_7$-cycloalkyl, and optionally substituted $C_3$-$C_7$-cycloalkyl, and
(9) $C_1$ substituents with the exception of 10-methyl derivatives which are part of the above definitions under (1)
(i) —CHO
(ii) —CN
(iii) $CO_2R^3$ wherein $R^3$ is as previously defined
(iv) $C(O)NR^5R^6$ wherein $R^5$ and $R^6$ are as previously defined
(v) $C(S)NR^5R^6$ wherein $R^5$ and $R^6$ are as previously defined
(vi) $C(NR^4)NR^5R^6$ wherein $R^4$, $N^5$ and $R^6$ are as previously defined
(vii) CH=N—O—$R^4$ wherein $R^4$ is as previously defined
(viii) CH=N—$R^4$ is wherein $R^4$ is as previously defined
(ix) CH=N—$NR^7R^8$ wherein $R^7$ and $R^8$ are as previously defined
(x) CH=N—$NR^4C(O)R^3$ wherein $R^3$ and $R^4$ are as previously defined, and
(xi) CH=N-$NR^4C(O)NR^5R^6$ wherein $R^4$, $R^5$ and $R^6$ are as previously defined;
$R^1$ is selected from the group consisting of
(1) H
(2) methyl
(3) methyl substituted with one or more substituents selected from the group consisting of
(i) F
(ii) —CN
(iii) —$CO_2R^{11}$ where $R^{11}$ is $C_1$-$C_3$-alkyl or aryl substituted $C_1$-$C_3$-alkyl, or heteroalkyl substituted $C_1$-$C_3$-alkyl
(iv) —$C(O)NR^5R^6$ wherein $R^5$ and $R^6$ are defined as previously
(v) aryl, and optionally substituted aryl, and
(vi) heteroaryl, and optionally substituted heteroaryl
(4) $C_2$-$C_{10}$-alkyl
(5) substituted $C_2$-$C_{10}$-alkyl with one or more substituents selected from the group consisting of
(i) halogen,
(ii) $OR^4$ where $R^4$ is defined as previously
(iii) $C_1$-$C_3$-alkoxy-$C_1$-$C_3$-alkoxy
(iv) —CHO
(v) oxo
(vi) $NR^7R^8$ wherein $R^7$ and $R^8$ are as previously defined
(vii) =N—O—$R^4$ where $R^4$ is as previously defined
(viii) —CN
(ix) —$S(O)_nR^3$ where n=0, 1, or 2 and $R^3$ is as previously defined
(x) aryl, and optionally substituted aryl
(xi) heteroaryl, and optionally substituted heteroaryl
(xii) $C_3$-$C_8$-cycloalkyl, and optionally substituted $C_3$-$C_8$-cycloalkyl
(xiii) $C_1$-$C_{12}$-alkyl substituted with heteroaryl, and optionally substituted heteroaryl
(xiv) heterocycloalkyl
(xv) $NHC(O)R^3$ where $R^3$ is as previously defined
(xvi) $NHC(O)NR^5R^6$ where $R^5$ and $R^6$ are as previously defined
(xvii) =N—$NR^7R^8$ wherein $R^7$ and $R^8$ are as previously defined
(xviii) =N—$R^4$ wherein $R^4$ as previously defined, and
(xix) =N—$NHC(O)R^3$ wherein $R^3$ is as previously defined,
(4) $C_1$-$C_{10}$-alkenyl substituted with one or more substituents selected from the group consisting of
(i) halogen,
(ii) $OR^4$ where $R^4$ is as previously defined
(iii) —CHO
(iv) oxo
(v) —$S(O)_nR^3$ where n and $R^3$ are as previously defined
(vi) —CN
(vii) —$CO_2R^3$ where $R^3$ is as previously defined
(viii) $NR^7R^8$ wherein $R^7$ and $R^8$ are as previously defined
(ix) =N—O—$R^4$ where $R^4$ is as previously defined
(x) —C(O)—$R^4$ where $R^4$ is as previously defined
(xi) —$C(O)NR^5R^6$ wherein $R^5$ and $R^6$ are as previously defined
(xii) aryl, and optionally substituted aryl
(xiii) heteroaryl, and optionally substituted heteroaryl
(xiv) $C_3$-$C_7$-cycloalkyl
(xv) $C_1$-$C_{12}$-alkyl substituted with heteroaryl
(xvi) $NHC(O)R^3$ where $R^3$ is as previously defined
(xvii) $NHC(O)NR^5R^6$ where $R^5$ and $R^6$ are as previously defined
(xviii) =N—$NR^7R^8$ wherein le and $R^8$ are as previously defined
(xix) =N—$R^4$ wherein $R^4$ is as previously defined,
(xx) =N—$NHC(O)R^3$ wherein $R^3$ is as previously defined, and
(xxi) =N—$NHC(O)NR^5R^6$ wherein $R^5$ and $R^6$ are as previously defined,
(5) $C_2$-$C_{10}$-alkynyl, and
(6) $C_2$-$C_{10}$-alkynyl substituted with one or more substituents selected from the group consisting of
(i) halogen,
(ii) $OR^4$ where $R^4$ is defined as previously
(iii) —CHO
(iv) oxo
(v) —$CO_2R^3$ where $R^3$ is as previously defined
(vi) —$C(O)NR^5R^6$ wherein $R^5$ and $R^6$ are as previously defined
(vii) —CN
(viii) $NR^7R^8$ wherein $R^7$ and $R^8$ are as previously defined
(ix) =N—O—$R^4$ where $R^4$ is as previously defined
(x) —$S(O)_nR^3$ where n and $R^3$ are as previously defined
(xi) aryl, and optionally substituted aryl
(xii) heteroaryl, and optionally substituted heteroaryl
(xiii) $C_3$-$C_7$-cycloalkyl
(xiv) $C_1$-$C_{12}$-alkyl substituted with heteroaryl
(xv) $NHC(O)R^3$ where $R^3$ is as previously defined
(xvi) $NHC(O)NR^5R^6$ where $R^5$ and $R^6$ are as previously defined
(xvii) =N—$NR^7R^8$ wherein $R^7$ and $R^8$ are as previously defined
(xviii) =N—$R^4$ wherein $R^4$ is as previously defined
(xix) =N—$NHC(O)R^3$ wherein $R^3$ is as previously defined, and
(xx) =N—$NHC(O)NR^5R^6$ wherein $R^5$ and $R^6$ are as previously defined;
$R^2$ is selected from the group consisting of
(1) hydrogen
(2) OH
(3) $OR^3$ where $R^3$ is as previously defined
(4) $OC(O)R^3$ where $R^3$ is as previously defined, and
(5) $O(CO)OR^3$ where $R^3$ is as previously defined;
and X and Y taken together are selected from the group consisting of
(1) O
(2) $NOR^4$ wherein $R^4$ is as defined previously
(3) N—O $C(R^9)(CR^{10})$—O—$R^4$ where $R^4$ is as previously defined and
(i) $R^9$ and $R^{10}$ are each independently defined as $R^4$, or
(ii) $R^9$ and $R^{10}$ are taken together with the atom to which they are attached form a $C_3$-$C_{12}$ cycloalkyl ring,
(4) $NR^4$ wherein $R^4$ is as previously defined, and (5) N—NR$^7$R$^8$ wherein R$^7$ and R$^8$ are as previously defined, or one of X and Y is hydrogen and the other is selected from the group consisting of
(1) OR$^4$ wherein R$^4$ is as previously defined, and
(2) —NR$^7$R$^8$ wherein R$^7$ and R$^8$ are as previously defined, R$^P$ is selected from the group consisting of
(1) hydrogen
(2) R$^3$ as previously defined
(3) COR$^3$ where R$^3$ is as previously defined;
subject to the proviso that when the structure is IV, Z and M are part of a five- or six-membered ring, said rings optionally being fully or partially unsaturated; for the six- membered ring, the bonding between Z and M is through a carbonyl group; for the five- membered ring, the bonding is directly between Z and M excluding CO; Z and M are independently selected from the group consisting of carbon, oxygen or N; and when M=N a second bridge may exist between this nitrogen and the oxygen of the 12-OH group whereby either an additional annulated oxazole or oxazine ring constitutes part of the molecule; and subject to the proviso that when the structure is V, Z and M are part of a five- or six- membered ring, said rings optionally being fully saturated or fully or partially unsaturated; for the six- membered ring, the bonding between Z and M is through a carbonyl group; for the five-membered ring, the bonding is directly between Z and M excluding CO; Z and M are independently selected from the group consisting of carbon, oxygen or nitrogen; and when M=N a second bridge may exist between this nitrogen and the urethane nitrogen
wherein aryl groups have 5 to 10 ring atoms, and heteroaryl groups have 5 to 10 ring atoms including C and at least one of N, O and S.

2. A pharmaceutical composition comprising an antibiotic 10-desmethyl macrolide of claim 1 and a pharmaceutical excipient.

3. A method of treatment of a human or animal subject to combat bacterial infection thereof, which method comprises administering to said subject an antibiotic 10-desmethyl macrolide of claim 1.

* * * * *